US012622694B2

(12) United States Patent
Nguyen et al.

(10) Patent No.: US 12,622,694 B2
(45) Date of Patent: May 12, 2026

(54) SURGICAL STAPLER WITH DISCRETELY POSITIONABLE DISTAL TIP

(71) Applicant: Cilag GmbH International, Zug (CH)

(72) Inventors: Steven H. Nguyen, Cypress, TX (US); Nicolo Garbin, Houston, TX (US); Megan M. Greenwood, Royal Oak, MI (US); Benjamin N. Barnes, Houston, TX (US); Marcus P. Pantoja, Cypress, TX (US); David J. Salisbury, Kingwood, TX (US); Weston S. Hirschfeld, West Chester, OH (US); Pierre R. Mesnil, Newport, KY (US); Daniel V. Jones, Edgewood, KY (US)

(73) Assignee: Cilag GmbH International, Zug (CH)

( * ) Notice: Subject to any disclaimer, the term of this patent is extended or adjusted under 35 U.S.C. 154(b) by 102 days.

(21) Appl. No.: 18/241,311

(22) Filed: Sep. 1, 2023

(65) Prior Publication Data

US 2024/0115259 A1      Apr. 11, 2024

Related U.S. Application Data

(60) Provisional application No. 63/467,656, filed on May 19, 2023, provisional application No. 63/413,671, filed on Oct. 6, 2022.

(51) Int. Cl.
A61B 17/068 (2006.01)

(52) U.S. Cl.
CPC ................................ A61B 17/0686 (2013.01)

(58) Field of Classification Search
CPC ................ A61B 17/068; A61B 17/072; A61B 17/07207; A61B 17/115;

(Continued)

(56) References Cited

U.S. PATENT DOCUMENTS 2,887,111 A     5/1959  Leyro
4,608,981 A     9/1986  Rothfuss et al.
(Continued)

FOREIGN PATENT DOCUMENTS

EP      0537453 A1     4/1993
EP      2599452 A1     6/2013
(Continued)

OTHER PUBLICATIONS

Extended European Search Report from European Patent Application No. 24205253, dated Dec. 9, 2024, 11 pages.
(Continued)

*Primary Examiner* — Anna K Kinsaul
(74) *Attorney, Agent, or Firm* — Lempia Summerfield Katz LLC

(57)                    ABSTRACT

An apparatus includes a first jaw (16) and a second jaw (618, 718, 900) that cooperate to clamp and staple tissue (90). The second jaw includes a jaw body (620, 720, 902) and a distal tip (619, 719, 906) pivotable relative to the jaw body between a first discrete and a second discrete position. First and second openings (663, 784, 785, 932, 934) are both defined by one of the distal tip or a structure (621, 920) located proximal to the distal tip. A projection (637, 781, 918) is defined by the other of the distal tip or the structure. The projection is positionable within the first opening (663, 785, 932) to releasably retain the distal tip in the first discrete position, and within the second opening (663, 784, 934) to releasably retain the distal tip in the second discrete position.

14 Claims, 45 Drawing Sheets

(58) Field of Classification Search
CPC ........... A61B 2017/00473; A61B 2017/00477;
A61B 2017/07214; A61B 2017/07271;
A61B 2017/07285
USPC ......... 227/19, 175.1, 176.1; 606/1, 139, 219
See application file for complete search history.

(56) References Cited

U.S. PATENT DOCUMENTS

| | | | |
|---|---|---|---|
| 4,981,149 | A | 1/1991 | Yoon et al. |
| 5,129,570 | A | 7/1992 | Schulze et al. |
| 5,397,324 | A | 3/1995 | Carroll et al. |
| 5,447,265 | A | 9/1995 | Vidal et al. |
| 5,476,206 | A | 12/1995 | Green et al. |
| 5,507,426 | A | 4/1996 | Young et al. |
| 5,549,621 | A | 8/1996 | Bessler et al. |
| 5,562,211 | A | 10/1996 | Simons et al. |
| 5,649,957 | A | 7/1997 | Levin |
| 5,766,187 | A | 6/1998 | Sugarbaker |
| 5,772,099 | A | 6/1998 | Gravener |
| 5,922,008 | A | 7/1999 | Gimpelson |
| 5,941,442 | A | 8/1999 | Geiste et al. |
| 6,241,740 | B1 | 6/2001 | Davis et al. |
| 6,446,854 | B1 | 9/2002 | Remiszewski et al. |
| 6,736,793 | B2 | 5/2004 | Meyer et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,300,444 | B1 | 11/2007 | Nielsen et al. |
| 7,303,108 | B2 | 12/2007 | Shelton, IV |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,588,177 | B2 | 9/2009 | Racenet |
| 7,644,848 | B2 | 1/2010 | Swayze et al. |
| 7,682,368 | B1 | 3/2010 | Bombard et al. |
| 7,721,930 | B2 | 5/2010 | McKenna et al. |
| 7,866,523 | B1 | 1/2011 | White et al. |
| 7,914,543 | B2 | 3/2011 | Roth et al. |
| 8,066,166 | B2 | 11/2011 | Demmy et al. |
| 8,136,711 | B2 | 3/2012 | Beardsley et al. |
| 8,210,411 | B2 | 7/2012 | Yates et al. |
| 8,348,123 | B2 | 1/2013 | Scirica et al. |
| 8,403,195 | B2 | 3/2013 | Beardsley et al. |
| 8,403,196 | B2 | 3/2013 | Beardsley et al. |
| 8,408,439 | B2 | 4/2013 | Huang et al. |
| 8,453,914 | B2 | 6/2013 | Laurent et al. |
| 8,496,153 | B2 | 7/2013 | Demmy et al. |
| 8,690,039 | B2 | 4/2014 | Beardsley et al. |
| 8,714,429 | B2 | 5/2014 | Demmy |
| 8,844,790 | B2 | 9/2014 | Demmy et al. |
| 9,016,546 | B2 | 4/2015 | Demmy et al. |
| 9,039,736 | B2 | 5/2015 | Scirica et al. |
| 9,186,142 | B2 | 11/2015 | Fanelli et al. |
| 9,433,416 | B2 | 9/2016 | Beardsley et al. |
| 9,517,065 | B2 | 12/2016 | Simms et al. |
| 9,522,004 | B2 | 12/2016 | Demmy |
| 9,597,078 | B2 | 3/2017 | Scirica et al. |
| 9,622,746 | B2 | 4/2017 | Simms et al. |
| 9,713,470 | B2 | 7/2017 | Scirica et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,913,642 | B2 | 3/2018 | Leimbach et al. |
| 9,936,952 | B2 | 4/2018 | Demmy |
| 9,936,968 | B2 | 4/2018 | Demmy et al. |
| 9,943,311 | B2 | 4/2018 | Scirica et al. |
| 10,080,564 | B2 | 9/2018 | Beardsley et al. |
| 10,092,292 | B2 | 10/2018 | Boudreaux et al. |
| D833,010 | S | 11/2018 | Harris et al. |
| D836,198 | S | 12/2018 | Harris et al. |
| D836,199 | S | 12/2018 | Schowalter et al. |
| 10,182,813 | B2 | 1/2019 | Leimbach et al. |
| 10,507,032 | B2 | 12/2019 | Demmy et al. |
| 10,779,827 | B2 | 9/2020 | Scirica et al. |
| 10,786,252 | B2 | 9/2020 | Harris et al. |
| 10,973,516 | B2 | 4/2021 | Shelton, IV et al. |
| 11,103,244 | B2 | 8/2021 | Harris et al. |
| 11,123,066 | B2 | 9/2021 | Beardsley et al. |
| 11,185,327 | B2 | 11/2021 | Harris et al. |
| 11,272,930 | B2 | 3/2022 | Harris et al. |
| 11,304,697 | B2 | 4/2022 | Fanelli et al. |
| 11,317,912 | B2 | 5/2022 | Jenkins et al. |
| 11,439,391 | B2 | 9/2022 | Bruns et al. |
| 11,564,684 | B2 | 1/2023 | Harris et al. |
| 11,564,687 | B2 | 1/2023 | Harris et al. |
| 12,336,708 | B2 * | 6/2025 | Baril ...................... A61B 90/03 |
| 2002/0065534 | A1 | 5/2002 | Hermann et al. |
| 2002/0099375 | A1 | 7/2002 | Hess et al. |
| 2004/0193186 | A1 | 9/2004 | Kortenbach et al. |
| 2004/0243151 | A1 | 12/2004 | Demmy et al. |
| 2010/0094315 | A1 | 4/2010 | Beardsley et al. |
| 2011/0106150 | A1 | 5/2011 | Hausen et al. |
| 2012/0143218 | A1 | 6/2012 | Beardsley et al. |
| 2013/0334280 | A1 | 12/2013 | Krehel et al. |
| 2014/0166723 | A1 | 6/2014 | Beardsley et al. |
| 2018/0235610 | A1 | 8/2018 | Harris et al. |
| 2018/0235611 | A1 | 8/2018 | Harris et al. |
| 2018/0235619 | A1 | 8/2018 | Harris et al. |
| 2019/0000481 | A1 | 1/2019 | Harris et al. |
| 2019/0015100 | A1 | 1/2019 | Yigit et al. |
| 2020/0015812 | A1 | 1/2020 | Harris et al. |
| 2020/0015813 | A1 | 1/2020 | Harris et al. |
| 2020/0015814 | A1 | 1/2020 | Harris et al. |
| 2020/0015815 | A1 | 1/2020 | Harris et al. |
| 2020/0015817 | A1 | 1/2020 | Harris et al. |
| 2020/0205825 | A1 | 7/2020 | Vendely et al. |
| 2020/0237368 | A1 | 7/2020 | Bruns |
| 2020/0237369 | A1 | 7/2020 | Jenkins et al. |
| 2020/0237370 | A1 | 7/2020 | Fanelli et al. |
| 2020/0345357 | A1 | 11/2020 | Leimbach et al. |
| 2021/0177401 | A1 | 6/2021 | Abramek et al. |
| 2021/0307744 | A1 | 10/2021 | Walcott et al. |

FOREIGN PATENT DOCUMENTS

| | | | |
|---|---|---|---|
| EP | 2674111 | A2 | 12/2013 |
| EP | 2777523 | A1 | 9/2014 |
| WO | 2004096057 | A3 | 12/2004 |
| WO | 2013151888 | A1 | 10/2013 |
| WO | 2016094236 | A1 | 6/2016 |

OTHER PUBLICATIONS

European Search Report and Written Opinion dated Apr. 8, 2020 for Application No. EP 20154700.7, 12 pgs.
European Search Report and Written Opinion dated Apr. 21, 2020 for Application No. EP 20154720.5, 10 pgs.
European Search Report and Written Opinion dated May 8, 2020 for Application No. EP 20154723.9, 10 pgs.
International Search Report and Written Opinion dated Apr. 8, 2020 for International Application No. PCT/IB2020/050700, 12 pages.
International Search Report and Written Opinion dated Apr. 21, 2020 for International Application No. PCT/IB2020/050703, 11 pages.
International Search Report and Written Opinion dated May 4, 2020 for International Application No. PCT/IB2020/050701, 11 pages.
International Search Report and Written Opinion of the International Searching Authority from International Patent Application No. PCT/IB2023/059995, dated Feb. 5, 2024, 24 pages.

* cited by examiner

SURGICAL STAPLER WITH DISCRETELY POSITIONABLE DISTAL TIP

RELATED APPLICATIONS

This application claims the benefit of the filing date under 35 U.S.C. § 119(e) of U.S. Provisional Application Ser. No. 63/413,671, filed Oct. 6, 2022 and U.S. Provisional Application Ser. No. 63/467,656, filed May 19, 2023, the entirety of both of which are incorporated by reference herein and relied upon.

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path. In some such procedures, the clinician may have a need or desire to adjust the position of a distal tip of the end effector during the surgical procedure to better facilitate the manipulation of and firing on tissue. However, known surgical staplers have limited capabilities for such adjustment.

The surgical stapling features of the present disclosure seek to enable a clinician to quickly and precisely adjust the position of a distal tip of a surgical stapler end effector during a surgical procedure. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
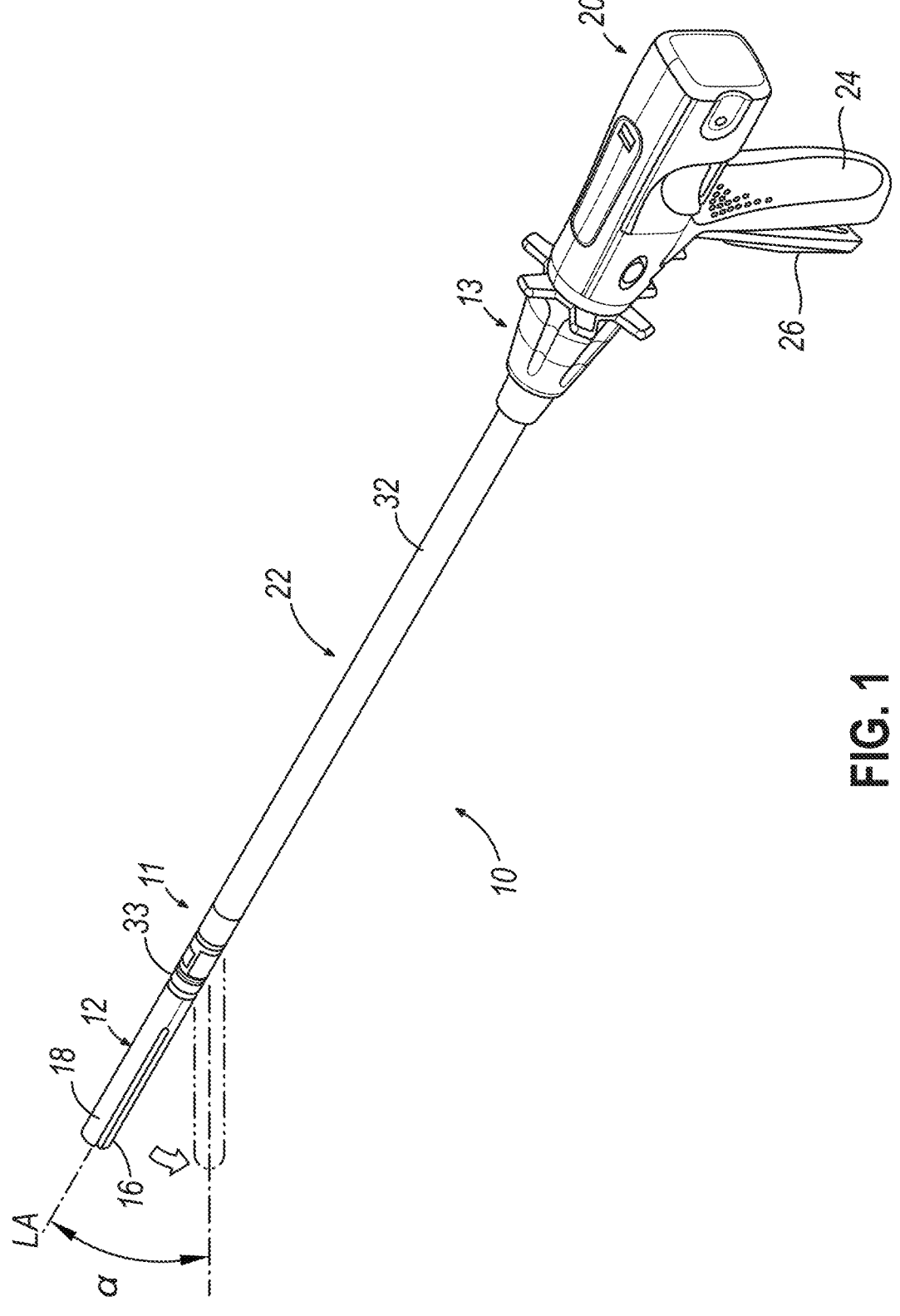
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) (also referred to herein as a cartridge jaw) that includes a staple cartridge (37), and an upper jaw in the form of a pivotable anvil jaw (18).

Unless otherwise described, the term "pivot" (and variations thereof) as used herein encompasses but is not necessarily limited to pivotal movement about a fixed axis. For instance, in some versions, anvil jaw (18) may pivot about an axis that is defined by a pin (or similar feature) that slidably translates along an elongate slot or channel as anvil jaw (18) moves toward lower jaw (16). Such translation may occur before, during, or after the pivotal motion. It should therefore be understood that such combinations of pivotal and translational movement are encompassed by the term "pivot" and variations thereof as used herein.

Handle portion (20) includes a pistol grip (24) and a closure trigger (26). Closure trigger (26) is pivotable toward pistol grip (24) to cause clamping, or closing, of anvil jaw (18) toward lower jaw (16) of end effector (12). Such closing of anvil jaw (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
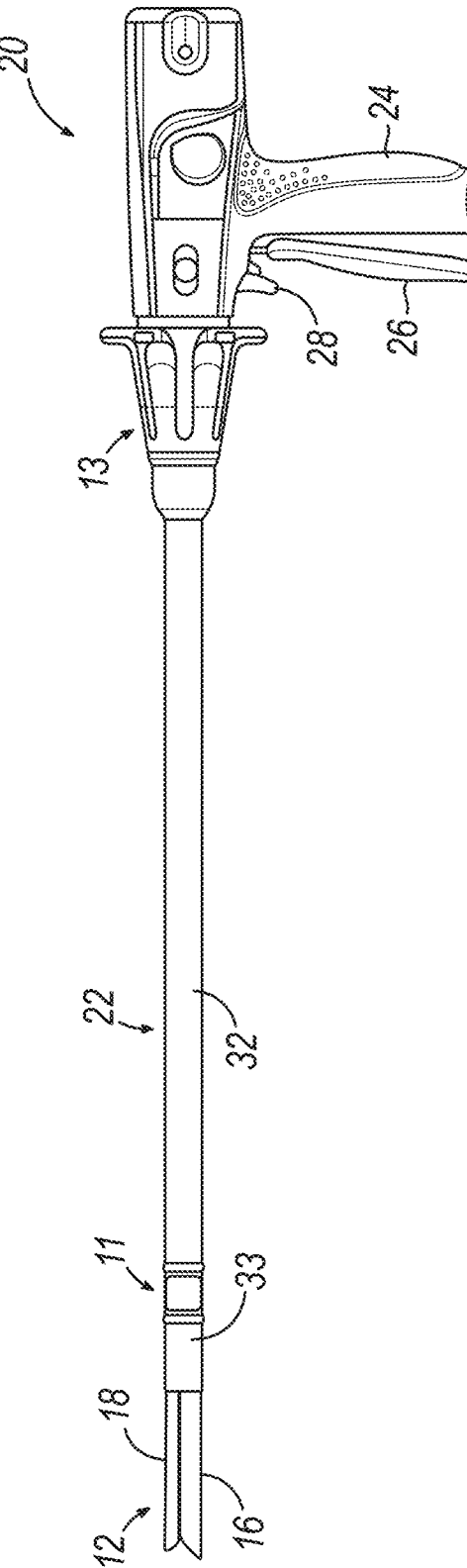
FIG. 2 depicts a side view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil jaw (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
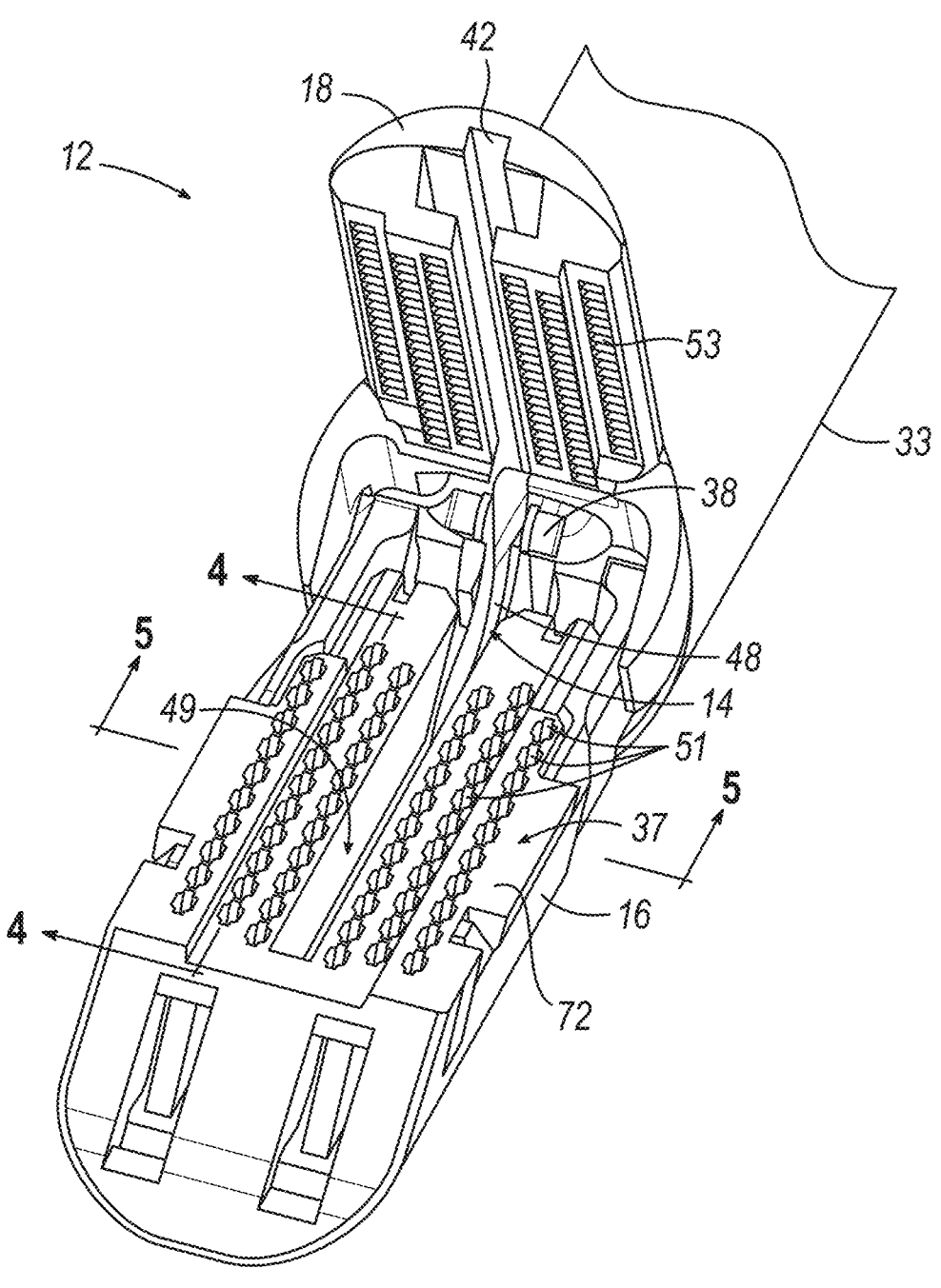
FIG. 3 depicts a perspective view of an opened end effector of the instrument of FIG. 1.
Figure 4A:
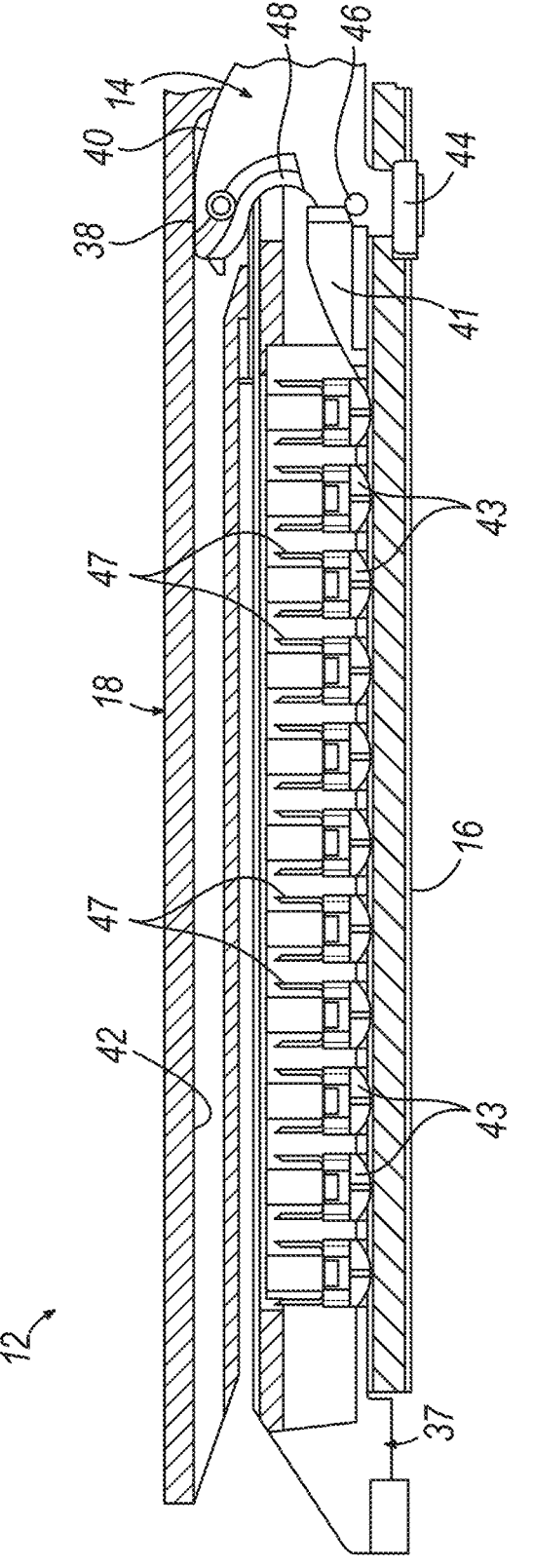
FIG. 4A depicts a side cross-sectional view of the end effector of FIG. 3, taken along line 4-4 of FIG. 3, with the firing beam in a proximal position.
Figure 4B:
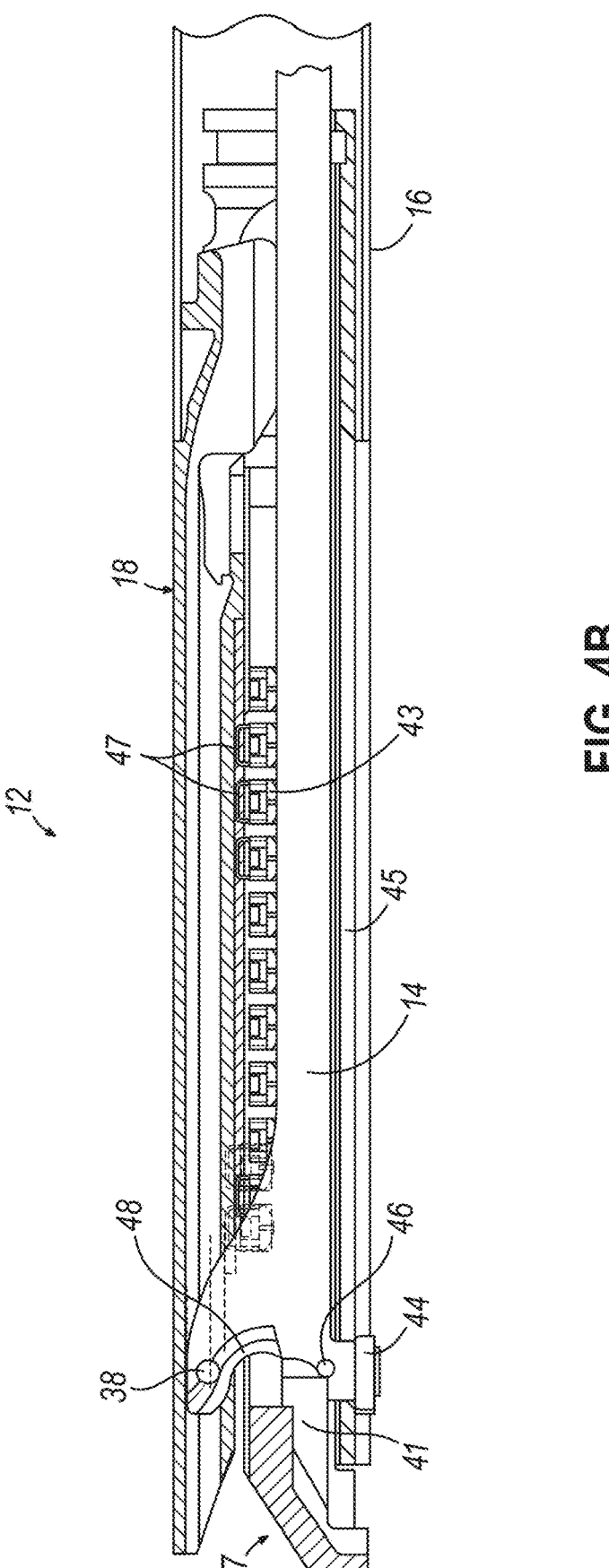
FIG. 4B depicts a side cross-sectional view of the end effector of FIG. 3, taken along line 4-4 of FIG. 3, with the firing beam in a distal position.
Figure 5:
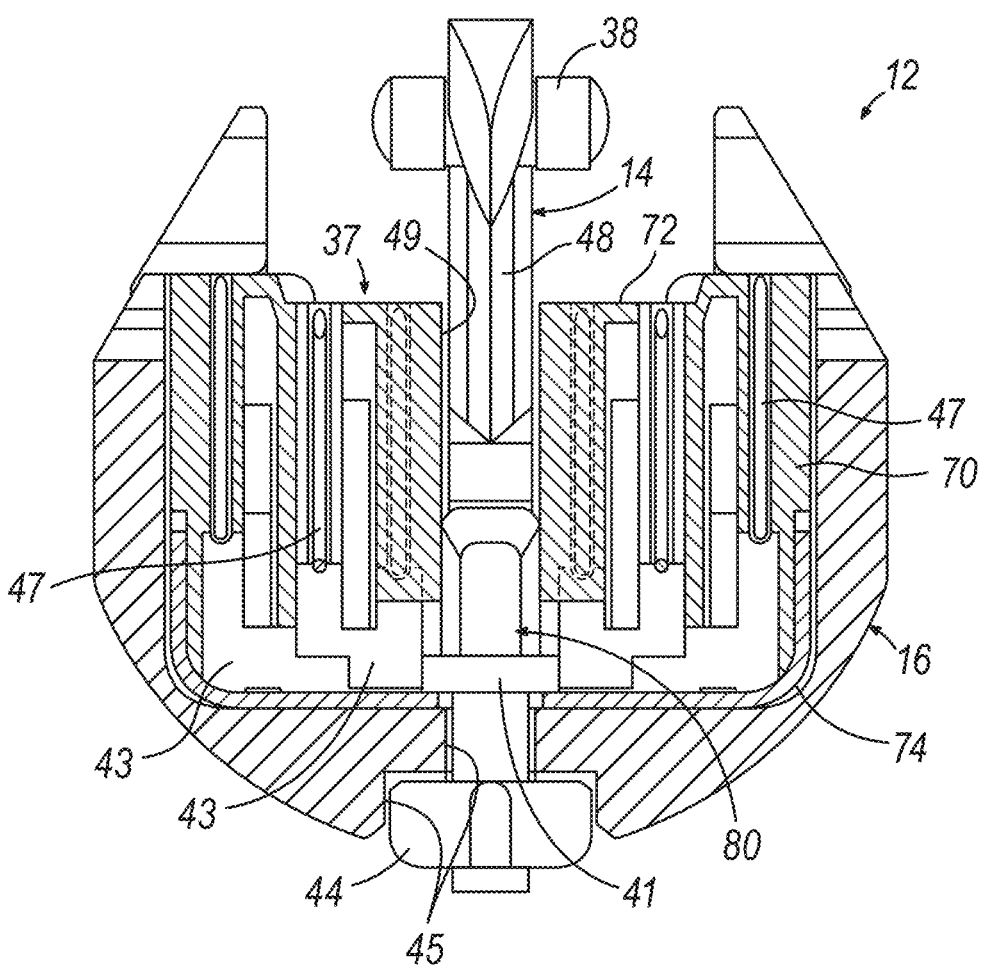
FIG. 5 depicts an end cross-sectional view of the end effector of FIG. 3, taken along line 5-5 of FIG. 3.
Figure 6:
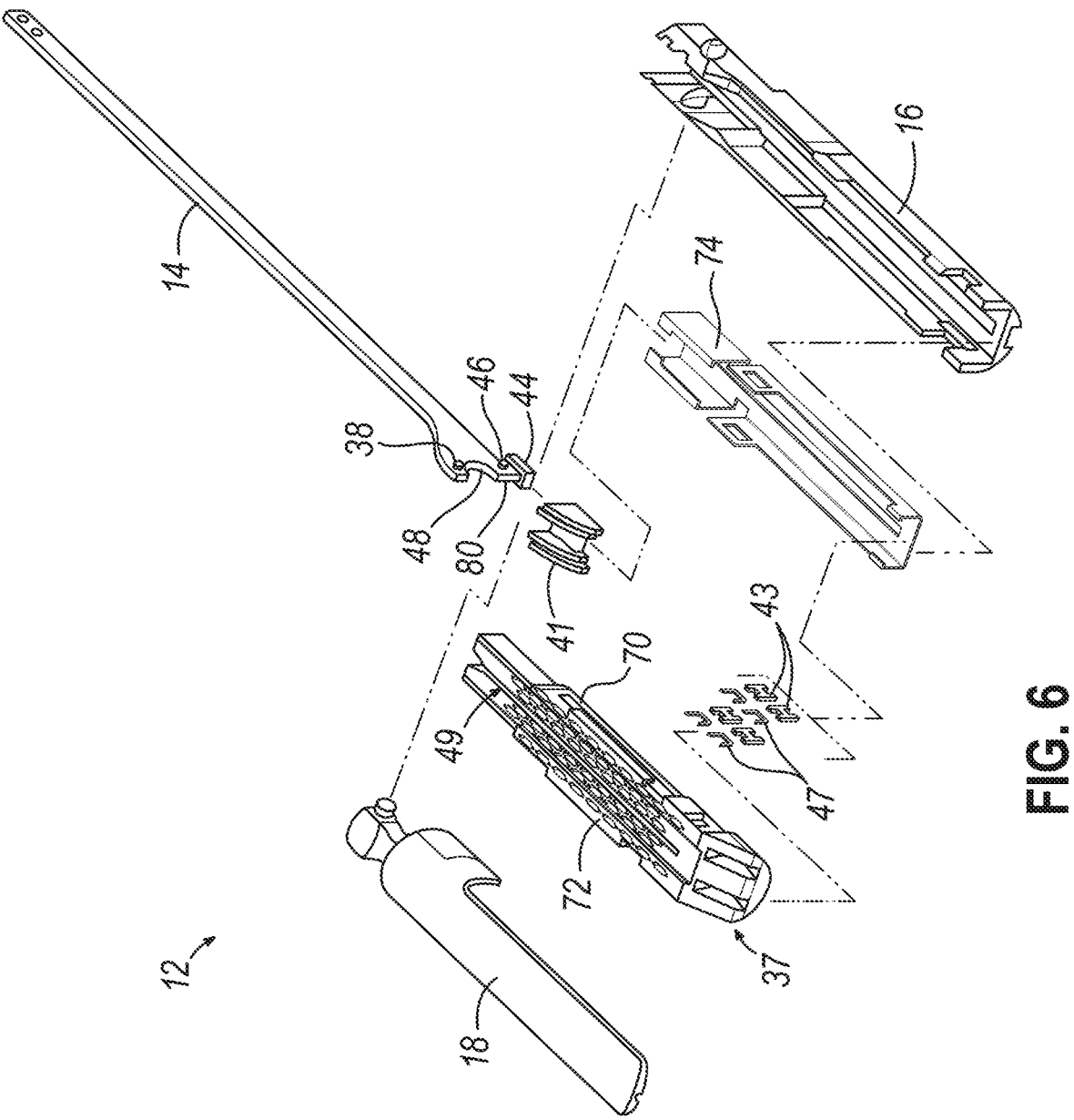
FIG. 6 depicts an exploded perspective view of the end effector of FIG. 3.

FIG. 3 shows firing beam (14) of the present example proximally positioned and anvil jaw (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), a firing member in the form of firing beam (14) is then advanced distally into engagement with anvil jaw (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil jaw (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil jaw (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil jaw (18) is intentionally omitted from the view in FIG. 5.

Figure 7:
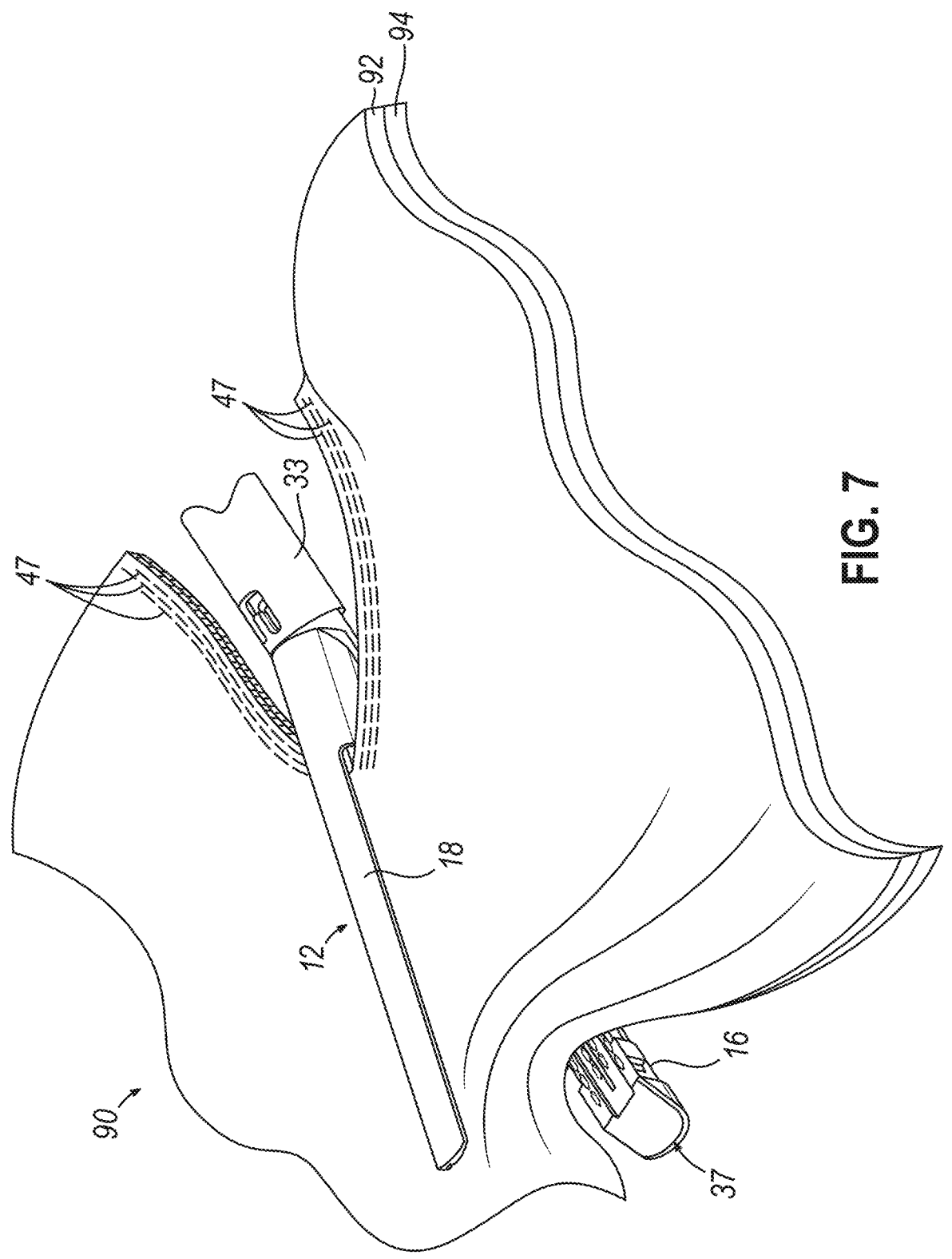
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. End Effector with Visualization, Lead-In, and Gathering Feature

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil jaw (18). Alternatively, end effector (12) could be rotated such that when the user views end effector (12), anvil jaw (18) is visible by the user. It may be desirable to provide visibility of the surgical site for the user beyond what is possible in instrument (10) of FIG. 1.

For instance, in the case of some surgical procedures where fluid carrying vessels are transected and stapled, it may be desirable to have visual confirmation that anvil jaw (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil jaw (18) and lower jaw (16) to fully clamp the vessel. One potential way of monitoring the surgical site may include improving visualization of the area adjacent to the distal tip of lower jaw (16) and anvil jaw (18). Furthermore, not only visualization of the distal end of end effector (12) may be desirable, but also it may be desirable to construct end effector (12) such that the distal end of anvil jaw (18) is configured to urge tissue (e.g., a large vessel) proximally into the space between anvil jaw (18) and lower jaw (16) as anvil jaw (18) closes toward lower jaw (16).

Figure 8:
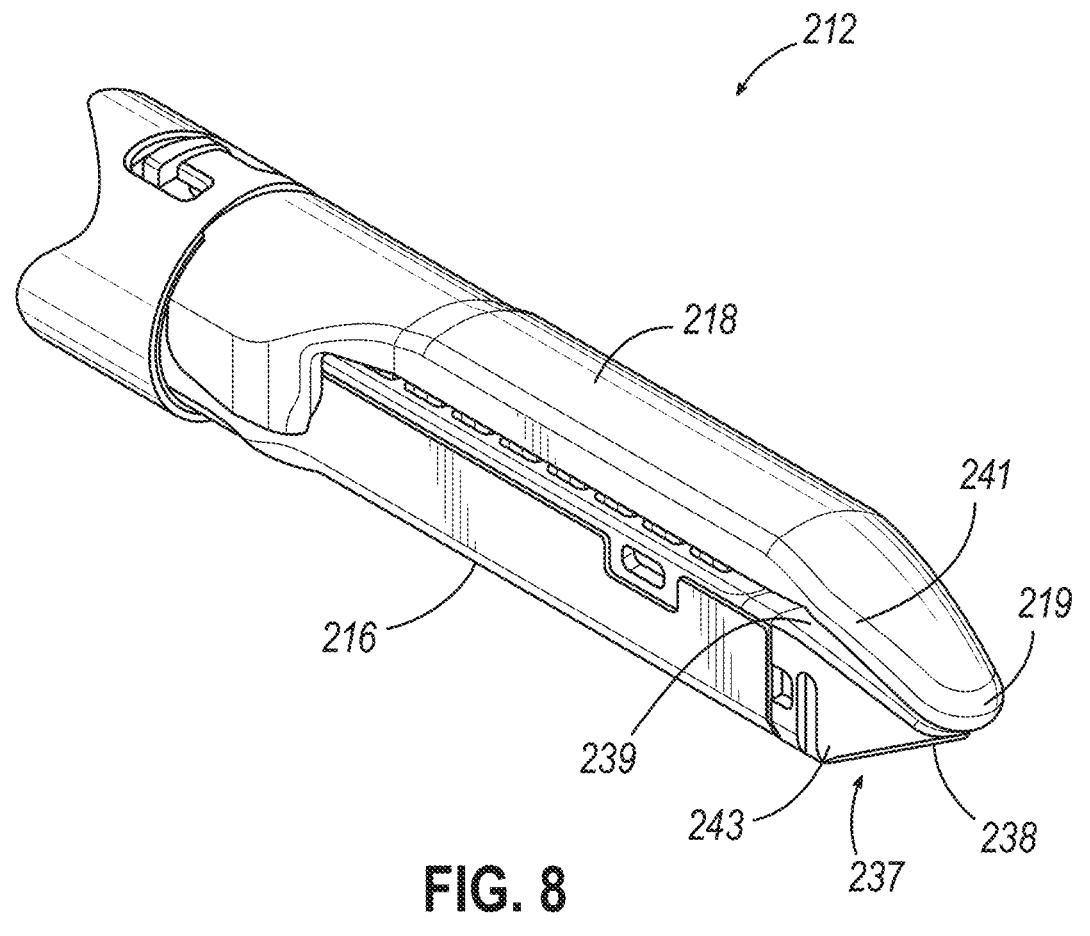
FIG. 8 depicts a perspective view of an alternative version of an end effector with an angled anvil jaw and an angled cartridge.

FIG. 8 depicts an example of an end effector (212) comprising an anvil jaw (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil jaw (218) is operable to pivot relative to lower jaw (216). Anvil jaw (218) and lower jaw (216) may clamp tissue (90) similarly to clamping performed by anvil jaw (18) and lower jaw (16) shown in FIG. 1. End effector (212) further includes a cartridge (237) operable to be placed in lower jaw (216) similarly to cartridge (37) shown in FIG. 3.

Figure 9:
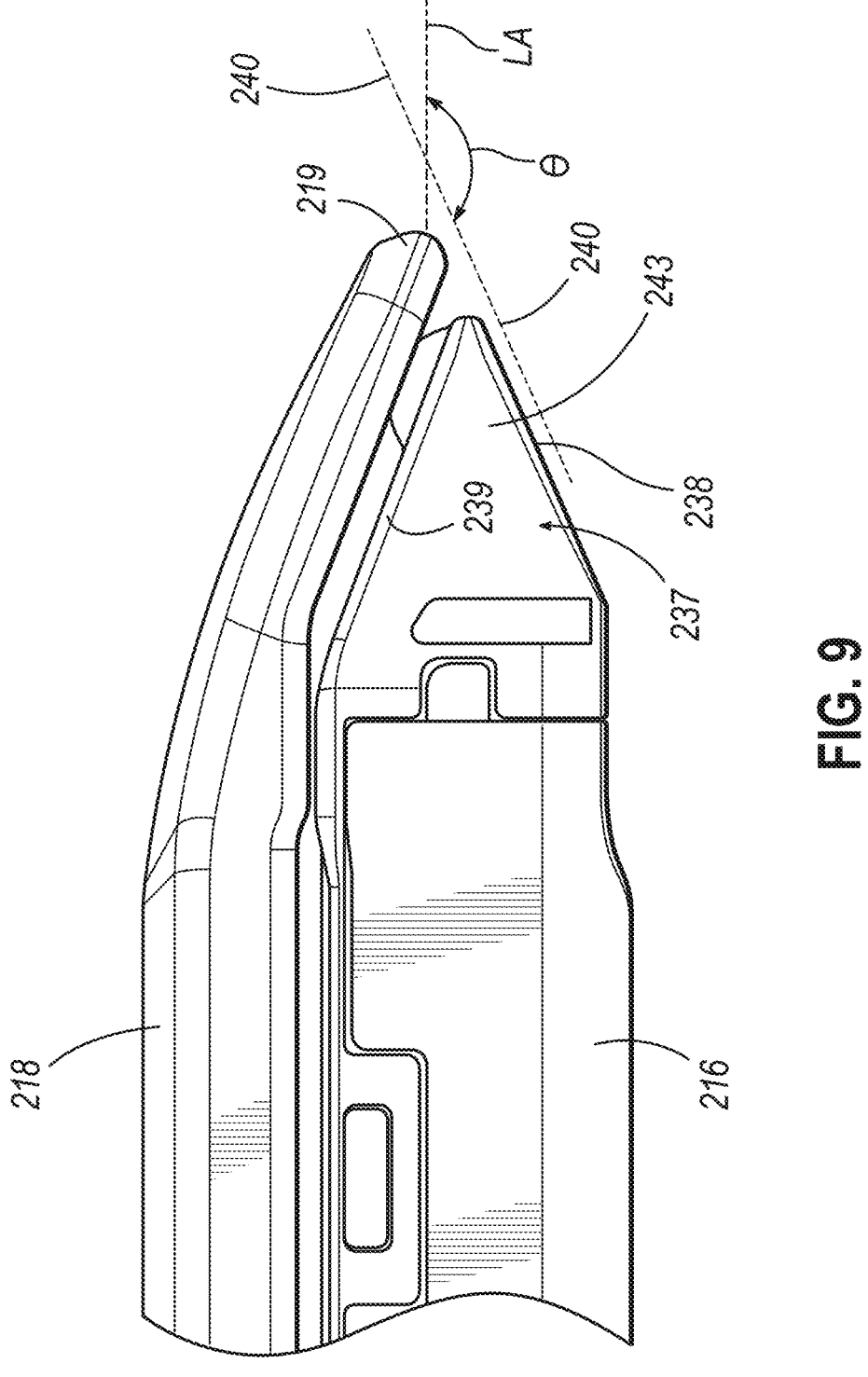
FIG. 9 depicts an enlarged, side view of the end effector of FIG. 8.
Figure 10:
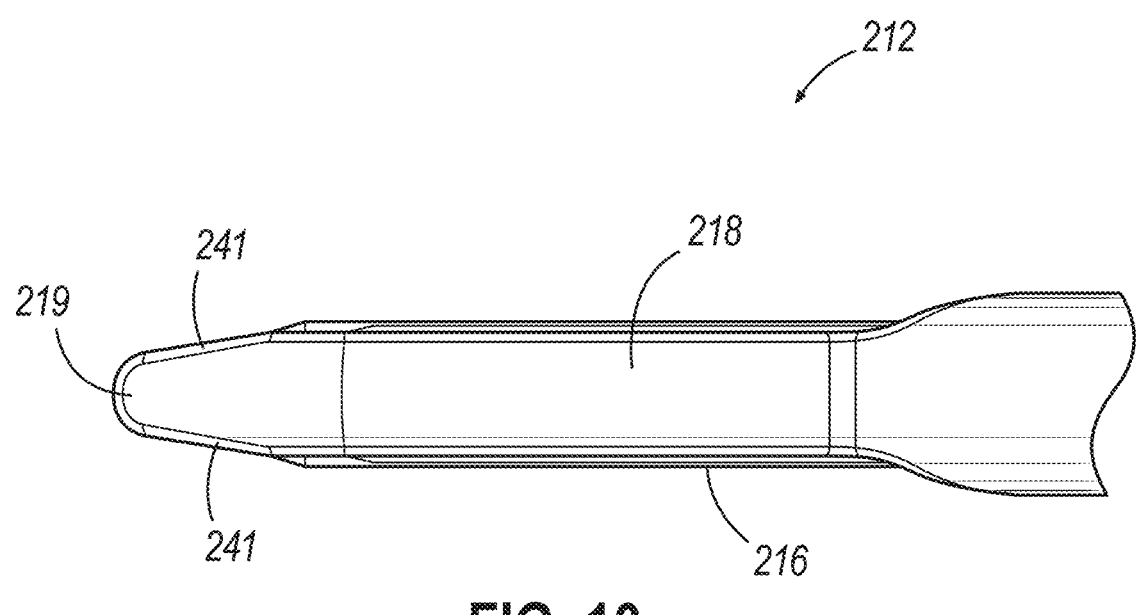
FIG. 10 depicts an enlarged top view of the end effector of FIG. 8.

Anvil jaw (218) as can be seen in FIGS. 8-10 has an elongated shape where the distal portion of anvil jaw (218) angles toward cartridge (237). The distal portion of anvil jaw (218) angles toward cartridge (237) such that the distal most distal tip (219) of anvil jaw (218) extends distally longitudinally further than cartridge (237). Though in some versions, distal tip (219) may extend to a distance longitudinally equal to cartridge (237) or proximal relative to the distal most point on cartridge (237). Furthermore, anvil jaw (218) angles toward cartridge (237) through a gentle slope. As seen best in FIG. 10, anvil jaw (218) includes sides (241) that taper as they approach the distal most distal tip (219) of anvil jaw (218). By way of example, anvil jaw (218) is shaped in FIG. 8 similarly to an inverted ski tip. The angled shape of anvil jaw (218) may provide easier insertion of end effector (212) into a surgical site. For instance, the gentle slope or inverted ski tip shape of anvil jaw (218) may provide an atraumatic tissue deflection surface as anvil jaw (218) contacts or moves through tissue. Such atraumatic tissue deflection may include urging tissue (e.g., a large vessel) proximally into the space between anvil jaw (218) and lower jaw (216) as anvil jaw (218) closes toward lower jaw (216). Once placed into a surgical site, the angled shape of anvil jaw (218) may also provide better maneuverability of end effector (212) and better visibility of the distal end of end effector (212) in relation to anatomical structures at the surgical site. Other suitable variations of anvil jaw (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) includes an upper tapered surface (239) and a lower tapered surface (238). Additionally, the distal end of cartridge (237) includes a tapered side surface (243) on each side. In the present example, each tapered side surface (243) of cartridge (237) generally aligns with the taper presented by sides (241) of anvil jaw (218). Thus, as shown in FIG. 10, side surfaces (243) of cartridge (237) do not extend outwardly from longitudinal axis (LA) of end effector (212) past sides (241) of anvil jaw (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil jaw (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil jaw (218), the user can look along sight line (240) or elsewhere within viewing angle (θ) to see, for instance, precisely where anvil jaw (218) has clamped tissue (90). Furthermore, the user would be able to determine whether the tissue is completely clamped between anvil jaw (218) and cartridge (237) such that tissue does not spill over the end of end effector (212). The user may be able to also visualize the quality of the clamp between anvil jaw (218) and cartridge (237) against tissue (90). It will be appreciated that in some instances, end effector (212) may be rotated before, during, or after clamping tissue (90). As a result, the tapered shape of anvil jaw (218) may also provide more accessible viewing of distal tip (219) or substantially adjacent distal tip (219). The taper of anvil jaw (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil jaw (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil jaw (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. End Effectors with Angled Elastically Deformable Distal Tips

As can be seen in FIGS. 4A-4B and FIG. 7, the distal end configuration of end effector (12) provides a gap between the distal end of anvil jaw (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil jaw (218) and lower jaw (216) as anvil jaw (218) is closed toward lower jaw (216). However, in versions where all the structures of end effector (212) are rigid, the bent configuration of distal tip (219) of anvil jaw (218) may not lend itself well to marching operations, as distal tip (219) may impart trauma to tissue that is not gathered into the space between anvil jaw (218) and lower jaw (216) as anvil jaw (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil jaw has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil jaw with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil jaw having a bias to an angled position when not in a loaded state or contacted by surrounding tissue, enhanced visualization during tissue capture and cutting can be achieved compared to using end effectors with a straight or non-angled anvil jaw. Moreover, an anvil jaw with a distal tip that is biased to an angled position may provide some degree of tissue gathering effects up until reaching a load point that would be associated with marching rather than being associated with simply gathering a relatively small tissue structure between the anvil jaw and lower jaw.

Figure 11:
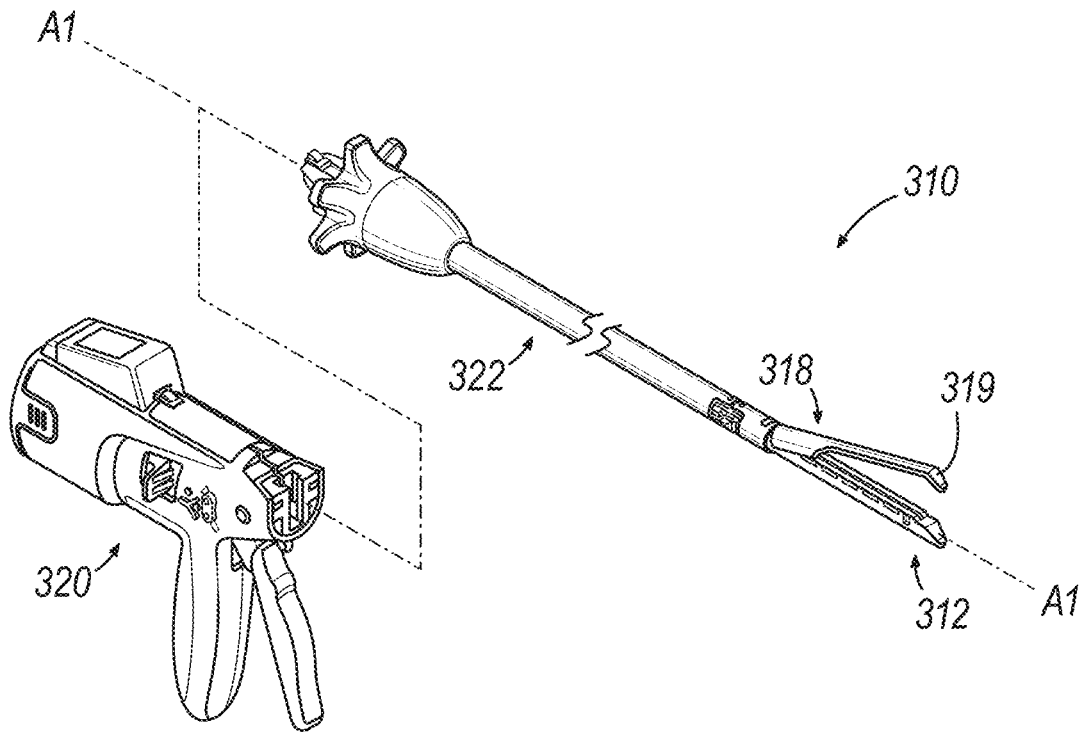
FIG. 11 depicts a perspective view of an example of a surgical stapling instrument having an end effector with a curved elastically deformable tip section.

FIG. 11 shows another example of an instrument (310) configured as a surgical stapler. Instrument (310) includes a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) includes an end effector (312) having an anvil jaw (318) that has an angled distal tip (319). Furthermore, distal tip (319) of anvil jaw (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil jaw (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
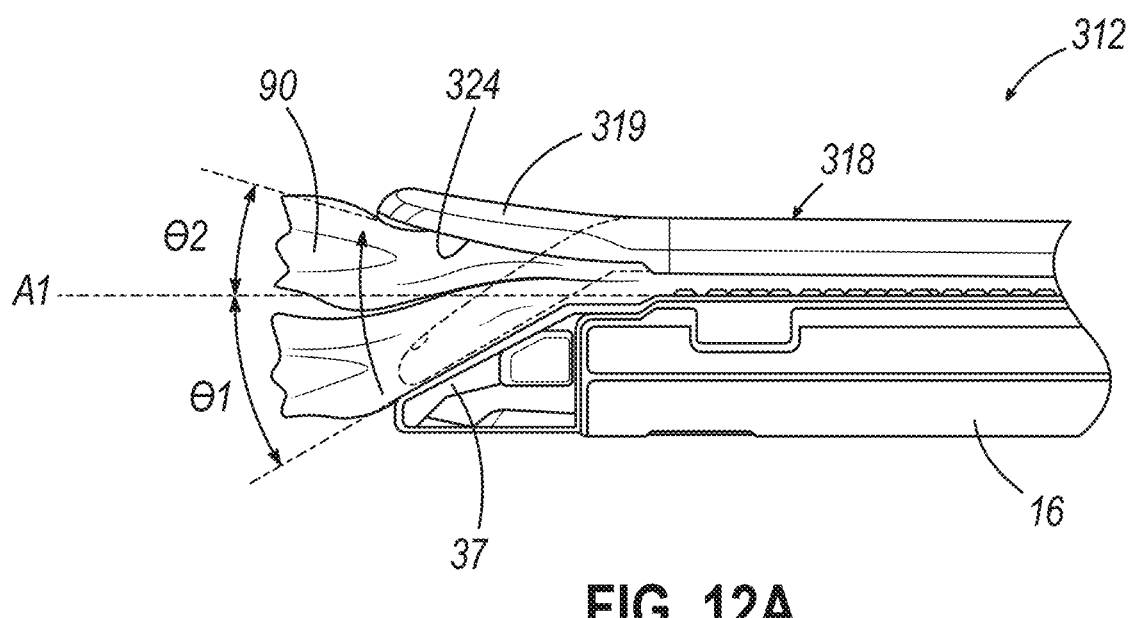
FIG. 12A depicts an enlarged side view of a distal portion of the end effector of FIG. 11.

FIG. 12A shows an enlarged side view of the distal end of end effector (312). End effector (312) includes anvil jaw (318) and lower jaw (16) that accepts cartridge (37) as described above with respect to instrument (10). Anvil jaw (318) pivotably rotates toward lower jaw (16) in the same manner as anvil jaw (18) as described above with respect to instrument (10). In this configuration, end effector (312) is similar to end effector (12), however, anvil jaw (318) includes angled distal tip (319) that is elastically deformable. As shown in FIG. 12A, distal tip (319) is imparted with a bias to an angled position that is shown in FIG. 11 and in phantom in FIG. 12A. Distal tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil jaw (318) and lower jaw (16), distal tip (319) contacts cartridge (37). In this position, an underside surface (324) of distal tip (319) defines a plane that intersects a longitudinal axis (A1) defined by shaft (322) to form an angle (θ1). When closed and clamping tissue (90) between anvil jaw (318) and lower jaw (16), underside surface (324) of distal tip (319) contacts tissue (90). In this position, underside surface (324) of distal tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by distal tip (319) is between about 20 degrees and about 110 degrees. The angles described for angles (θ1, θ2) are examples only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
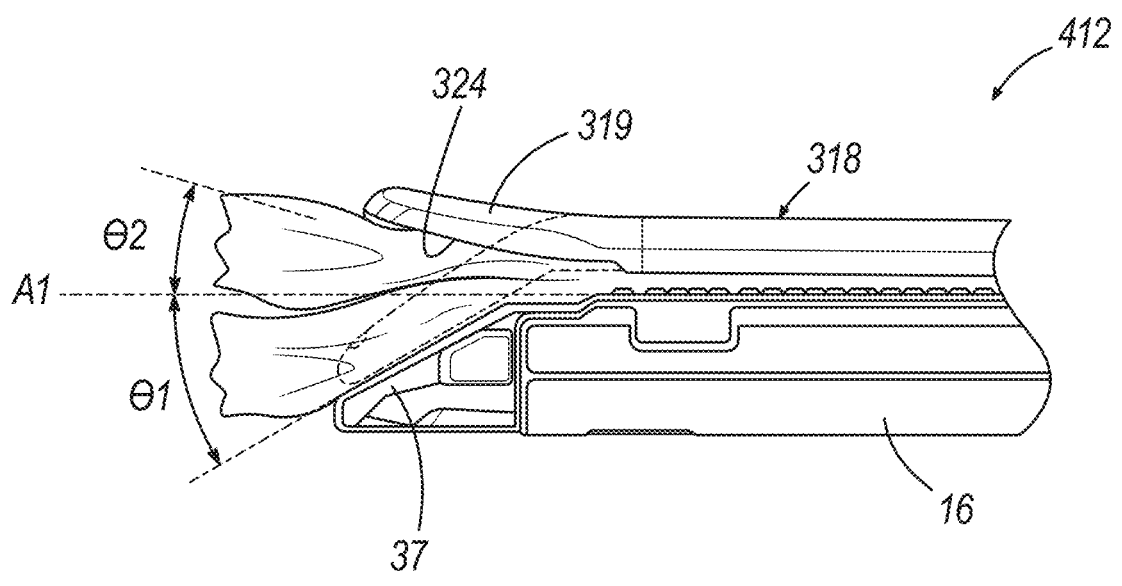
FIG. 12B depicts an enlarged side view of a distal portion of an alternate end effector similar to that of FIG. 11.
Figure 13:
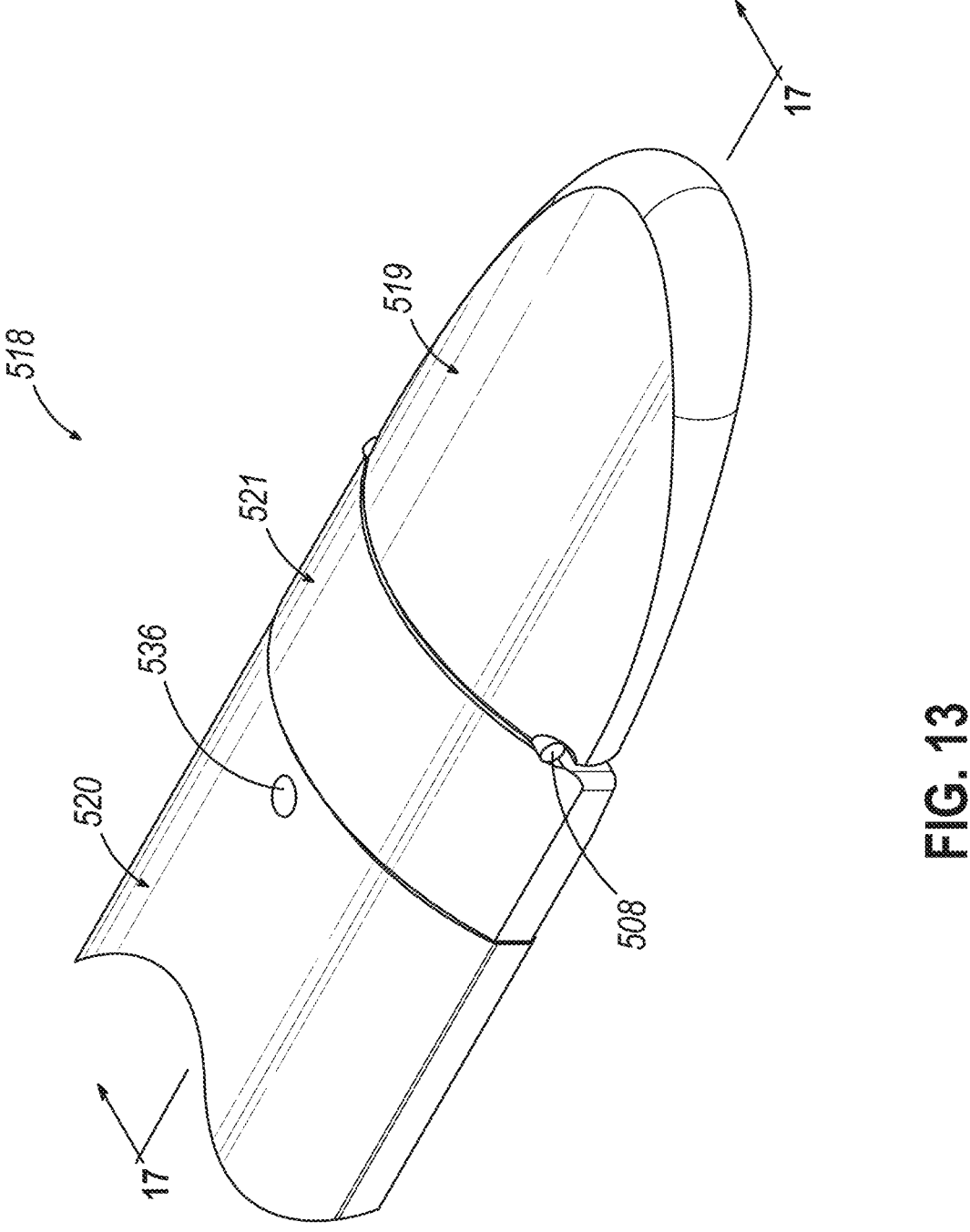
FIG. 13 depicts a perspective view of a distal portion of another anvil jaw configured for use with the surgical instruments described herein.
Figure 14:
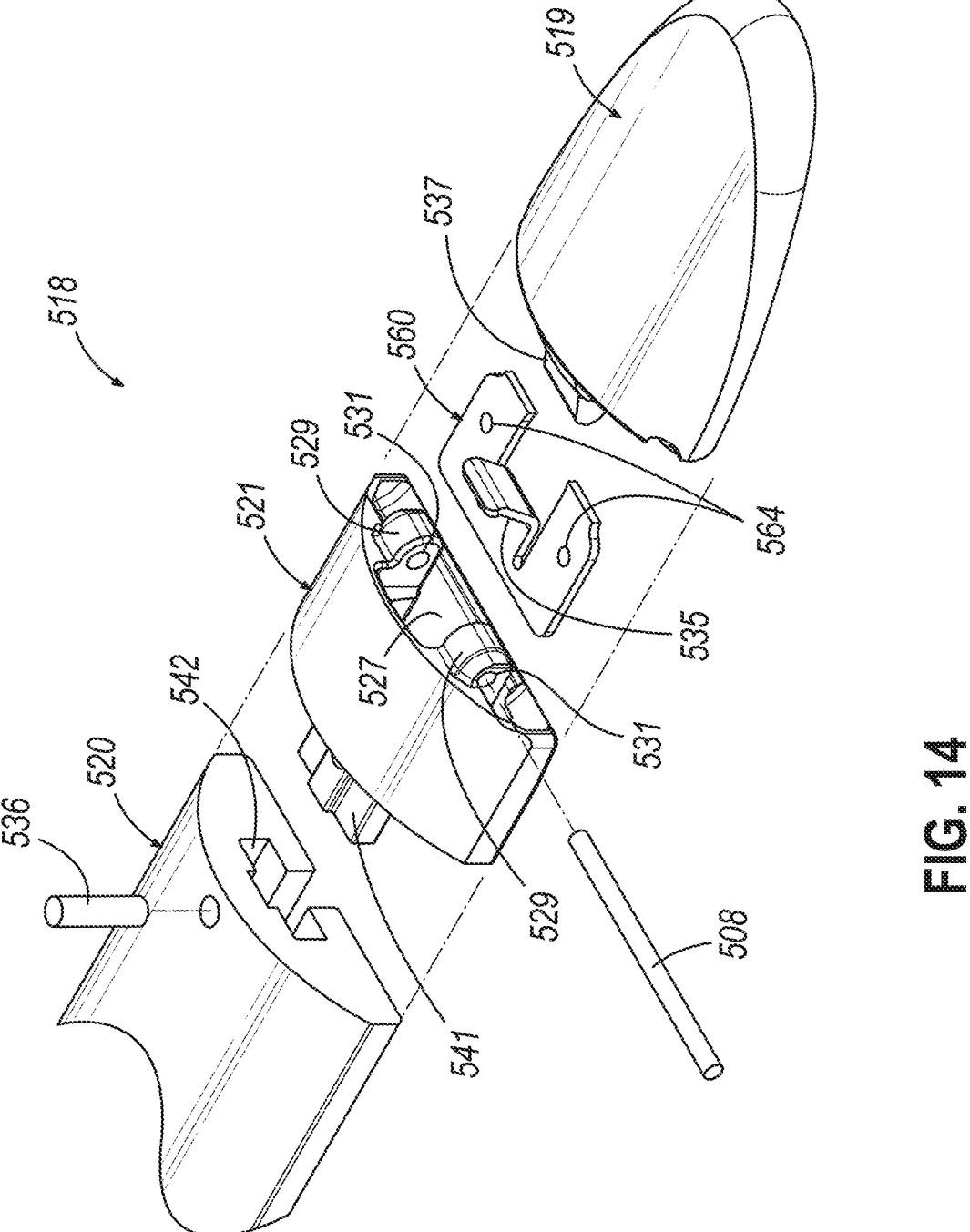
FIG. 14 depicts a proximally facing upper exploded perspective view of the distal portion of the anvil jaw of FIG. 13, showing an anvil body, a distal tip, a connector, a spring plate, a pivot pin, and a connector pin.
Figure 15:
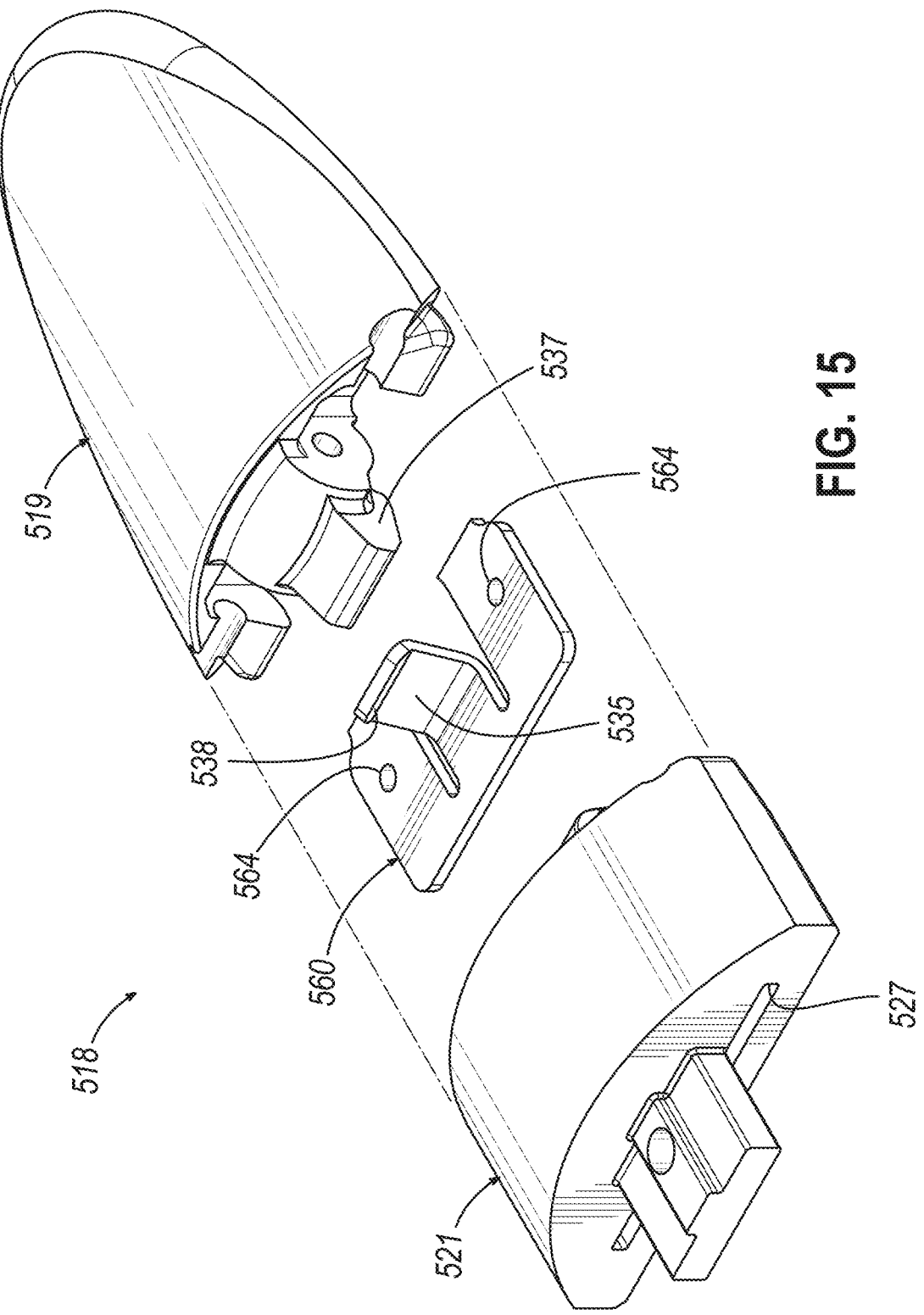
FIG. 15 depicts a distally facing upper exploded perspective view of the distal portion of the anvil jaw of FIG. 13, showing the distal tip, the connector, and the spring plate.
Figure 16:
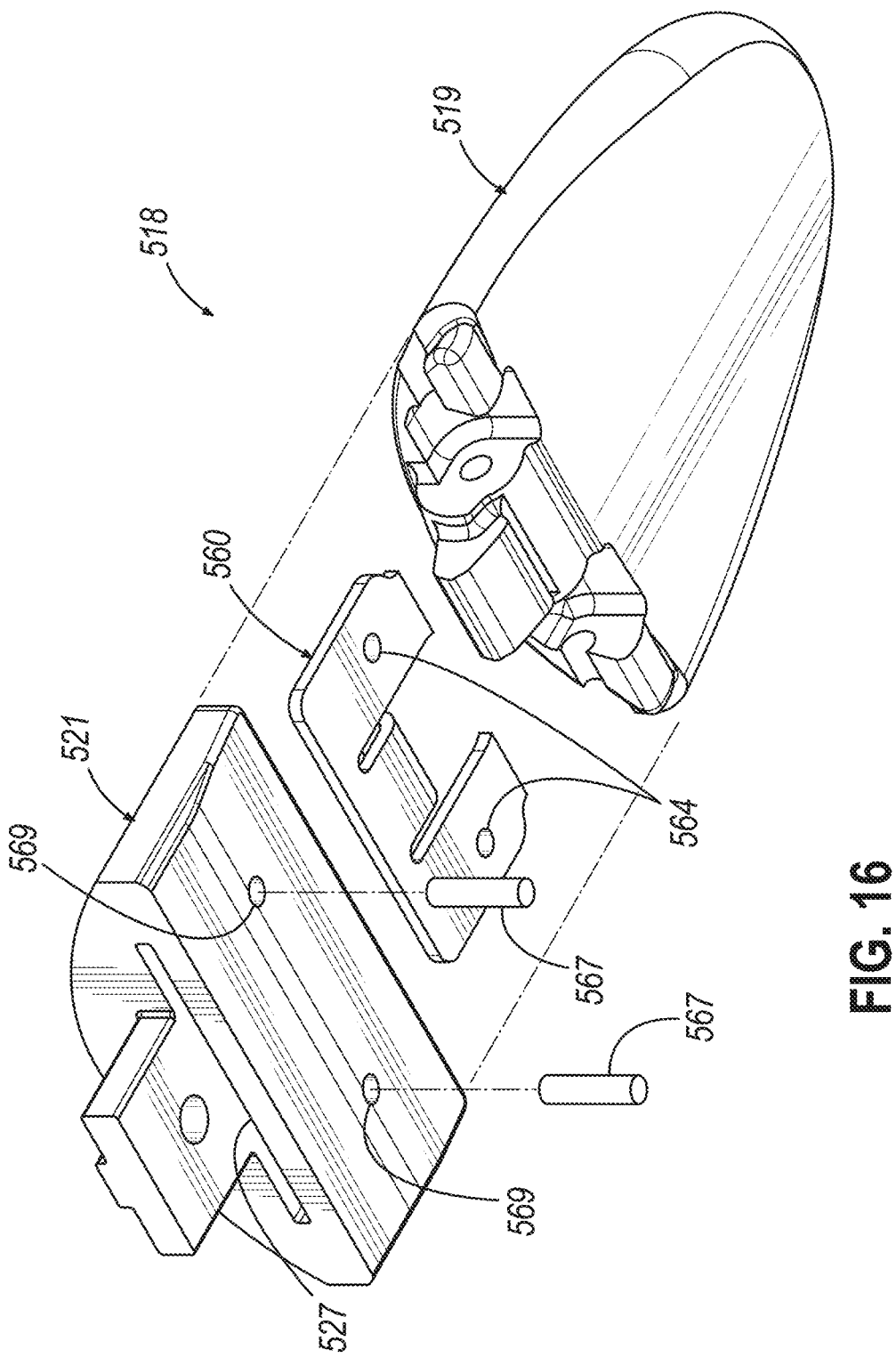
FIG. 16 depicts a distally facing lower exploded perspective view of the distal portion of the anvil jaw of FIG. 13, showing the distal tip, the connector, the spring plate, and two spring plate pins.

FIG. 12B shows another side view of an alternate end effector (412) similar to end effector (312) of FIG. 12A. With end effector (312), when anvil jaw (318) is in its angled and non-deformed state (as seen in phantom in the view of FIG. 12A), anvil jaw (318) extends to a point even with or proximal to the distal most end of cartridge (37). When anvil jaw (318) is deformed such that it is deflected upwardly, the end of distal tip (319) extends to a point just distal to the distal most end of cartridge (37). With end effector (412), as shown in FIG. 12B, when anvil jaw (318) is in its angled and non-deformed state (as seen in phantom in the view of FIG. 12B), anvil jaw (318) extends to a point even with or proximal to the distal most end of cartridge (37). When anvil jaw (318) is deformed such that it is deflected upwardly, the end of a distal tip (319) of anvil jaw (318) extends to a point even with or proximal to the distal most end of cartridge (37). In this manner, anvil jaw (318) of end effector (412) remains even with or proximal to the distal most end of cartridge (37) when anvil jaw (318) is in its angled state or deformed state such that anvil jaw (318) does not extend past the distal most end of cartridge (37) whether anvil jaw (318) is in its angled and non-deformed state or in its deformed state. In some instances, this can be achieved by modifying anvil jaw (318) such that distal tip (319) of anvil jaw is shortened in length. In other instances, instruments (10, 310) may be modified to provide for a slight proximal retraction of anvil jaw (318) when clamping. In view of the teachings herein, other ways to modify end effector (412) as it relates to control of anvil jaw (318) position, will be apparent to those of ordinary skill in the art.

IV. End Effector Jaws with Discretely Positionable Distal Tips

In some instances, it may be desirable to provide a clinician with a versatile end effector jaw having a distal tip that can assume multiple discrete positions relative to the jaw body to accommodate various needs during a surgical procedure. In that regard, it may be desirable to a user to have an end effector with an angled (or "bent") distal tip that provides visualization and placement benefits as described above, or that more effectively urges tissue (e.g., a large vessel) proximally into the space between the anvil jaw and the cartridge jaw as the end effector closes. In other circumstances, it may be desirable to a user to use an end effector with a substantially straight distal tip to better facilitate marching as described above, or to reduce the pressure exerted on tissue positioned under the distal tip.

Each of the illustrative end effector jaws described below in connection with FIGS. 13-42B is configured for use with any of the surgical stapling instruments described herein and includes a distal tip configured to move (e.g., pivot or rotate) relative to the jaw body between a first discrete position and a second discrete position to adjust an orientation of the longitudinal distal tip axis relative to the longitudinal jaw body axis, and maintain that discrete. Transition between such discrete positions occurs in response to an external input force intentionally applied to the distal tip by the clinician directly or indirectly via patient anatomy in contact with the distal tip. Additionally, each end effector jaw is suitably configured such that its distal tip will maintain its current discrete position until acted upon by an external input force intentionally applied to the distal tip by the clinician, directly or indirectly.

While such end effector jaws of the present versions are shown in the form of anvil jaws each having an anvil jaw body with a plurality of staple forming pockets, in other versions such discretely positionable distal tips may be applied to a cartridge jaw that is configured to receive a replaceable staple cartridge or otherwise support a stapling assembly that houses a plurality of staples. Additionally, while the first discrete position of each end effector jaw described below is presented in the form of a straight position in which the distal tip axis extends substantially parallel to the jaw body axis, in other versions the first discrete position may include an angled position in which the distal tip axis is angled relative to the jaw body axis, for example in a direction away from the opposing end effector jaw. Additionally, in other versions the end effector jaws may include more than two discrete positions for their distal tips.

The term "discrete" and variations thereof as used herein in connection with the discretely positionable distal tips shown in FIGS. 13-42B means predefined, where each discrete position of a distal tip relative to its respective jaw body is predefined by specific structural features of the distal tip (519) and/or other portions of the respective end effector jaw. "Discrete" and variations thereof as used herein are not intended to encompass configurations in which a distal tip is configured to transition between various positions relative to a respective jaw body purely by elastic or plastic deformation of the distal tip.

A. Anvil Jaw Having Spring Plate and Toggle Tip with Pinned Hinge

FIGS. 13-17C depict a distal portion of a illustrative anvil jaw (518) having a discretely positionable distal tip (519) and configured for use with an endoscopic surgical stapler end effector, such as any of end effectors (12, 212, 312, 412) described above.

Anvil jaw (518) includes an elongate jaw body (520) having a stapling surface with a plurality of staple forming pockets similar to pockets (53), a distal tip (519) located distal to jaw body (520), a connector (521) that interconnects distal tip (519) with jaw body (520), and a spring plate (560) housed within connector (521). As described in greater detail below, connector (521) is affixed to a distal end of jaw body (520), and distal tip (519) is pivotably coupled with connector (521) and is configured to pivot relative to jaw body (520) between a first discrete position to assume a straight tip orientation (see FIG. 17A), and a second discrete position to assume an angled tip orientation (see FIG. 17C). In the present version, connector (521) is configured to be press-fit to jaw body (520). In particular, connector (521) includes a proximal protrusion (541) that inserts into a slot (542) formed in the distal end of jaw body (520), and this connection is then pinned using a pin (536). Other ways of attaching connector (521) with jaw body (520) of anvil jaw (518) will be apparent to those of ordinary skill in the art. In other versions of anvil jaw (518), the features of connector (521) may be integrally formed with jaw body (520) so as to define an integral connector portion at the distal end of jaw body (520), as noted below.

Figure 17A:
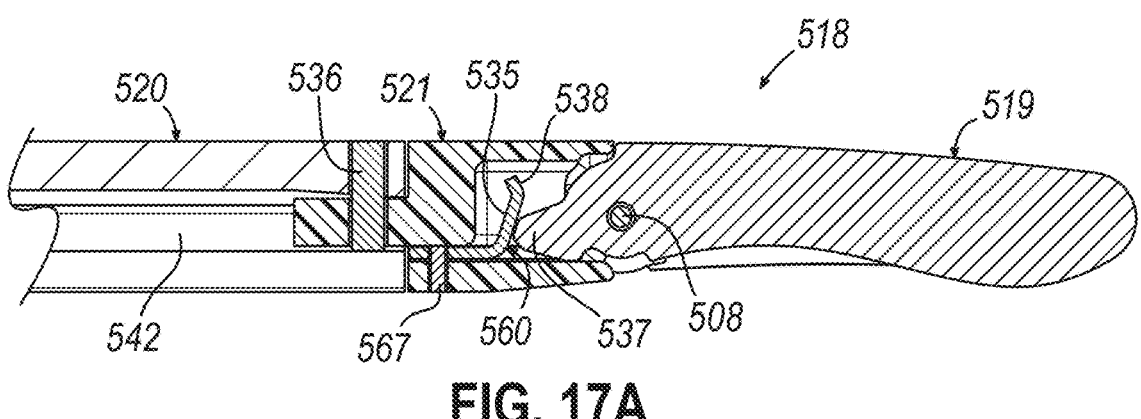
FIG. 17A depicts a side cross-sectional view of the distal portion of the anvil jaw of FIG. 13, taken along line 17-17 of FIG. 13, showing the tip in a first discrete position.

Connector (521) includes a pair of arms (529) that extend distally. Arms (529) include bores (531) that are configured to align coaxially with a corresponding bore formed in a proximal end portion of distal tip (519) to receive a pivot pin (508) and thereby pivotably couple distal tip (519) with connector (521). In this manner, bores (531) and pivot pin (508) define a longitudinally fixed pivot axis, or axis of rotation, about which distal tip (519) is configured to pivot (or "toggle") between the first and second discrete positions, and which extends transversely relative to a longitudinal axis of jaw body (520). In some alternative versions, the pivot axis may be permitted to slidably translate longitudinally by a minimal distance before, during, or after pivotal motion about the pivot axis, for example by providing bores (531) of connector (521) or the bore of distal tip (519) with an elongate cross-sectional shape rather than a circular cross-sectional shape. It will be appreciated that a similar modification may be applied to anvil jaws (618, 718) described below as well. As seen in FIGS. 17A and 17C, distal tip (519) may be constrained from pivoting beyond a particular angle due to interference between connector (521) and a tapered detent projection (537) extending proximally from a body of distal tip (519). Pivot pin (508) may be press fit, threaded, or glued, for example, to either connector (521) or distal tip (519) and, in some versions, may be removable.

Connector (521) further includes a longitudinally extending slot (527) (which may also be referred to as a cavity) that houses and restrains spring plate (560). Spring plate (560) may include spring plate holes (564) for removably securing spring plate (560) to connector (521). Spring plate (560) may include a spring (535), shown as a leaf spring tab, which may apply a biasing force to detent projection (537) of distal tip (519) and thereby pivotably bias distal tip (519) toward one of the first or second discrete positions. More specifically, spring (535) may include a distal bend (538) configured to contact and apply a force to detent projection (537) of distal tip (519). Spring plate (560) may be made of material capable of deflecting and applying a spring force such as metal or plastic. Additionally, spring plate (560) may be removably or non-removably attached to connector (521). Spring plate (560) may be coupled to connector (521) using with a pair of spring plate pins (567) extending through a pair of connector pin holes (569) and spring plate holes (564). Spring plate pins (567) may be secured to connector (521) by threads, adhesive, or press fitting, for example.

Figure 17B:
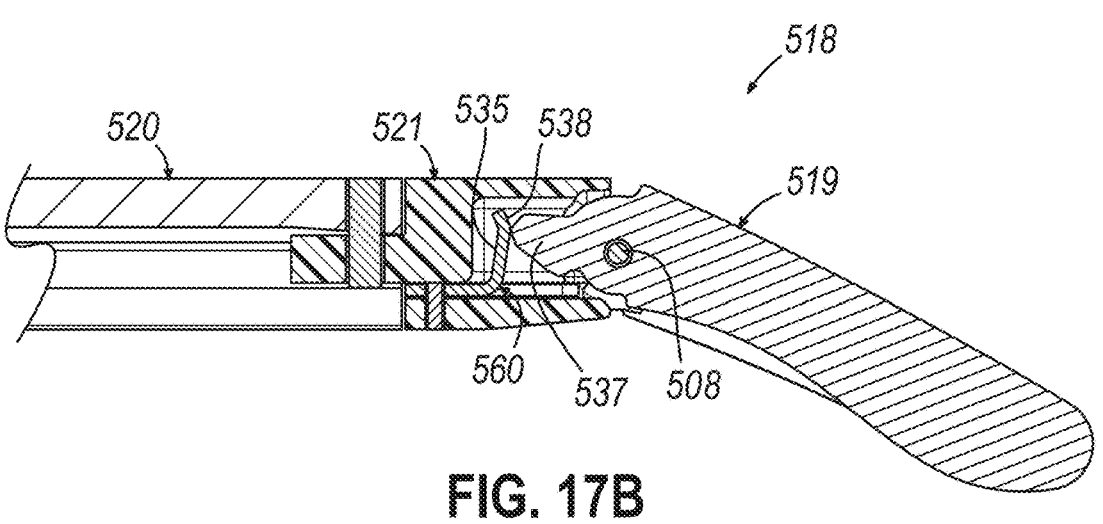
FIG. 17B depicts another side cross-sectional view of the distal portion of the anvil jaw of FIG. 13, taken along line 17-17 of FIG. 13, showing the tip transitioning to a second discrete position.
Figure 17C:
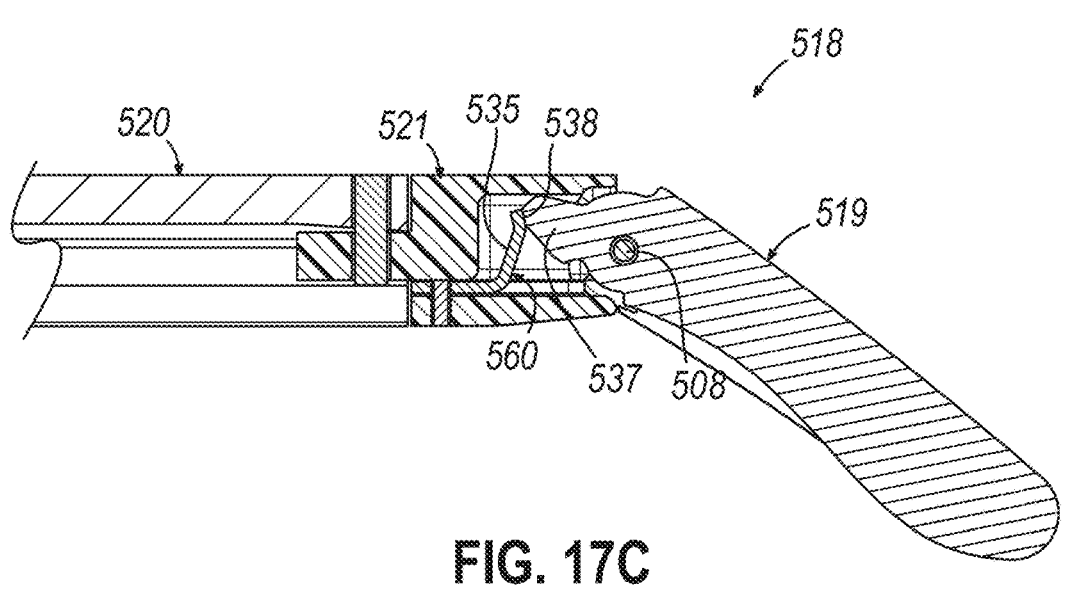
FIG. 17C depicts another side cross-sectional view of the distal portion of the anvil jaw of FIG. 13, taken along line 17-17 of FIG. 13, showing the tip in the second discrete position.
Figure 18:
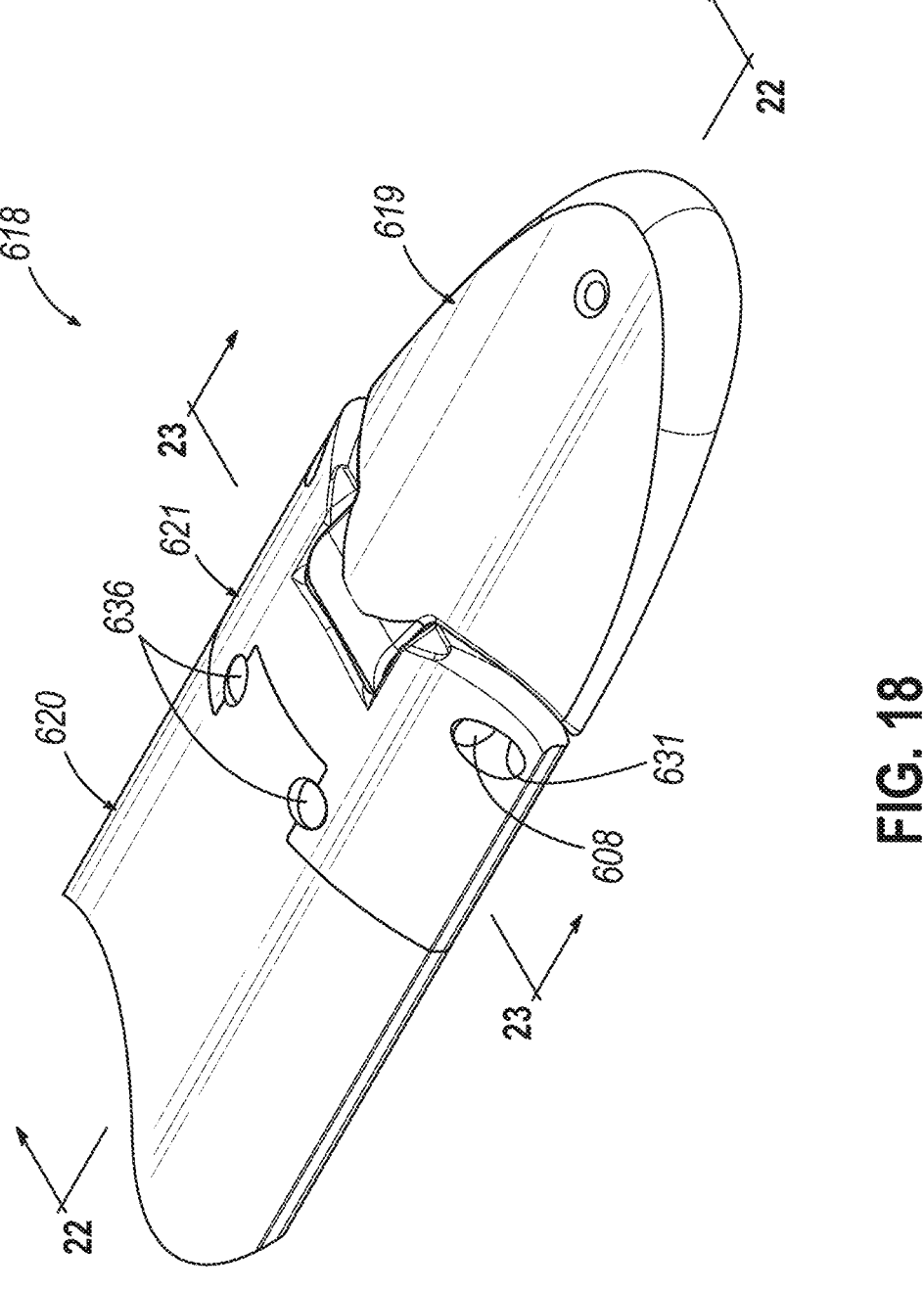
FIG. 18 depicts a perspective view of a distal portion of another anvil jaw configured for use with the surgical instruments described herein.

As shown in FIGS. 17A-17C, and as noted above, distal tip (519) is configured to pivot relative to jaw body (520) and connector (521) via pivot pin (508) between first and second discrete positions that define respective first and second orientations of distal tip (519). For instance, as shown in FIG. 17A, illustrating distal tip (519) in a first discrete position, distal tip (519) is in a straight orientation in which a longitudinal axis of distal tip (519) is substantially parallel with a longitudinal axis of jaw body (520). In the illustrated version, this corresponds to when detent projection (537) of distal tip (519) is located below distal bend (538) of spring tab (535). As shown in FIG. 17C, illustrating distal tip (519) in a second discrete position, distal tip (519) is in a bent or angled orientation in which the longitudinal axis of distal tip (519) is angled relative to the longitudinal axis of jaw body (520). In the illustrated version, this corresponds to when detent projection (537) of distal tip (519) is located above distal bend (538) of spring (535). FIG. 17B illustrates distal tip (519) in transition from the first discrete position to the second discrete position such that detent projection (537) is in contact with distal bend (538) of spring (535) of spring plate (560).

Detent projection (537) of distal tip (519) may remain in continuous contact with spring (535) within connector slot (527) such that spring (535) is continuously in at least a slightly proximally-deflected state. This interaction may cause spring (535) to continuously exert a distally directed bias force on detent projection (537), which may peak as detent projection (537) approaches distal bend (538) when distal tip (519) is rotated. When detent projection (537) is located at or below distal bend (538), spring (535) may rotatably bias detent projection (537) downwardly so that distal tip (519) assumes the first discrete position and corresponding straight tip orientation of FIG. 17A. When detent projection (537) is located at or above distal bend (538), spring (535) may rotatably bias detent projection (537) upwardly so that distal tip (519) assumes the second discrete position and corresponding angled tip orientation of FIG. 17C. In this regard, distal bend (538) may function as a fulcrum feature. The size and shape of spring (535) and detent projection (537) may be selected to achieve a desired biasing effect on distal tip (519).

In the present example, detent projection (537) acts with spring (535) to hold distal tip (519) in its current discrete position until a sufficient force is applied to distal tip (519) to overcome the bias force exerted between detent projection (537) and spring (535). For instance, when distal tip (519) is in the angled orientation and a sufficient upward force is applied to distal tip (519), detent projection (537) of distal tip (519) will rotate downward and click past spring bend (538), allowing distal tip (519) to adopt the other discrete position. Similarly, when distal tip (519) is in the straight orientation and a sufficient downward force is applied to distal tip (519), detent projection (537) of distal tip (519) will rotate upward and click past spring bend (538), allowing distal tip (519) to adopt the other discrete position.

As also seen in FIGS. 15-17C, a proximal end of distal tip (519) includes stop surfaces configured to engage respective distal end surfaces of connector (521) to constrain distal tip (519) to a predefined range of angular motion relative to jaw body (720). In particular, as shown in FIG. 17A an upper stop surface at an upper end of a base of detent projection (537) is configured to engage an upper distal end surface of connector (521) when distal tip (519) is in the first discrete position to inhibit distal tip (519) from pivoting further beyond the first discrete position. Additionally, as shown in FIG. 17C, a lower stop surface at a lower end of the base of detent projection is configured to engage a lower distal end surface of connector (521) when distal tip (519) is in the second discrete position to inhibit distal tip (519) from pivoting further beyond the second discrete position.

B. Anvil Jaw Having Toggle Tip and Resilient Detent Connector

FIGS. 18-23C depict a distal portion of another illustrative anvil jaw (618) having a discretely positionable distal tip (619) and configured for use with an endoscopic surgical stapler end effector, such as any of end effectors (12, 212, 312, 412) described above.

Figure 19:
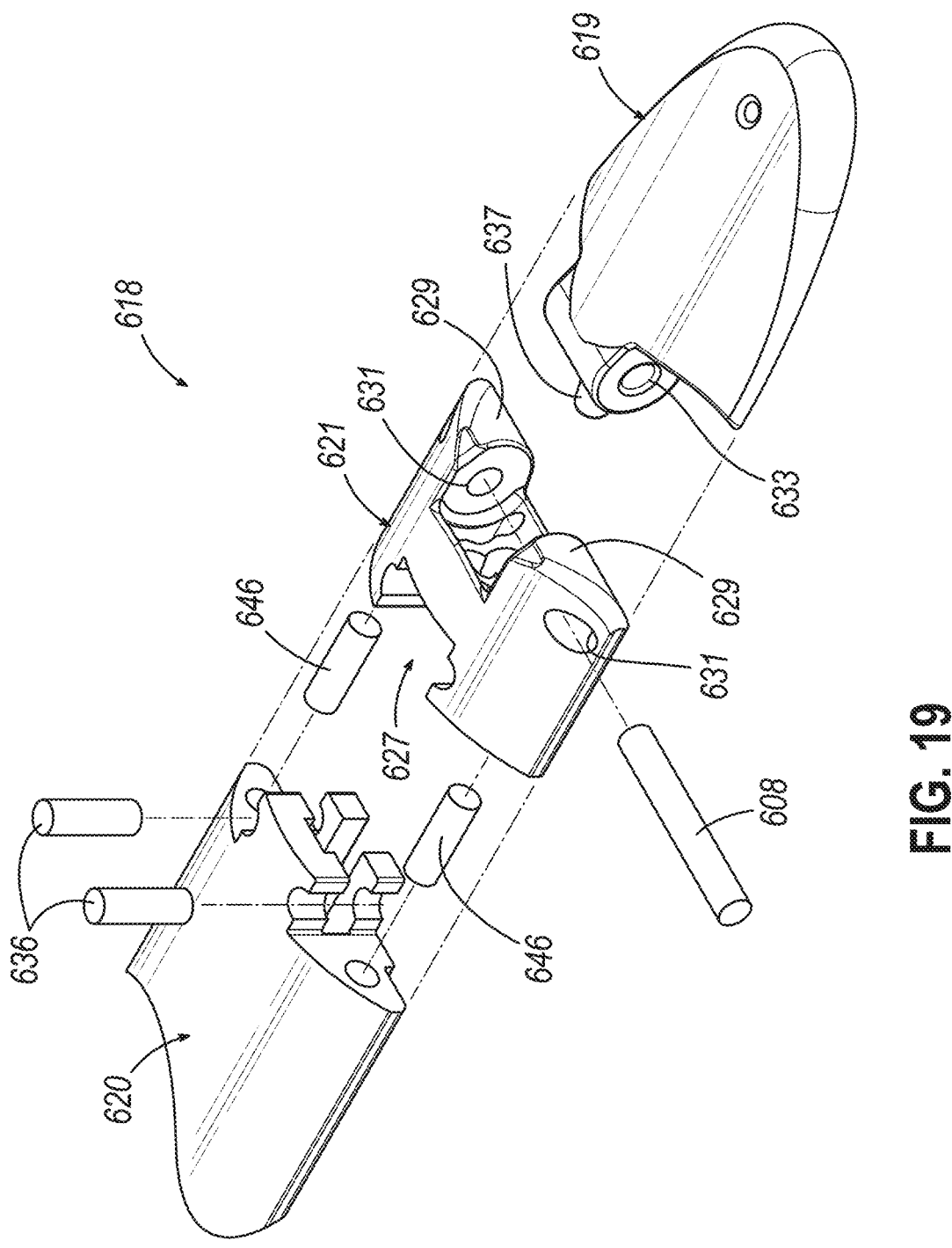
FIG. 19 depicts a proximally facing upper exploded perspective view of the distal portion of the anvil jaw of FIG. 18, showing an anvil body, a distal tip, a connector, two guide pins, a pivot pin, and two connector pins.
Figure 20:
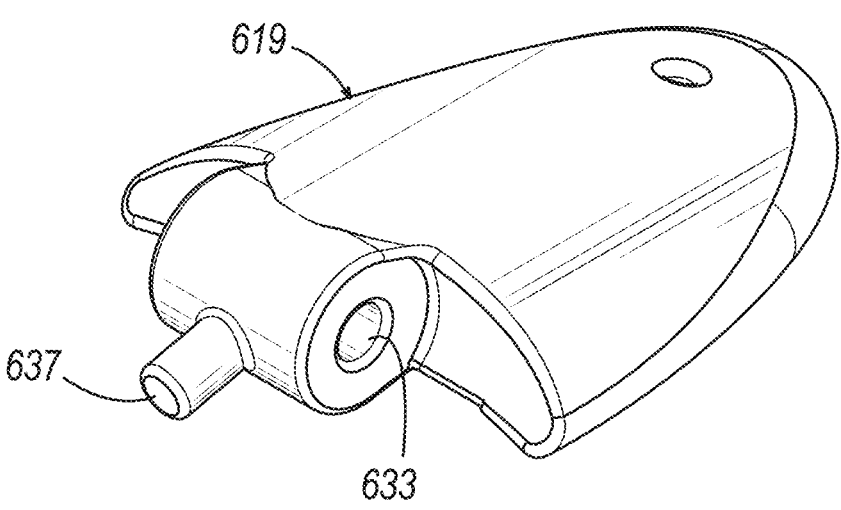
FIG. 20 depicts a distally facing perspective view of the distal tip of FIG. 18.
Figure 21:
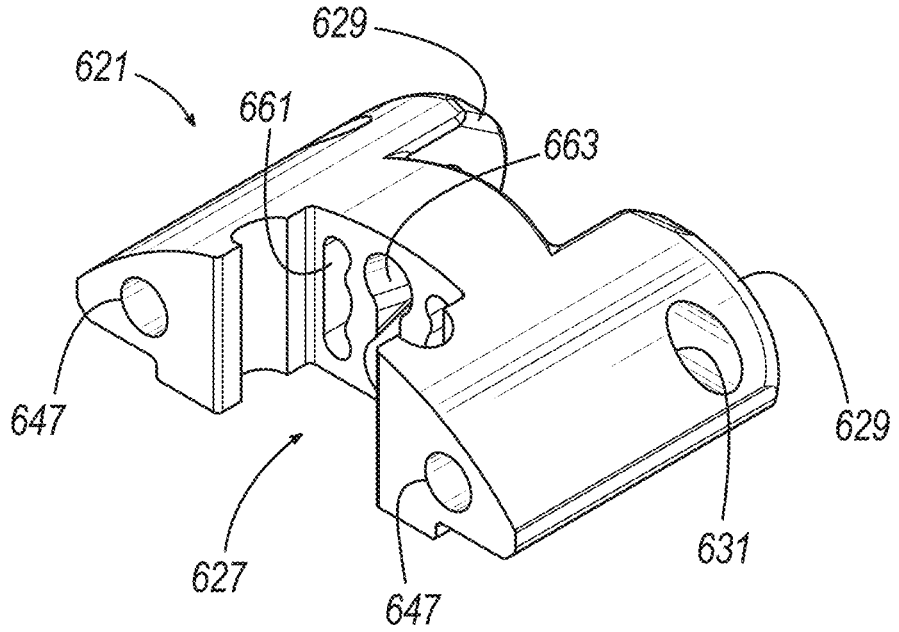
FIG. 21 depicts a distally facing perspective view of the base of FIG. 18.

Anvil jaw (618) includes an elongate jaw body (620) having a stapling surface with a plurality of staple forming pockets, similar to pockets (53), a distal tip (619) located distal to jaw body (620), and a connector (621) that interconnects distal tip (619) with jaw body (620). Similar to distal tip (519), distal tip (619) is pivotably coupled with connector (621) and is configured to pivot relative to jaw body (620) between a first discrete position to assume a straight tip orientation (see FIG. 22A), and a second discrete position to assume an angled tip orientation (see FIG. 22B). Connector (621) is affixed to a distal end of jaw body (620), for example with a plurality of pins. In present version, connector (621) is affixed with a pair of pins (646) positioned within corresponding pin holes (647) to retain connector (621) in lateral alignment with jaw body (620), and with a pair of pins (636) to secure connector (621) longitudinally relative to jaw body (620). Pins (636, 646) may be secured by press fit or threading, for example. As shown in FIG. 19, a proximal end of connector (621) includes a vertically extending slot (627) sized and shaped to receive a pair of protrusions extending distally from the distal end of jaw body (620) when connector (621) is assembled with jaw body (620).

A distal end of connector (621) includes a pair of arms (629) that extend distally and include respective bores (631) configured to receive a pivot pin (608) to pivotably couple distal tip (619) with connector (621). In this manner, bores (631) and pivot pin (608) define a longitudinally fixed pivot axis, or axis of rotation, about which distal tip (619) is configured to pivot (or "toggle") between the first and second discrete positions, and which extends transversely relative to a longitudinal axis of jaw body (620). In some alternative versions, the pivot axis may be permitted to slidably translate longitudinally by a minimal distance before, during, or after pivotal motion about the pivot axis. A proximal end of distal tip (619) includes a tip hole (633) that aligns coaxially with bores (631) and likewise receives pivot pin (608). Pivot pin (608) may be press fit, threaded, or glued, for example, to either connector (621) or distal tip (619) and, in some versions, may be removable.

Figure 22A:
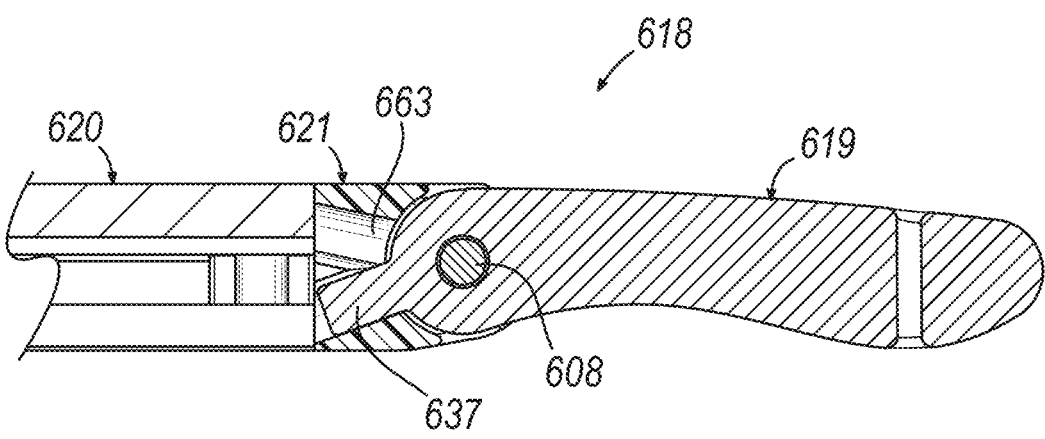
FIG. 22A depicts a side cross-sectional view of the distal portion of the anvil jaw of FIG. 18, taken along line 22-22 of FIG. 18, showing the distal tip in a first discrete position.
Figure 22B:
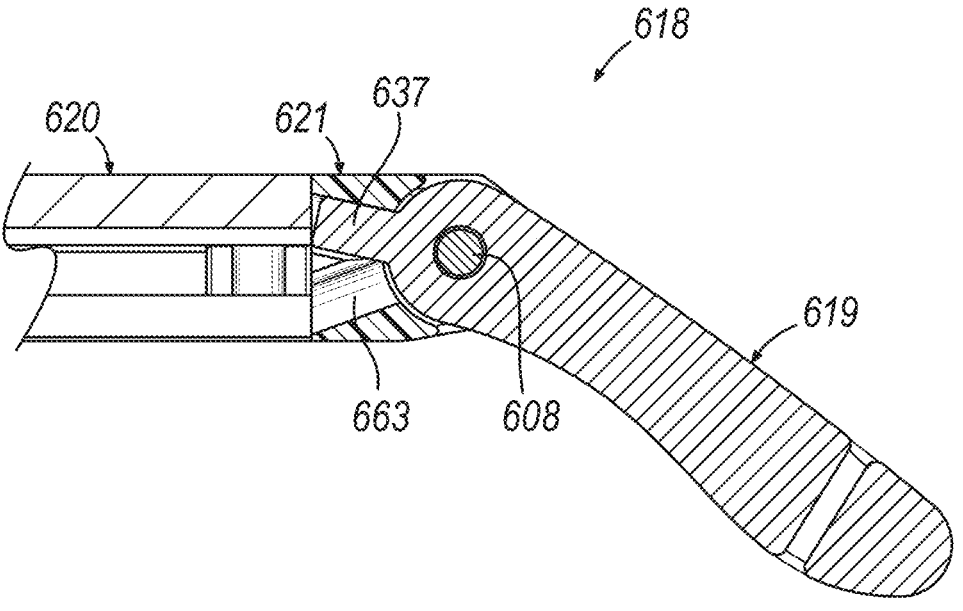
FIG. 22B depicts another side cross-sectional view of the distal portion of the anvil jaw of FIG. 18, taken along line 22-22 of FIG. 18, showing the distal tip in a second discrete position.

A central body portion of connector (621) includes a detent cavity (663) that extends longitudinally through the central body portion and is located proximal to arm bores (631). As described below, connector (621) as a whole or at least the central body portion of connector (621) that includes detent cavity (663) is formed of an elastically deformable material configured to releasably retain distal tip (619) in each of its first and second discrete positions. Detent cavity (663) is defined by two interconnected, vertically adjacent openings that define an upper cavity portion and a lower cavity portion, respectively, each extending longitudinally along a respective longitudinal axis. As shown in FIGS. 22A-22B, these longitudinal axes are angled relative to one another so as to define a proximally opening angle. The opening defining each cavity portion of detent cavity (663) is sized to receive a pin-like detent projection (637) that extends proximally from a proximal end of distal tip (619). A medial cavity portion of detent cavity (663) interconnects the upper and lower cavity portions and has a maximum transverse width that is narrower than a maximum transverse width of each of the upper cavity portion, the lower cavity portion, and detent projection (637) of distal tip (619). In the present version, detent projection (637) is substantially cylindrical and each opening defining the upper and lower portions of detent cavity (663) has a stadium shape with a length aligned with a length of detent cavity (663) along a vertical thickness of connector (621).

Detent projection (637) is positionable within the lower cavity portion (i.e., the lower opening) of detent cavity (663) to releasably retain distal tip (619) in the first discrete position and corresponding straight tip orientation. Conversely, detent projection (637) is positionable within the upper cavity portion (i.e., the upper opening) to releasably retain distal tip (619) in the second discrete position and corresponding angled tip orientation. Additionally, at least the central body portion of connector (621) is formed of a polymer configured to elastically deflect and thereby permit passage of detent projection (637) of distal tip (619) between the upper and lower cavity portions in response to an external input force applied to distal tip (619). The reduced transverse width of the medial cavity portion provides an interference fit with detent projection (637) and thus serves to inhibit detent projection (637) from transitioning between the upper and lower cavity portions in the absence of the external input force. Additionally, detent cavity (663) includes tapered edges at the medial cavity portion that bias detent projection (637) toward the closer of either of the upper cavity portion or the lower cavity portion, thereby biasing distal tip (619) toward the closer of either the first discrete position or the second discrete position. Connector (621) further includes a relief groove (661) that extends vertically along each lateral side of detent cavity (663). Each relief groove (661) enables a corresponding wall of material that separates the relief groove (661) from detent cavity (663) to resiliently deflect laterally outwardly when detent projection (637) transitions between the upper and lower cavity portions. Each relief groove (661) is shown in the form of an elongate through hole though may be configured in various other ways in other versions of connector (621).

Figure 23A:
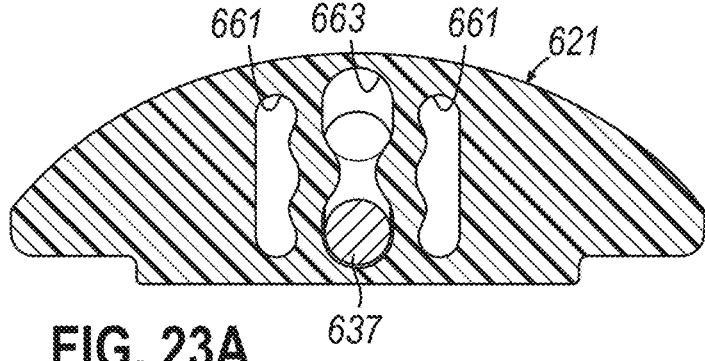
FIG. 23A depicts a distally facing cross-sectional view of the distal portion of the anvil jaw of FIG. 18, taken along line 23-23 of FIG. 18, showing the distal tip in the first discrete position of FIG. 22A.
Figure 23B:
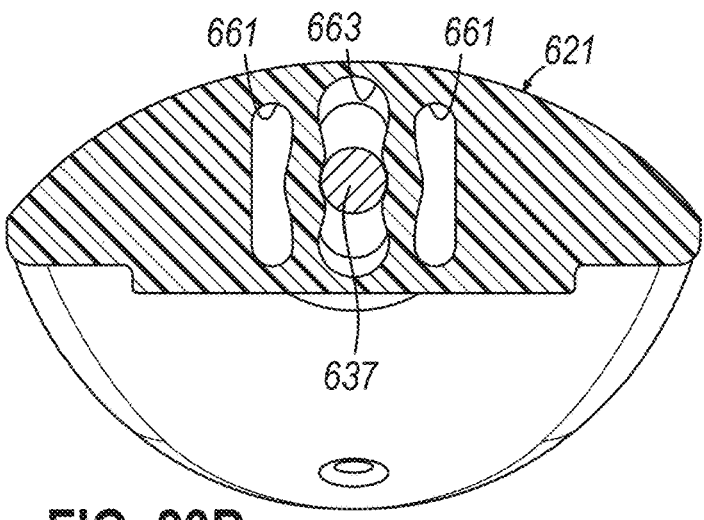
FIG. 23B depicts another distally facing cross-sectional view of the distal portion of the anvil jaw of FIG. 18, taken along line 23-23 of FIG. 18, showing the distal tip between the first discrete position of FIG. 22A and the second discrete position of FIG. 22B.
Figure 23C:
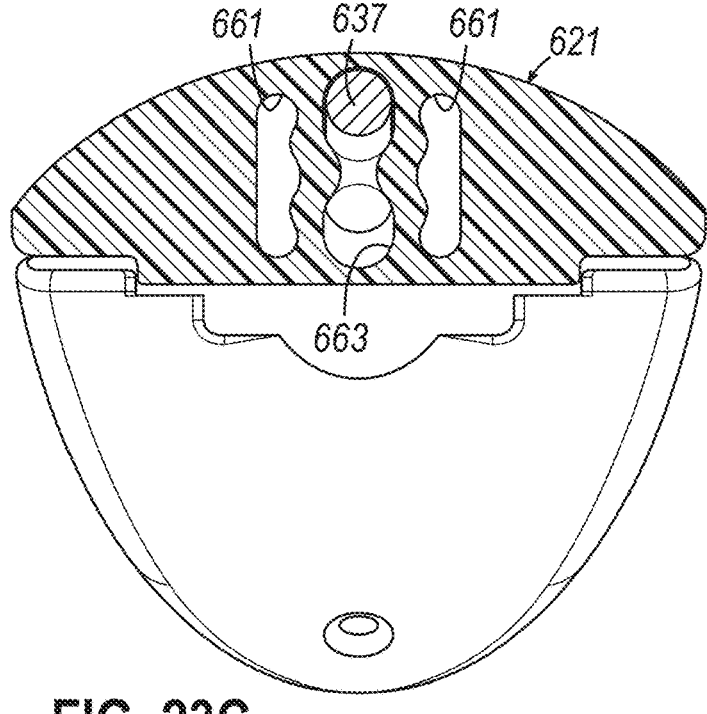
FIG. 23C depicts another distally facing cross-sectional view of the distal portion of the anvil jaw of FIG. 18, taken along line 23-23 of FIG. 18, showing the distal tip in the second discrete position of FIG. 22B.
Figure 24:
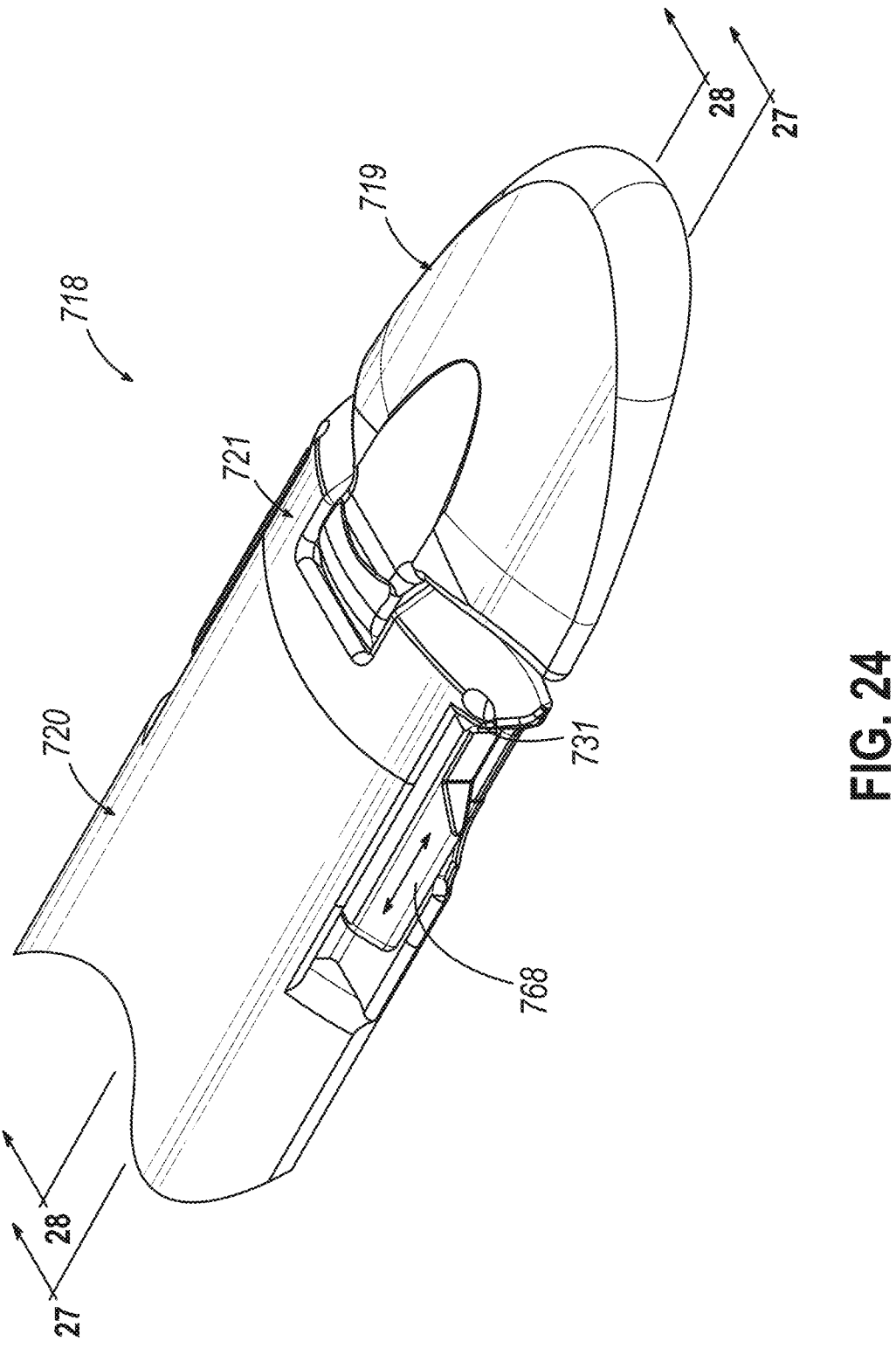
FIG. 24 depicts a perspective view of a distal portion of another anvil jaw configured for use with the surgical instruments described herein.

Distal tip (619) is configured to pivot about its pivot axis between discrete positions relative to jaw body (620), wherein the discrete positions are defined by the lower and upper portions of detent cavity (663). In particular, FIGS. 22A and 23A show distal tip (619) in the first discrete position in which distal tip (619) assumes a straight orientation relative to jaw body (620) such that the distal tip axis is substantially parallel to the jaw body axis. This tip position is achieved by positioning detent projection (637) of distal tip (619) within the lower cavity portion of detent cavity (663). FIGS. 22B and 23C show distal tip (619) in the second discrete position in which distal tip (619) assumes an angled orientation relative to jaw body (620) such that the distal tip axis is angled relative to the jaw body axis. This tip position is achieved by positioning detent projection (637) within the upper cavity portion of detent cavity (663). FIG. 23B shows detent projection (637) of distal tip (619) transitioning between the lower and upper cavity portions of detent cavity (663), which results in laterally outward deflection of the walls of material described above into relief grooves (661). Once the detent projection (637) has been driven into the lower or upper cavity portion of detent cavity (663) to provide distal tip (619) in the corresponding first or second discrete position, detent projection (637) remains there until an external input force is applied by a user or external structure to distal tip (619) to drive distal tip (619) to the opposing discrete position.

C. Anvil Jaw Having Pin-Lock Tip

FIGS. 24-28B depict a distal portion of another illustrative anvil jaw (718) having a discretely positionable distal tip (719) and configured for use with an endoscopic surgical stapler end effector, such as any of end effectors (12, 212, 312, 412) described above.

Anvil jaw (718) includes an elongate jaw body (720) having a stapling surface with a plurality of staple forming pockets similar to pockets (53), a distal tip (719) located distal to jaw body (720), a connector (721) that interconnects distal tip (719) with jaw body (720), and a movable latch exemplified as a slider (768) movably coupled with jaw body (720) and connector (721). Connector (721) is coupled to jaw body (720) with pins (746) positioned within respective pin holes (747). Pins (746) may be secured via press fit or threads, for example, though various other ways of attaching connector (721) with jaw body (720) will be apparent to those of ordinary skill in the art.

Jaw body (720) further includes a slider slot (724) that slidably houses slider (768) and permits slider (768) to translate relative to jaw body (720) between a distal lock position and a proximal release position. Slider (768) may be resiliently biased toward the distal lock position, and selectably retracted to the proximal release position by a user gripping exposed side portions of slider (768). Slider (768) includes a pair of latch projections shown as pins (781), which are configured to extend distally through a corresponding pair of traverse holes (789) of connector (721) and into either a pair of first latch pin bores (785) or a pair of second latch pin bores (784) formed in a proximal end (737) of distal tip (719). Slider (768) is laterally relative to jaw body (720) and connector (721) by a pair of laterally opposed guide rails that slidably track within respective longitudinal channels defined by the distal end of jaw body (720) in combination with connector (721).

Connector (721) includes a pair of arms (729) that extend distally and include bores (731) configured to receive a pivot pin (708) to pivotably couple distal tip (719) with connector (721). In this manner, bores (731) provide a longitudinally fixed pivot axis, or axis of rotation, for distal tip (719). In some alternative versions, the pivot axis may be permitted to slidably translate longitudinally by a minimal distance before, during, or after pivotal motion about the pivot axis. Pivot pin (708) may be press fit, threaded, or glued, for example, to either connector (721) or distal tip (719) and, in some versions, may be removable.

Figure 27A:
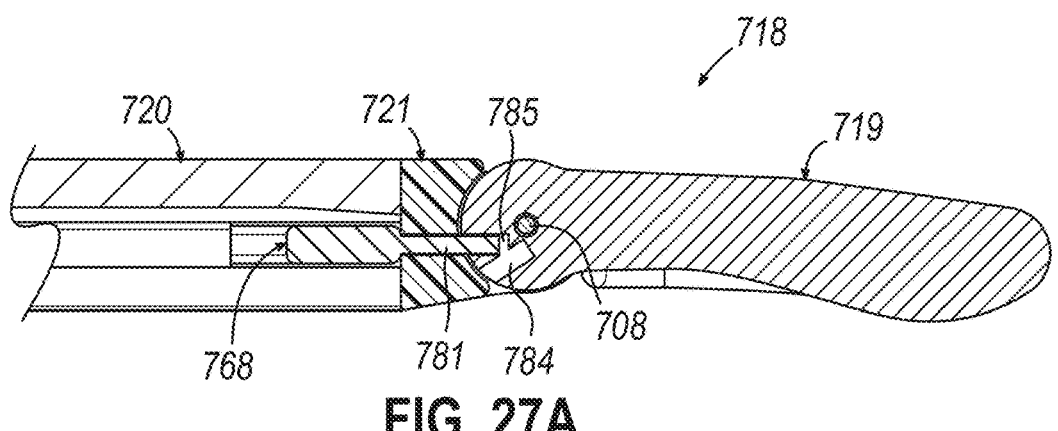
FIG. 27A depicts a side cross-sectional view of the distal portion of the anvil jaw of FIG. 24, taken along line 27-27 of FIG. 24, showing the distal tip in a first discrete position.
Figure 27B:
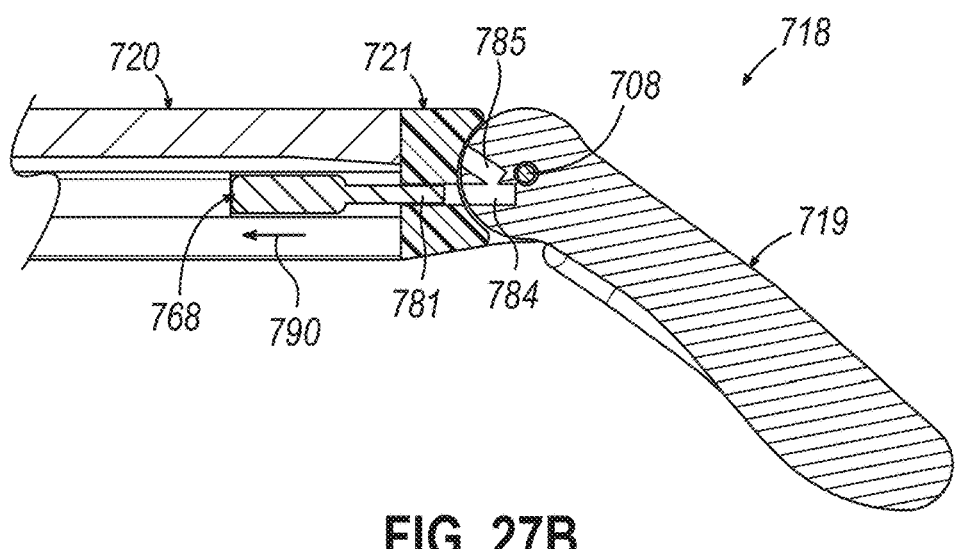
FIG. 27B depicts a side cross-sectional view of a distal portion of the anvil jaw of FIG. 24, taken along line 27-27 of FIG. 24, showing the distal tip between the first discrete position and a second discrete position.
Figure 27C:
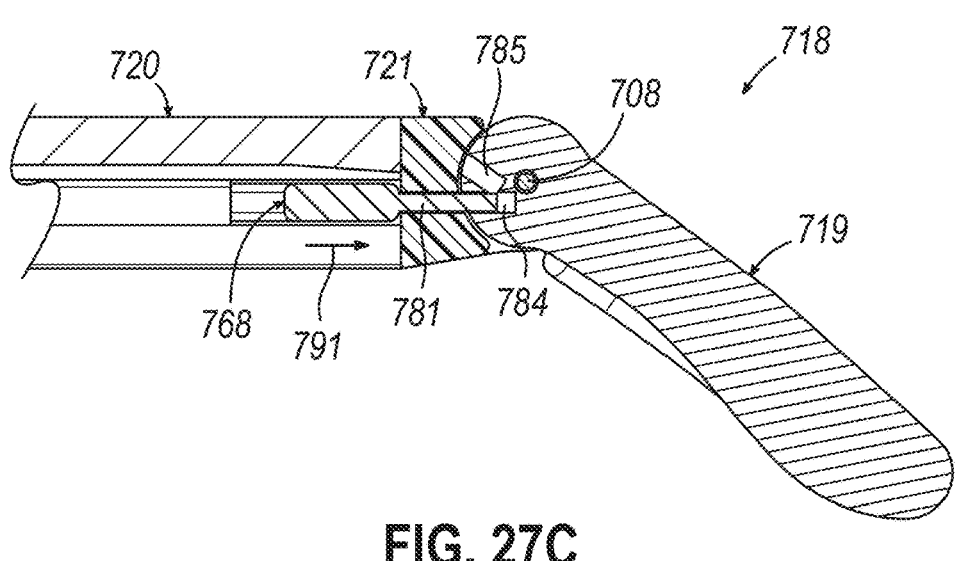
FIG. 27C depicts a side cross-sectional view of the distal portion of the anvil jaw of FIG. 24, taken along line 27-27 of FIG. 24, showing the distal tip in the second discrete position.
Figure 28A:
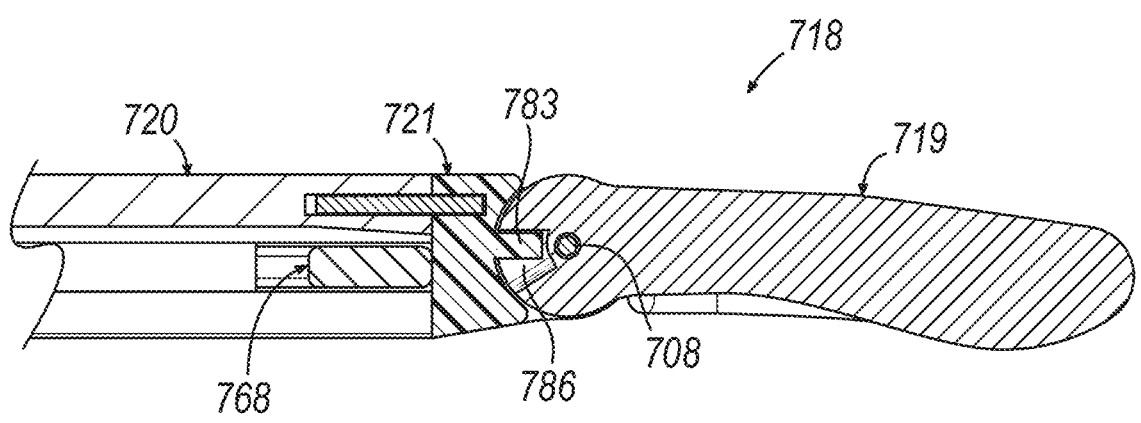
FIG. 28A depicts a side cross-sectional view of the distal portion of the anvil jaw of FIG. 24, taken along line 28-28 of FIG. 24, showing the distal tip in the first discrete position.
Figure 28B:
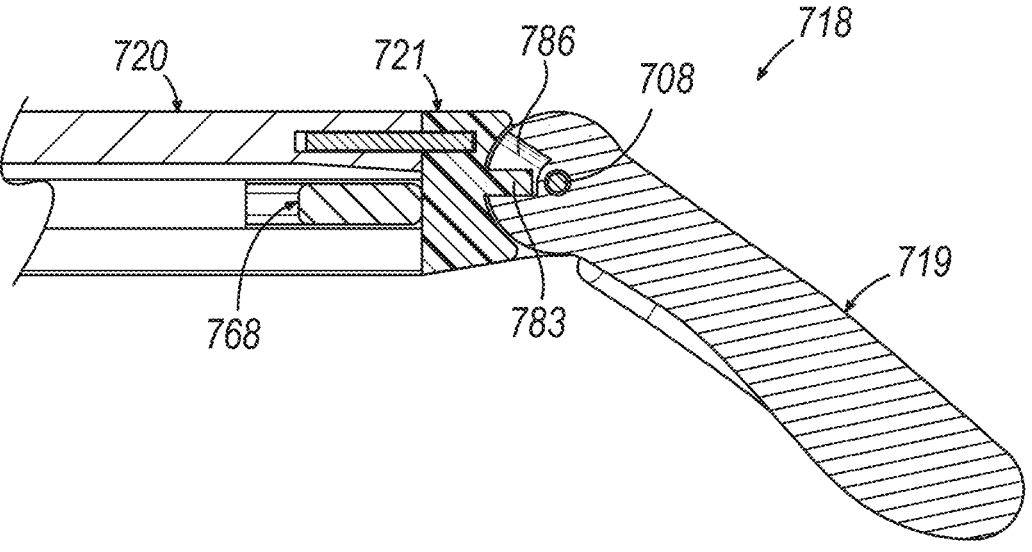
FIG. 28B depicts a side cross-sectional view of the distal portion of the anvil jaw of FIG. 24, taken along line 28-28 of FIG. 24, showing the distal tip in the second discrete position.

First latch pin bores (785) and second latch pin bores (784) open through a convexly curved proximal end surface of distal tip (719). As shown in FIGS. 27A-27C, each first latch pin bore (785) is angled relative to a corresponding second latch pin bore (784) such that each vertically adjacent pair of first and second latch pin bores (785, 784) defines a proximally opening angle and communicate at their distal ends. In other versions of distal tip (719), various alternative quantities and configurations of latch bores may be provided, where each pair of latch bores defines a respective discrete position of distal tip (719) when engaged by latch pins (781).

With the above configuration for anvil jaw (718), distal tip (719) is configured to pivot about the pivot axis defined by bores (731) to adopt at least first and second discrete positions relative to jaw body (720). FIG. 27A shows distal tip (719) in a first discrete position in which a longitudinal axis of distal tip (719) is substantially parallel to a longitudinal axis of jaw body (720), where this first discrete position is maintained by distal insertion of latch pins (781) into first latch pin bores (785). FIGS. 27B and 27C show distal tip (719) in a second discrete position in which the longitudinal axis of distal tip (719) is angled relative to the longitudinal axis of jaw body (720), where this second discrete position is maintained by distal insertion of latch pins (781) into second latch pin bores (784). As shown in FIGS. 27B-27C, slider (768) is actuatable in a proximal direction (790) to retract latch pins (781) from latch pin bores (784, 785) and thereby permit distal tip (719) to freely pivot relative to connector (721) and jaw body (720); and in a distal direction (791) to insert latch pins (781) into one of first latch pin bores (785) or second latch pin bores (784) to releasably lock distal tip (719) in one of the first discrete position or the second discrete position.

Figure 25:
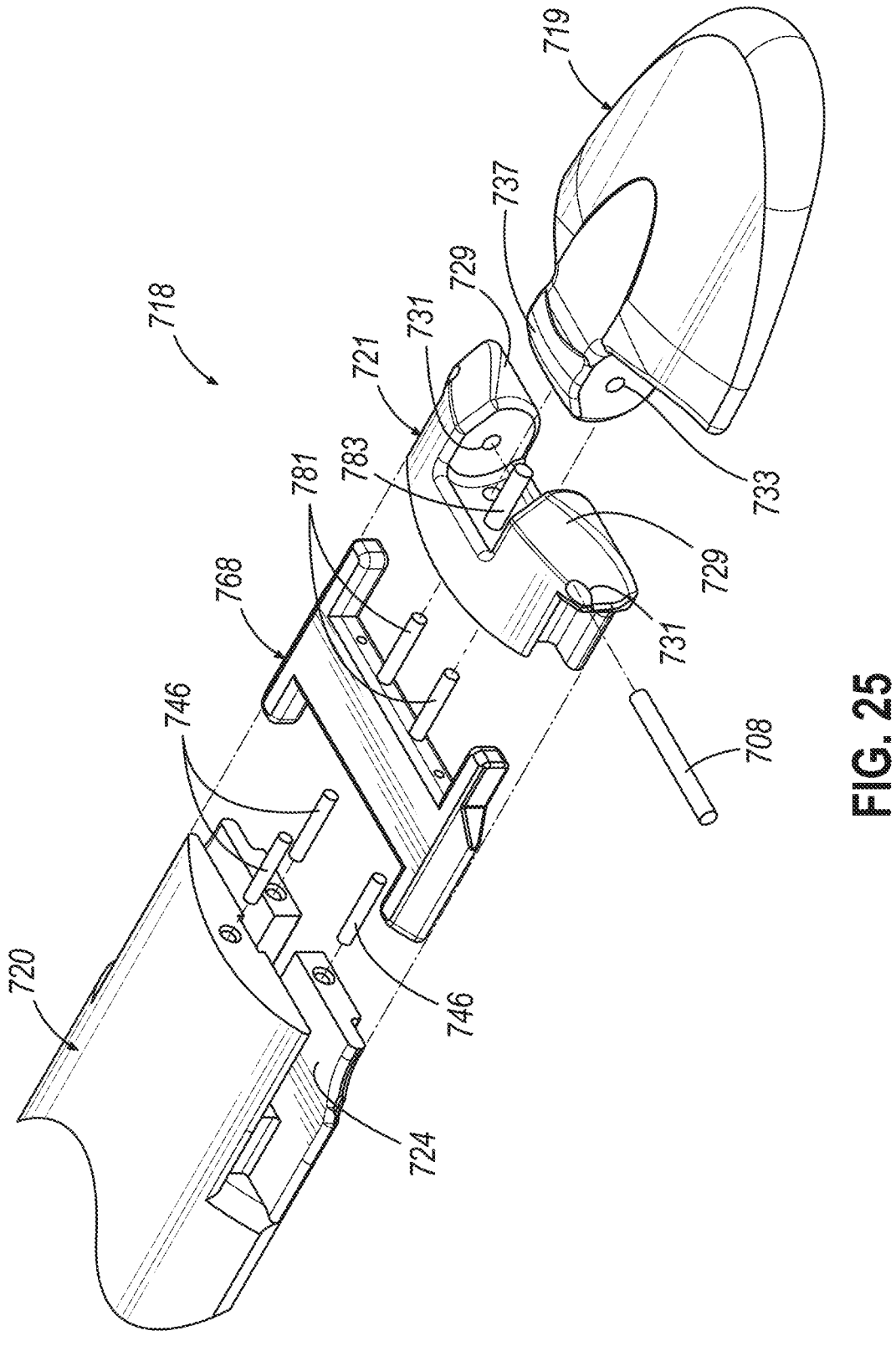
FIG. 25 depicts a proximally facing upper exploded perspective view of the distal portion of the anvil jaw of FIG. 24, showing an anvil body, a distal tip, a connector, a slider, two locking pins, a pivot pin, and three connector pins.
Figure 26:
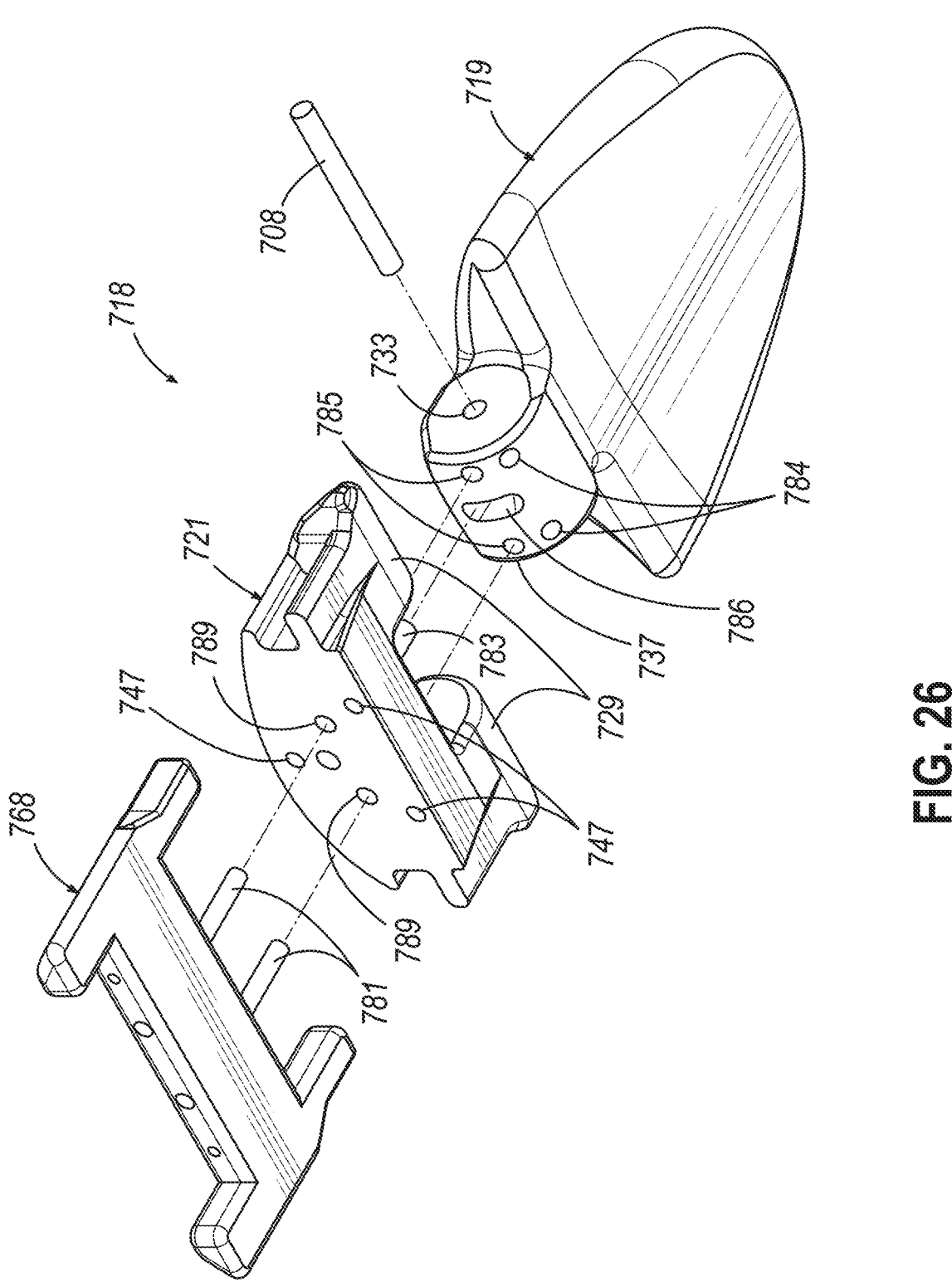
FIG. 26 depicts a distally facing lower exploded perspective view of the distal portion of the anvil jaw of FIG. 24, showing the distal tip, the connector, the slider and the pivot pin.

As shown in FIGS. 25-26, a distal end of connector (721) includes fixed range pin (783) positioned between arms (729) and extending distally toward distal tip (719). Additionally, proximal end (737) of distal tip (719) includes a range pin slot (786) sized to slidably receive a distal end of range pin (783) as distal tip (719) pivots between the first discrete position and the second discrete position. Accordingly, range pin (783) and range pin slot (786) are configured to cooperate to inhibit distal tip (719) from pivoting beyond each of the first discrete position and the second discrete position and thereby constrain distal tip (719) to a predefined range of angular motion relative to jaw body (720), where the predefined range has end points that coincide with the first and second discrete positions of distal tip (719).

D. Anvil Jaw Having Swivel Tip and Cantilever Spring

FIGS. 29-34B depict a distal portion of another illustrative anvil jaw (818) having a discretely positionable distal tip (819) and configured for use with an endoscopic surgical stapler end effector, such as any of end effectors (12, 212, 312, 412) described above.

Anvil jaw (818) includes an elongate jaw body (820) having a plurality of staple forming pockets (not shown) similar to pockets (53) of anvil (18) arranged along a length thereof. A connector (821) and a cantilever spring in the form of a cap plate (890) are coupled to a distal portion of anvil jaw body (820) such that cap plate (890) is cantilevered at its fixed proximal end over anvil jaw body (820) and connector (821). Connector (821) and cap plate (890) may be removably or fixedly coupled to anvil jaw body (820) by adhesive, welding, or fasteners, for example. A distal end of connector (821) and a distal end of cap plate (890) each includes a curved feature that cooperate to define an opening shaped as an ellipse or a circle such that when connector (821) and cap plate (890) are coupled to anvil jaw body (820), they create the opening through which a proximal end shaft (837) of distal tip (819) may be rotatably captured.

Figure 29:
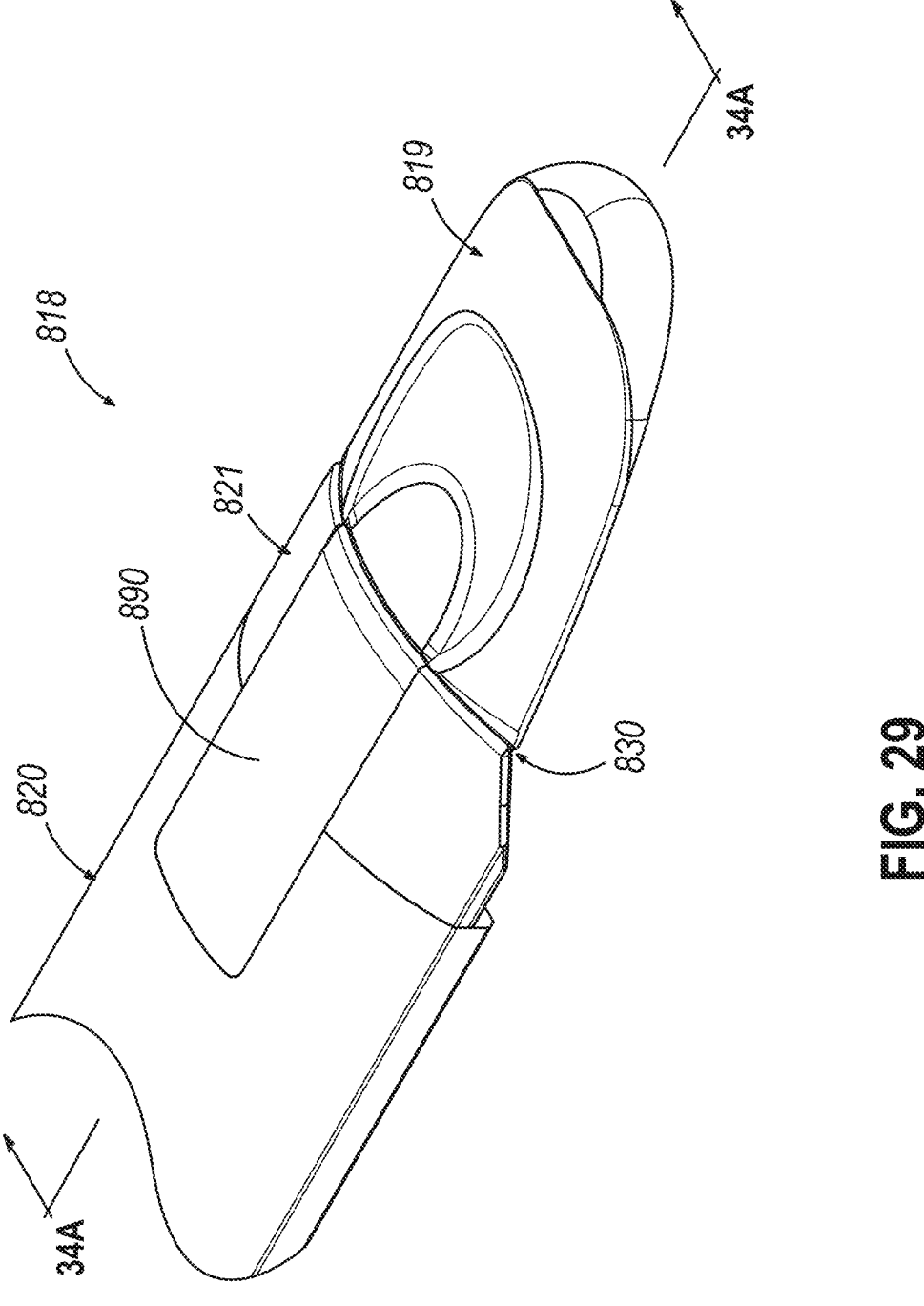
FIG. 29 depicts a perspective view of a distal portion of another anvil jaw configured for use with the surgical instruments described herein, showing a distal tip of the anvil jaw in a first discrete position.
Figure 30:
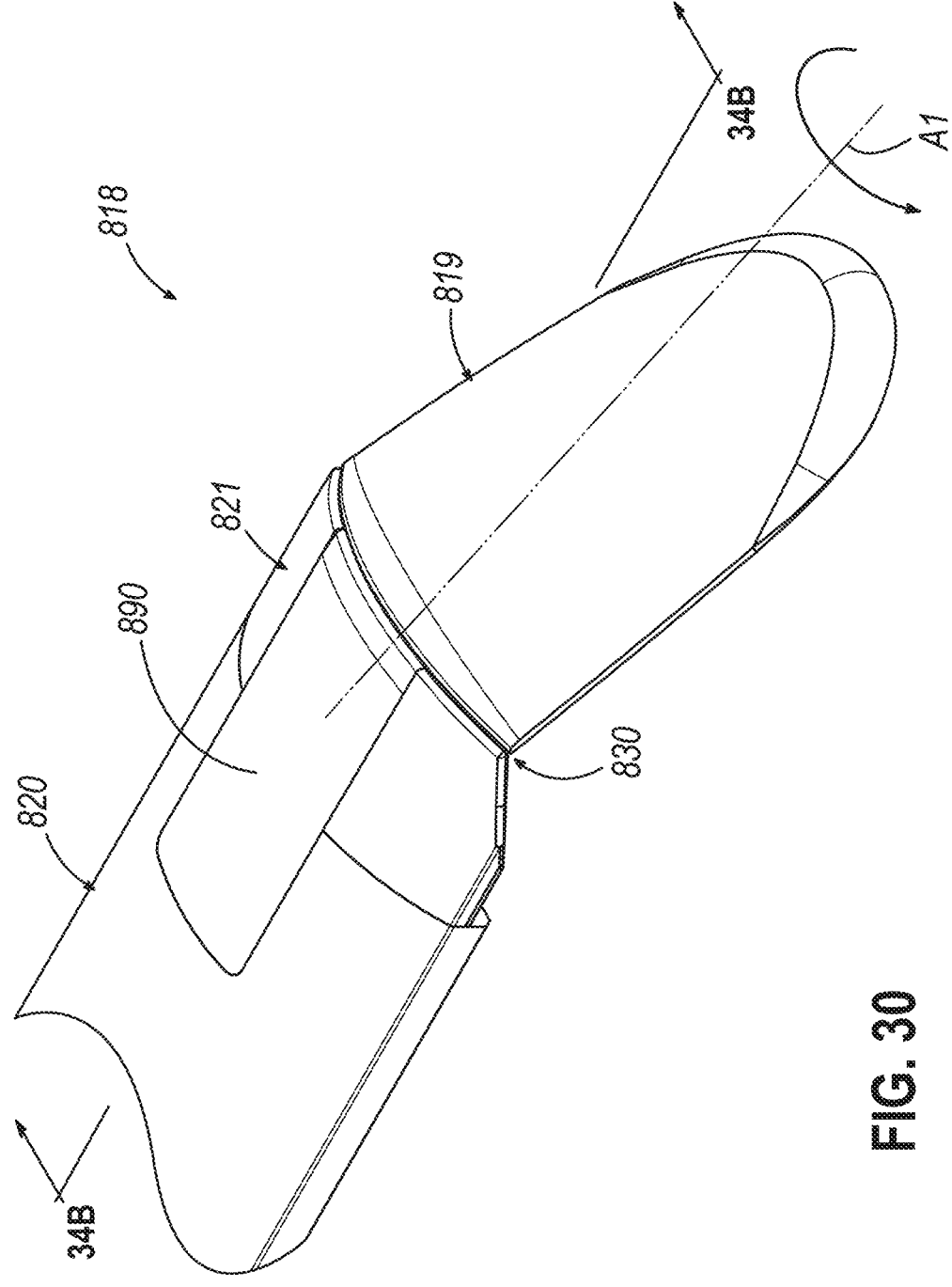
FIG. 30 depicts a perspective view of the distal portion of the anvil jaw of FIG. 29, showing the distal tip in a second discrete position.

A distal tip (819) is rotatably coupled between confronting distal ends of connector (821) and cap plate (890), and is selectively rotatable relative to anvil jaw body (820), connector (821), and cap plate (890) between first and second discrete positions about an axis (A1) defined by proximal end shaft (837) (see FIGS. 34A-34B) in response to an external rotational force applied to distal tip (819) by a user or by an adjacent anatomical structure. As shown in FIG. 29, distal tip (819) in the first discrete position is oriented straight relative to anvil jaw body (820) such that when the end effector is in the closed state, distal tip (819) extends generally parallel to lower jaw (16) and staple cartridge (37), and the distal end of distal tip (819) is thus spaced apart from the distal end of staple cartridge (37) to define a gap therebetween. Thus, distal tip (819) in the straight position is configured to provide an end effector with a distally opening aperture throughout its clamping range that is larger than a corresponding aperture exhibited by end effector when distal tip (819) is in angled position. Accordingly, similar to other exemplary versions described above, distal tip (819) in the angled position is suitably oriented to draw tissue proximally between anvil jaw (818) and staple cartridge (37) and to facilitate visualization of the target tissue during closure of end effector. Additionally, distal tip (819) in the straight position is suitably oriented to facilitate marching during a stapling procedure, as also described above. As shown in FIG. 30, distal tip (819) in the second position is angled relative to anvil jaw body (820) such that a distal end of distal tip (819) extends toward staple cartridge (37) and is configured to contact a distal end of staple cartridge (37) when anvil jaw (818) is closed to clamp tissue therebetween. A user may thus select the angled position or the straight position of distal tip (819) as desired to best facilitate a particular procedure being performed.

Figure 31:
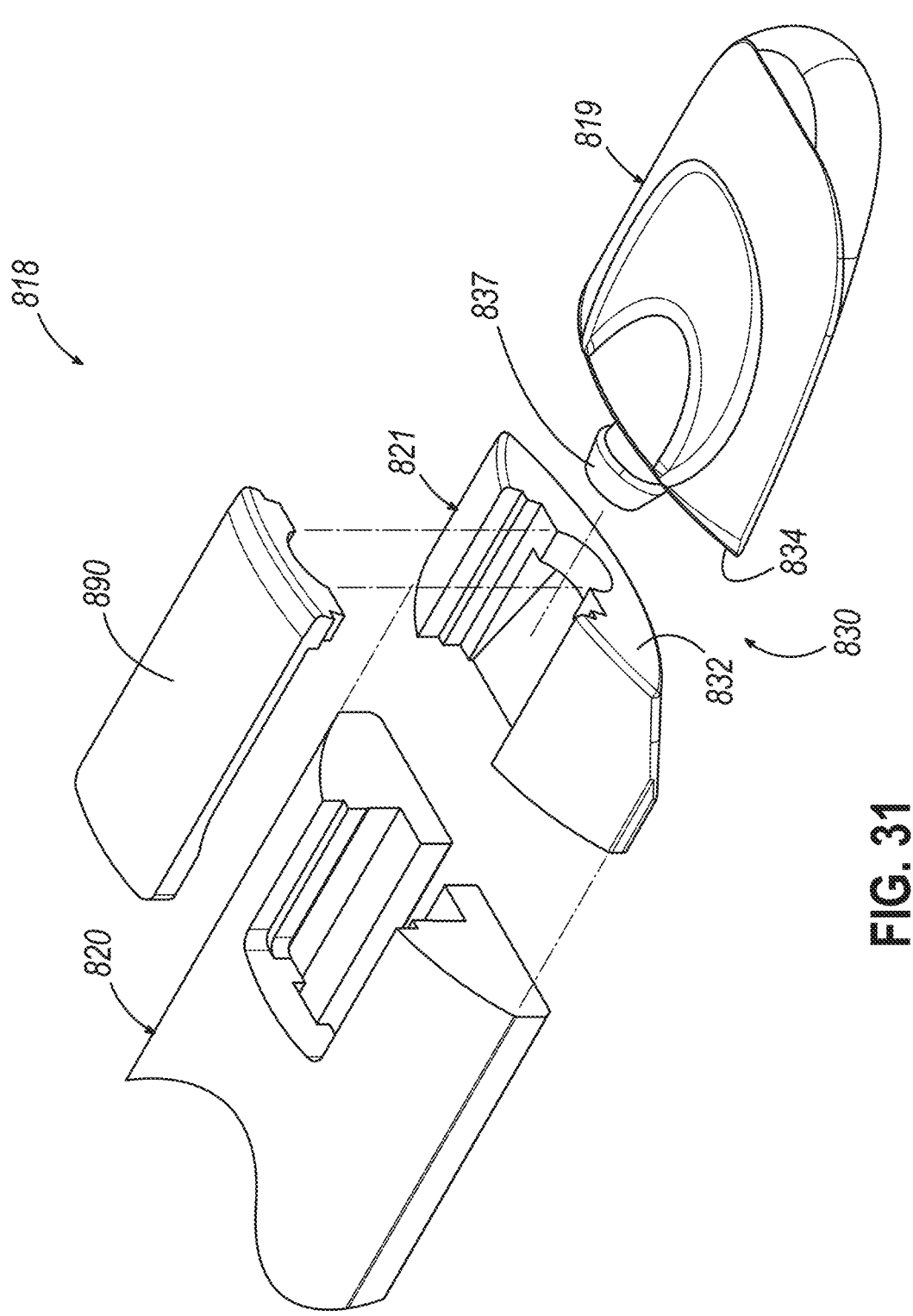
FIG. 31 depicts a proximally facing upper exploded perspective view of the distal portion of the anvil jaw of FIG. 29, showing an anvil body, a distal tip, a connector, and a cap.
Figure 32:
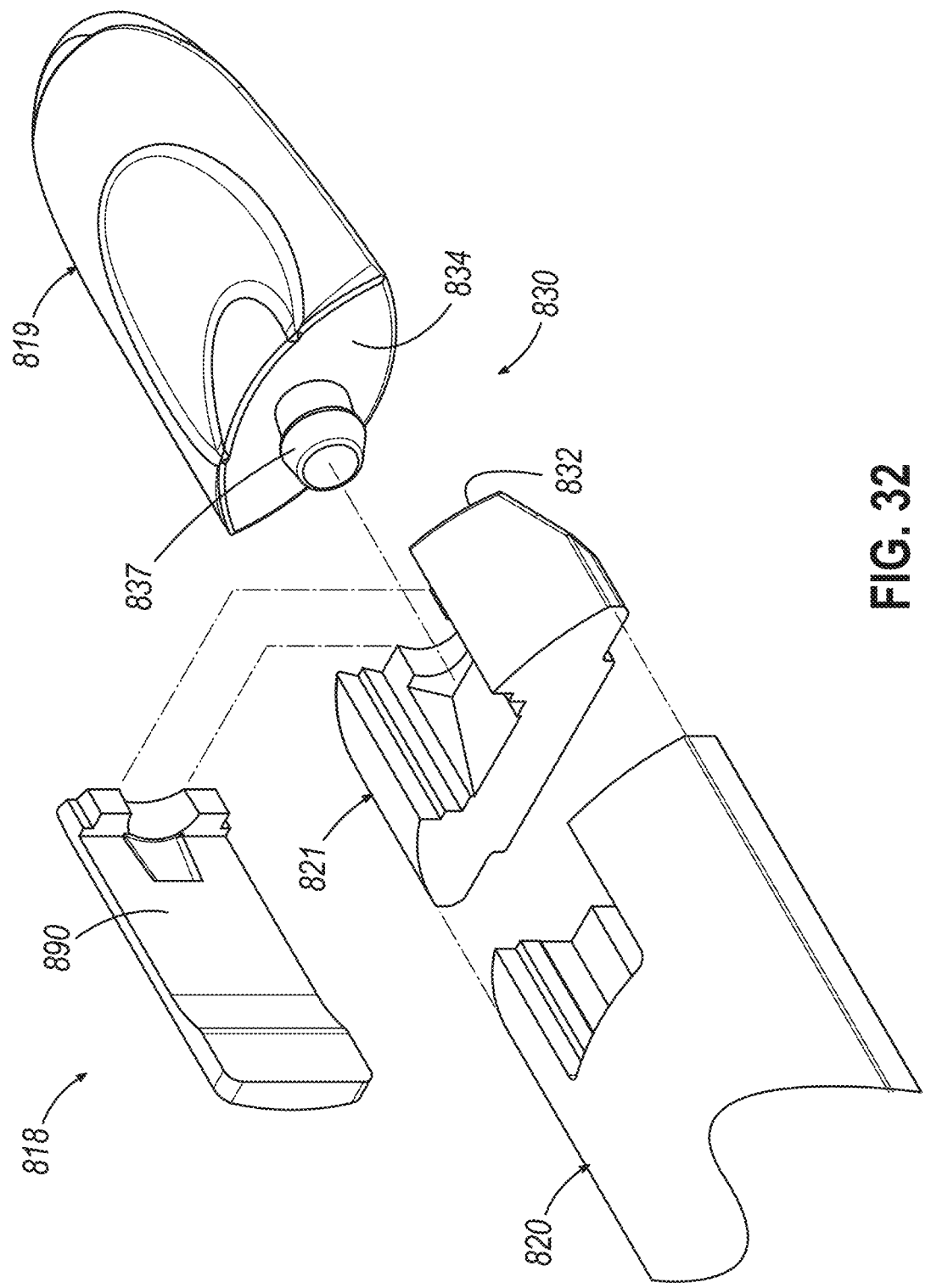
FIG. 32 depicts a distally facing upper exploded perspective view of the distal portion of the anvil jaw of FIG. 29, showing the anvil body, the distal tip, the connector, and the cap.

As shown in FIGS. 31-32, connector (821) and cap plate (890) are secured to jaw body (820) such that cap plate (890) overlies connector (821) and cooperates with a recess formed in an upper side of connector (821) to define an elongate cavity. Connector (821) and cap plate (890) cooperate to rotatably contain proximal end shaft (837) of distal tip (819) within the elongate cavity.

Figure 34A:
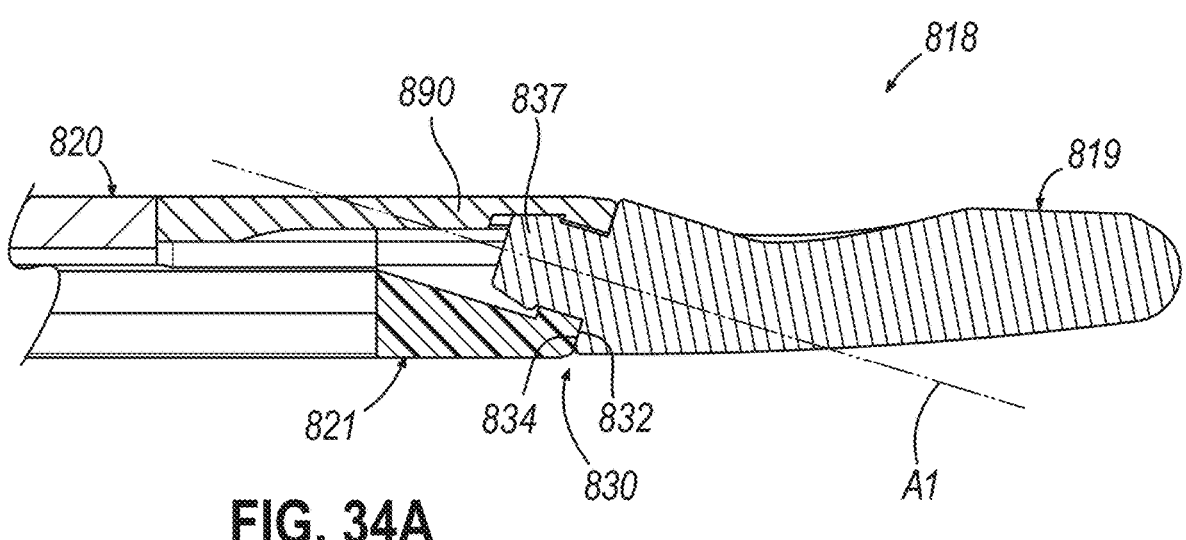
FIG. 34A depicts a side cross-sectional view of the distal portion of the anvil jaw of FIG. 29, taken along line 34A-34A of FIG. 29, showing the distal tip in the first discrete position.
Figure 34B:
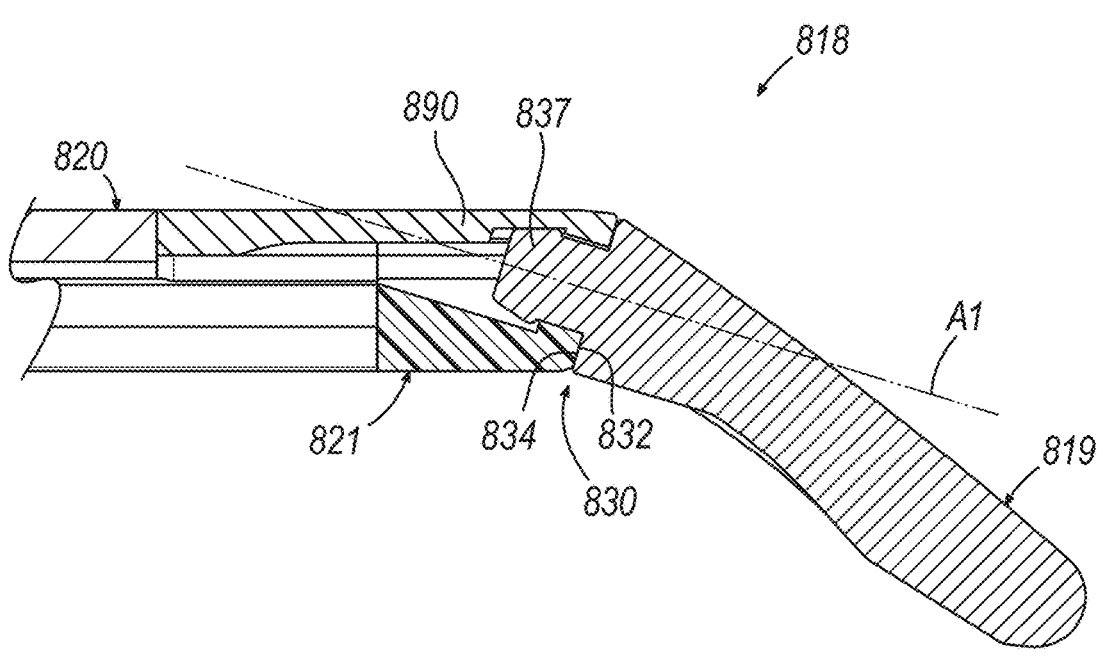
FIG. 34B depicts another side cross-sectional view of the distal portion of the anvil jaw of FIG. 30, taken along line 34B-34B of FIG. 30, showing the distal tip in the second discrete position.
Figure 35:
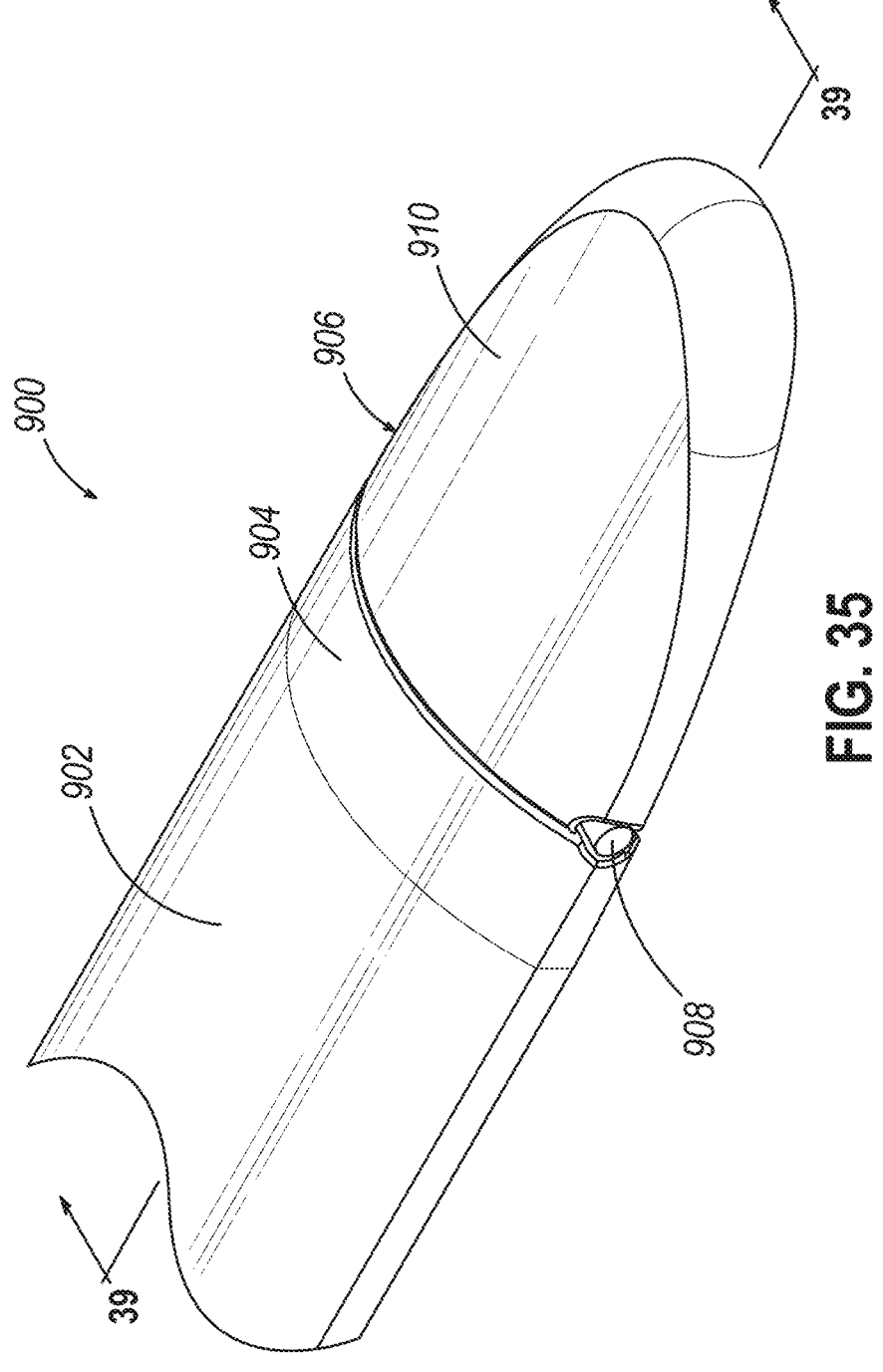
FIG. 35 depicts a perspective view of a distal portion of another anvil jaw configured for use with the surgical instruments described herein.
Figure 36:
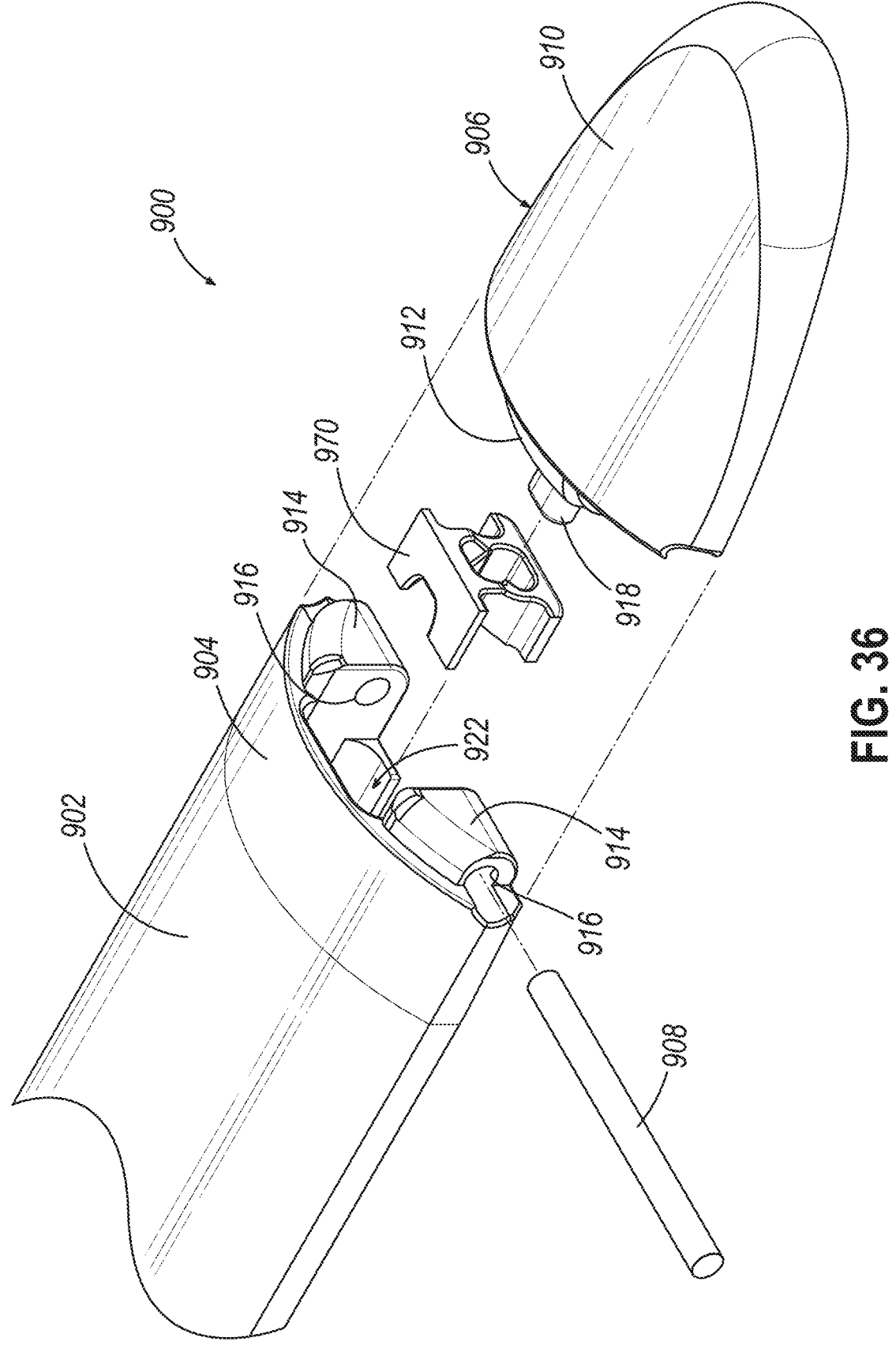
FIG. 36 depicts an exploded perspective view of the anvil jaw of FIG. 35.

Anvil jaw (818) includes an angled interface (830) defined by an angled distal face (832) of connector (821) and an angled proximal face (834) of distal tip (819). Angled faces (832, 834) are configured to engage one another in first and second mating configurations to define the first and second discrete positions of distal tip (819). As shown in FIGS. 31 and 32, angled faces (832, 834) are obliquely angled relative to the longitudinal axes of anvil jaw body (820) and distal tip (819). As shown in FIG. 34B, the oblique angles of angled interface (830) are summated when distal tip (819) is in the second rotational orientation relative to anvil jaw body (820), thus orienting the longitudinal axis of distal tip (819) obliquely relative to the longitudinal axis of anvil jaw body (820) to provide distal tip (819) in the angled position.

The first rotational orientation may be obtained by rotating distal tip (819) 180-degrees relative to the second rotational orientation. As shown in FIG. 34A, the oblique angles of angled interface (830) are configured to negate one another when distal tip (819) is in the first rotational orientation relative to anvil jaw body (820), thus aligning the longitudinal axes of anvil jaw body (820) and distal tip (819) coaxially such that distal tip (819) extends substantially straight from anvil jaw body (820). In other words, angled faces (832, 834) are oriented relative to one another in the first discrete position, shown in FIG. 34A, such that angled faces (832, 834) define supplementary angles that together define a 180-degree angle. In other versions, angled faces (832, 834) could be alternatively configured to define an angle of greater than 180 degrees when distal tip (819) is in the first position. In such versions, distal tip (819) in the first position would flare upwardly away from the distal end of staple cartridge (37) and anvil body axis.

Though not shown, anvil jaw (818) may further include a tip locking mechanism operable to releasably retain distal tip (819) in the first and second discrete positions, and thus prevent inadvertent rotation of distal tip (819) away from a selected position. Such a tip locking mechanism may comprise one or more detent features, protrusions, recesses, resilient members, interference features, and the like of various types that will be readily apparent to those of ordinary skill in the art in view of the teachings herein. For instance, anvil jaw (818) may include any one or more detent protrusions and/or detent recesses.

As shown in FIGS. 34A and 34B, distal tip (819) is configured to rotate about a rotational axis (A1) while still extending in a generally proximal-to-distal direction. The rotational axis (A1) of distal tip (819) is defined by proximal end shaft (837), described below. In the present version, the proximal end shaft (837) is suitably configured such that rotational axis (A1) extends obliquely to the longitudinal axis of distal tip (819).

Figure 33:
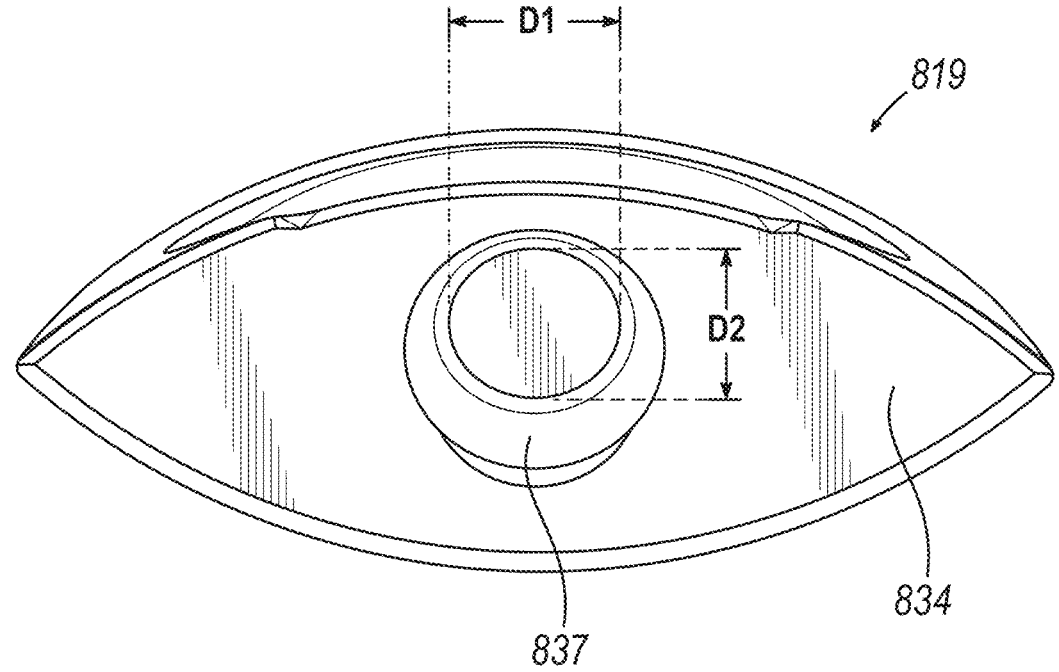
FIG. 33 depicts a distally facing end view of the distal tip of the anvil jaw of FIG. 29.

As shown in FIG. 33-34B, proximal end shaft (837) of distal tip (819) includes a tapered proximal end feature in the form of a bulbous tip that is captured between the confronting distal ends of connector (821) and cap plate (890) to thereby longitudinally constrain distal tip (819) relative to jaw body (820). The bulbous tip includes an angled cam surface and a proximal end surface, each of which has a generally elliptical profile as shown in FIG. 33. In particular, the elliptical shape includes a major diameter (D1) along a width of distal tip (819) and a minor diameter (D2) along a thickness of distal tip (819). The tapered proximal end feature of proximal end shaft (837) is captured within the elongate cavity defined between cap plate (890) and connector (821) while a distal cylindrical shaft portion of proximal end shaft (837) extends through the distal opening defined between cap plate (890) and connector (821). Accordingly, distal tip (819) is rotatable relative to connector (821) about proximal end shaft (837), while also being constrained longitudinally by the tapered proximal end feature.

Cap plate (890) functions as a cantilever leaf spring and is configured to slightly deflect transversely away from the distal end of jaw body (820) to exert a resilient force on the tapered proximal end feature of proximal end shaft (837) and thereby rotatably bias distal tip (819) toward the closest of the first discrete position or the second discrete position. In particular, when distal tip (819) is in each of the first discrete position shown in FIG. 34A and the second discrete position shown in FIG. 34B, an underside of cap plate (890) directly contacts and exerts a resilient force on the angled cam surface of the tapered proximal end feature, thereby retaining distal tip (819) in the current discrete position. Rotation of distal tip (819) away from a discrete position results in the angled cam surface of proximal end shaft (837) pushing the distal end of cap plate (890) away from connector (921), and thus causing cap plate (890) to deflect, along the major diameter (D1) of the tapered proximal end feature. In turn, this results in the underside of cap plate (890) exerting an increased resilient force on the angled cam surface. This rotatably urges distal tip (819) toward the closer of the first discrete position or the second discrete position, such that distal tip (819) may automatically snap into one of these discrete positions as soon as the external rotational input force being applied to distal tip (819) (e.g., by an operator) is removed.

E. Anvil Jaw Having Toggle Tip and Resilient Detent Insert

FIGS. 35-40C depict a distal portion of another illustrative anvil jaw (900) having a discretely positionable distal tip (906) and configured for use with an endoscopic surgical stapler end effector, such as any of end effectors (12, 212, 312, 412) described above. Anvil jaw (900) is similar to anvil jaw (518) described above except as otherwise described below.

Anvil jaw (900) includes an elongate jaw body (902) having a stapling surface with a plurality of staple forming pockets, similar to pockets (53), and a distal tip (519) movably disposed distal to jaw body (902). A distal end of jaw body (902) defines a connector portion (904) to which distal tip (906) is pivotably coupled via a pivot pin (908) that extends transversely to the longitudinal axes of jaw body (902) and distal tip (906), along a lateral width of jaw body (902) and distal tip (906). Connector portion (904) is integrally formed with the remaining proximal portion of jaw body (902) in the present version, though in other versions connector portion (904) may be separately formed and affixed to a distal end of jaw body (902), similar to connector (621) described above. Similarly, it will be appreciated that other connectors (521, 621, 721, 821) disclosed herein may be integrally formed with their respective jaw body (520, 620, 720, 820) so as to define an integral connector portion at the distal end of jaw body (520, 620, 720, 820). Distal tip (906) is configured to pivot relative to jaw body (902) about pivot pin (908) between a first discrete position to assume a straight tip orientation (see FIG. 22A) in which the longitudinal axis of distal tip is substantially parallel with the longitudinal axis of jaw body (902), and a second discrete position to assume an angled tip orientation (see FIG. 22B) in which the longitudinal axis of distal tip (906) is angled relative to the longitudinal axis of jaw body (902).

Figure 37:
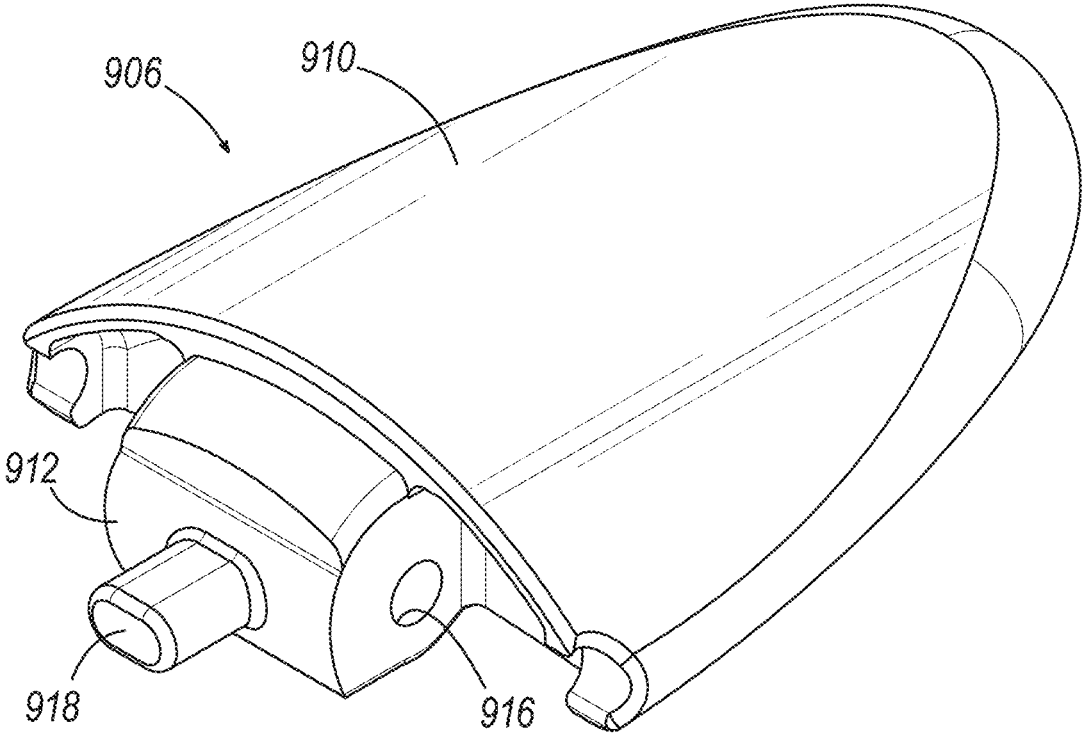
FIG. 37 depicts a distally facing perspective view of a distal tip of the anvil jaw of FIG. 35.
Figure 38:
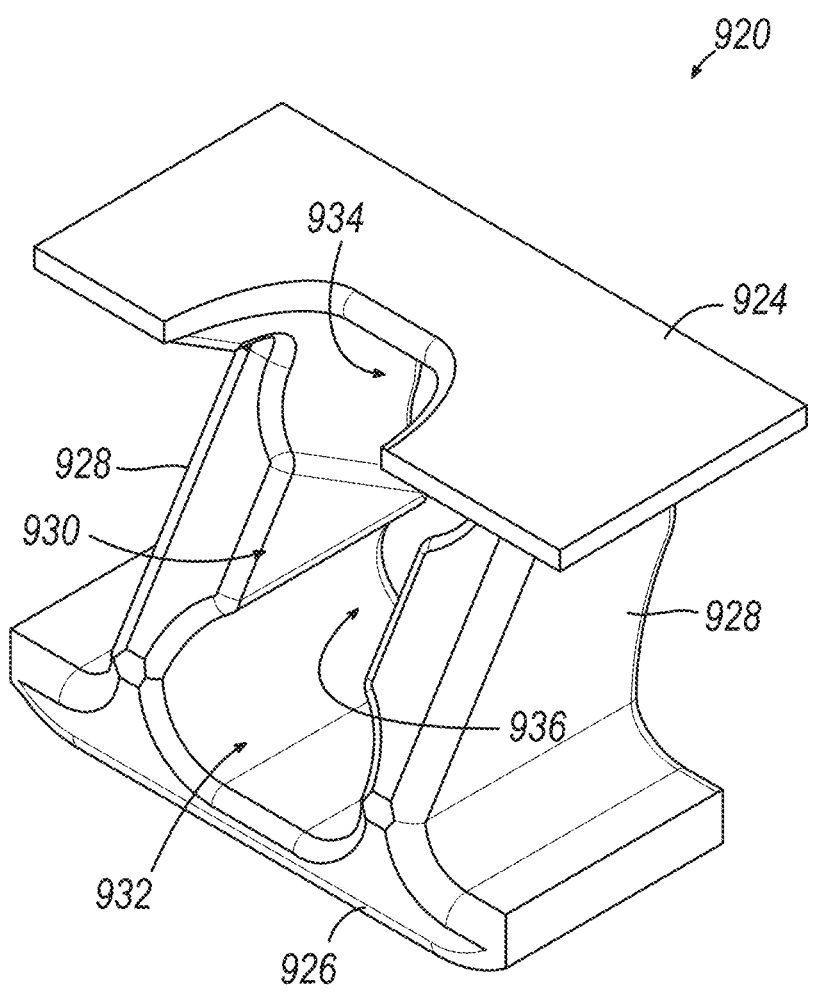
FIG. 38 depicts a distally facing perspective view of an insert of the anvil jaw of FIG. 35.

As shown best in FIG. 37, distal tip (906) includes a tip body (910) that tapers to a rounded distal end. A proximal end of tip body (910) includes a central pivot support projection (912) protruding proximally and configured to be received between side pivot support projections (914) protruding distally from connector portion (904), where projections (912, 914) include pivot pin bores (916) that align coaxially to receive pivot pin (908) laterally therethrough. A pin-like detent projection (918) extends proximally from a lower portion of central pivot support projection (912) and has a stadium shaped cross-section with a length extending parallel to a lateral width of tip body (910). The proximal end of distal tip (906) further includes stop surfaces configured to engage respective distal end surfaces of connector portion (904) to constrain distal tip (906) to a predefined range of angular motion relative to jaw body (902), where such surfaces and their functionality are similar to those described above in connection with anvil jaw (518).

Similar to distal tip (619) of anvil jaw (618), distal tip (906) is resiliently biased toward the closer of the first or second discrete position by a resilient structure supported by connector portion (904). Unlike anvil jaw (618), the resilient structure of anvil jaw (900) is in the form of an insert (920) that is housed and longitudinally fixed within a channel (922) that extends within a distal end of jaw body (902) and opens distally through connector portion (904) between side pivot support projections (914). As shown best in FIG. 38, insert (920) includes an upper flange (924), a lower flange (926), and a laterally opposed pair of sidewalls (928) that extend vertically between upper and lower flanges (924, 926) and are recessed laterally inward from the opposed ends of flanges (924, 926). An underside of lower flange (926) may include a downwardly extending protrusion configured to be received within a corresponding lower recess of channel (922) to thereby promote proper orientation of insert (920) relative to jaw body (902) during assembly of anvil jaw (618). A detent cavity (930) is defined between flanges (924, 926) and sidewalls (928) and includes a lower cavity portion (932), an upper cavity portion (934), and a medial passage (936) that interconnects cavity portions (932, 934). Each cavity portion (932, 934) is formed with a stadium shaped profile similar to that of detent projection (918) of distal tip (906) and is oriented such that a length of the cavity portion (932, 934) extends parallel to a lateral width of insert (920). Medial passage (936) interconnects lower and upper cavity portions (932, 934) along their lengths and is formed with a lateral width smaller than that of each cavity portion (932, 934) and of detent projection (918). Cavity portions (932, 934) extend longitudinally along respective longitudinal axes that are angled relative to one another so as to define a proximally opening angle, as seen in FIGS. 39A-39B.

Figure 39A:
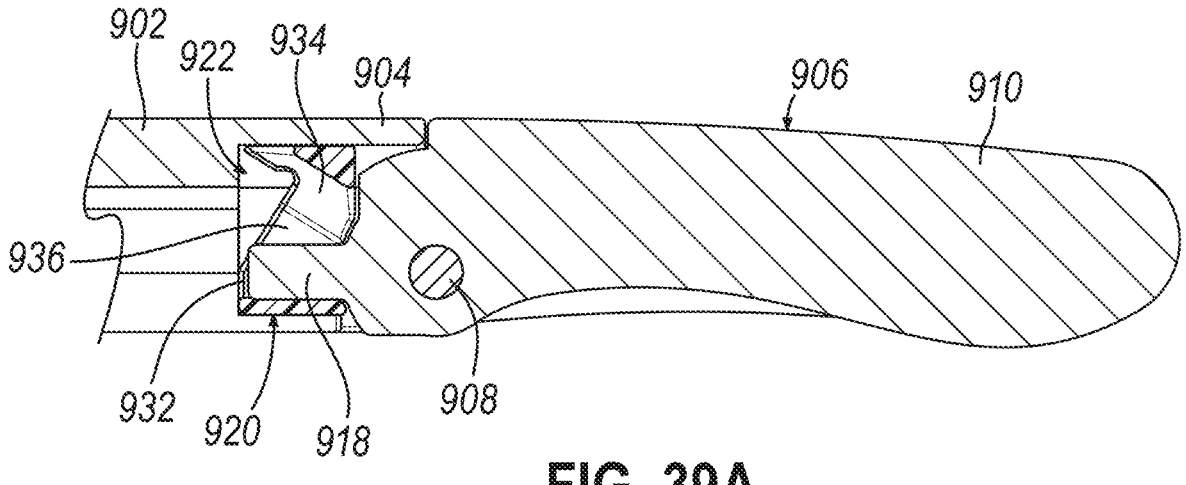
FIG. 39A depicts a side cross-sectional view of the distal portion of the anvil jaw of FIG. 35, taken along line 39-39 of FIG. 35, showing the distal tip in a first discrete position.
Figure 39B:
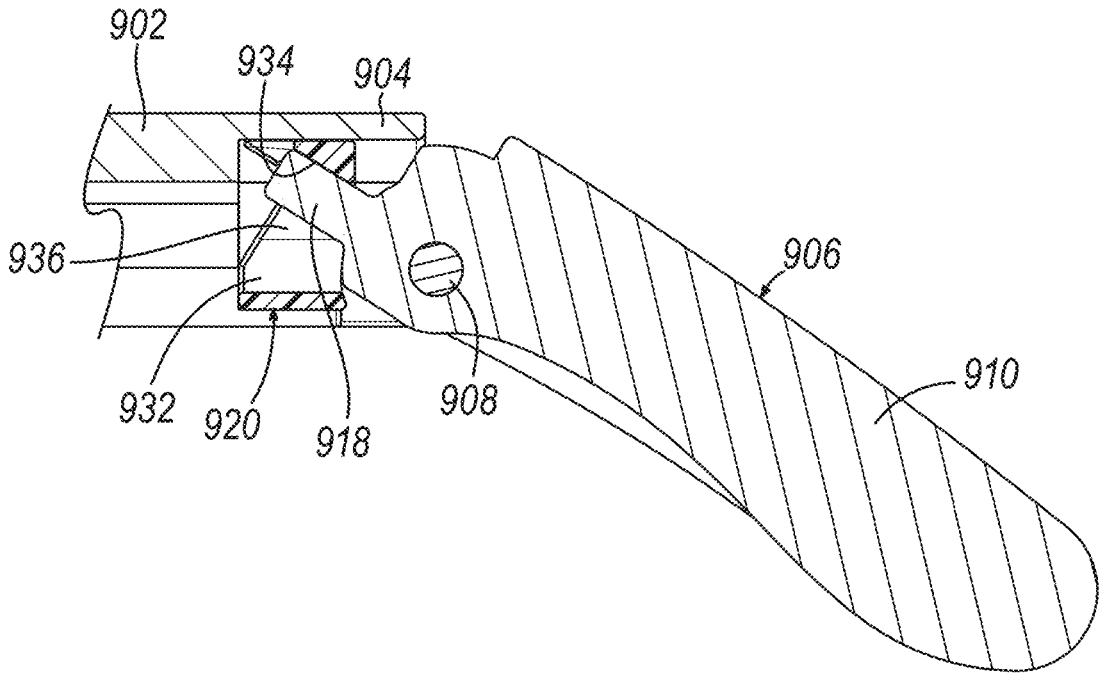
FIG. 39B depicts a side cross-sectional view of the distal portion of the anvil jaw of FIG. 35, taken along line 39-39 of FIG. 35, showing the distal tip in a second discrete position.
Figures 40A, 40B, 40C:
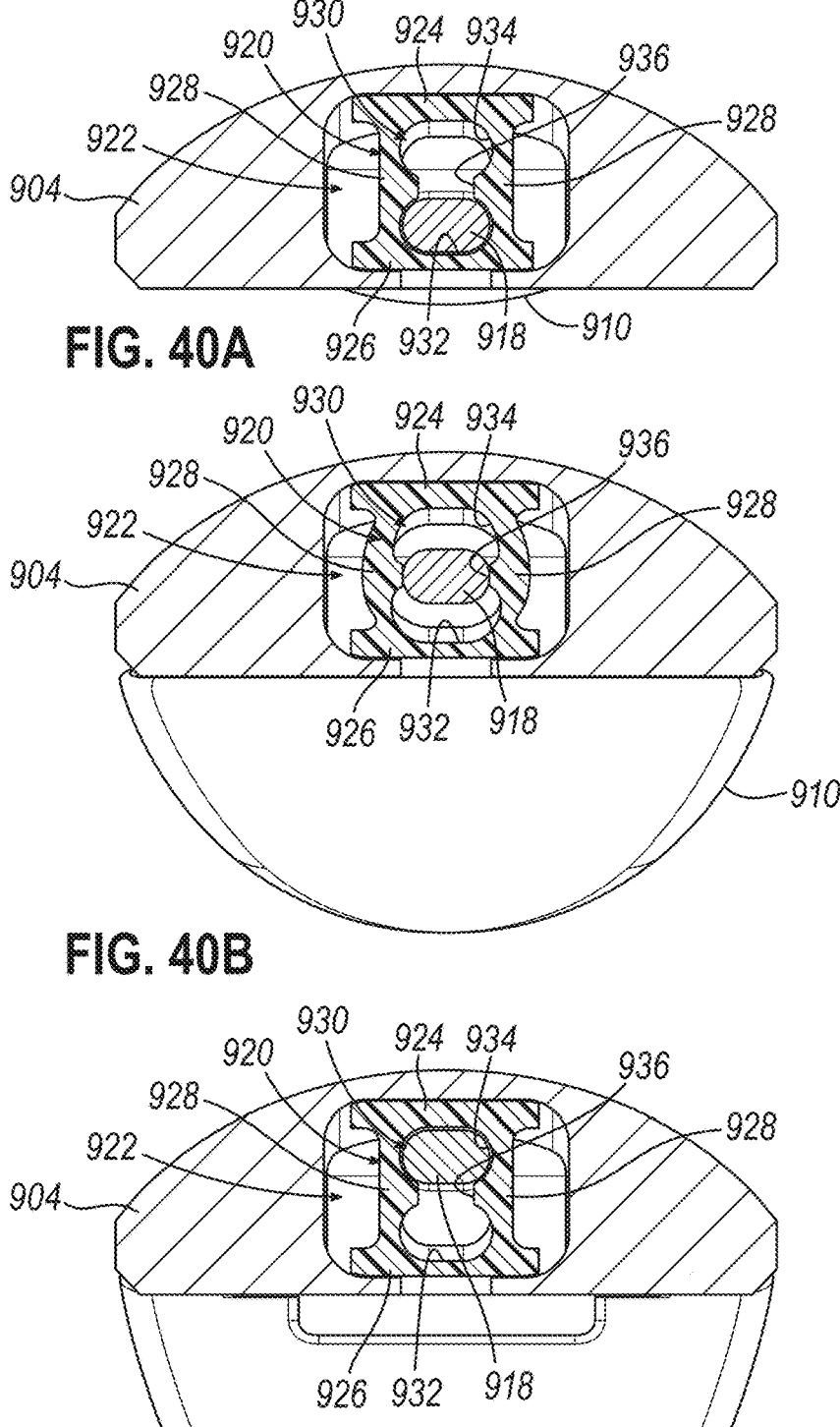
FIG. 40A depicts a distally facing cross-sectional view of the distal portion of the anvil jaw of FIG. 35, showing the distal tip in the first discrete position.
FIG. 40B depicts another distally facing cross-sectional view of the distal portion of the anvil jaw of FIG. 35, showing the distal tip between the first discrete position of FIG. 39A and the second discrete position of FIG. 39B.
FIG. 40C depicts another distally facing cross-sectional view of the distal portion of the anvil jaw of FIG. 35, showing the distal tip in the second discrete position of FIG. 39B.

As shown in FIGS. 39A and 40A, lower cavity portion (932) is configured to receive and releasably retain detent projection (918) to maintain distal tip (906) in the first discrete position relative to jaw body (902). As shown in FIGS. 39B and 40C, upper cavity portion (934) is configured to receive and releasably retain detent projection (918) to maintain distal tip (906) in the second discrete position relative to jaw body (902). As shown in FIG. 40B, insert sidewalls (928) are configured to resiliently deflect laterally outwardly into channel (922) as detent projection (918) advances vertically through medial passage (936) when transitioning between lower and upper cavity portions (932, 934). As a result, sidewalls (928) exert a resilient force laterally inwardly on detent projection (918) so as to bias detent projection (918) toward the closer of the lower cavity portion (932) or the upper cavity portion (934), thereby biasing distal tip (906) toward the closer of the first discrete position or the second discrete position. In that regard, insert (920) is formed of an elastomeric polymer configured to repeatedly elastically expand and contract as distal tip (906) transitions between the first and second discrete positions. In contrast, jaw body (902) and distal tip (906) may be formed of a more rigid material, such as a metal.

In other versions of anvil jaw (900), detent projection (918) of distal tip (906) and each detent cavity portion (932, 934) of insert (920) and may have a cross-sectional profile of various shapes other than the illustrated stadium shape, such as an elongate hexagonal shape, for example. Such shape may be selected to optimize a shear strength of detent projection (918) relative to tip body (910), as well as an external input force required to transition distal tip (906) between the first and second discrete positions.

The above-described construction of anvil jaw (900) minimizes tissue-pinching regions and provides a resilient detenting structure while otherwise maximizing the rigidity of the components of anvil jaw (900) to promote product durability and precise manipulation of tissue.

F. Alternative Toggle Tip Configured for Pinless Pivot

Figure 41:
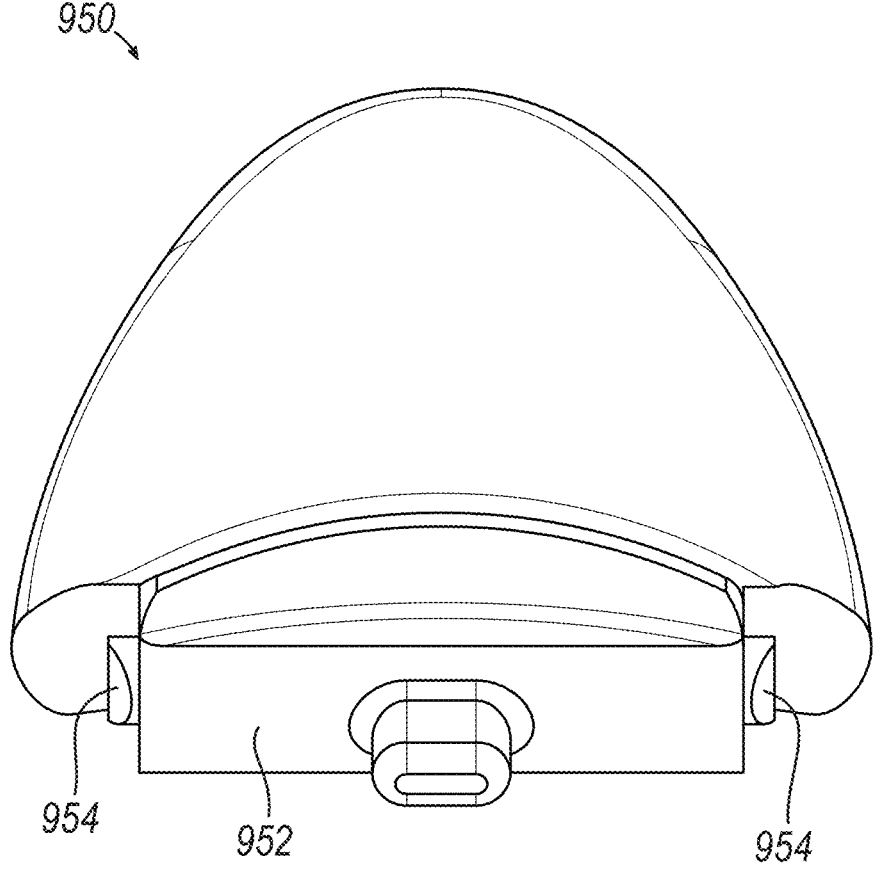
FIG. 41 depicts a distally facing perspective view of a distal tip of another anvil jaw configured for use with the surgical instruments described herein.
Figure 42A:
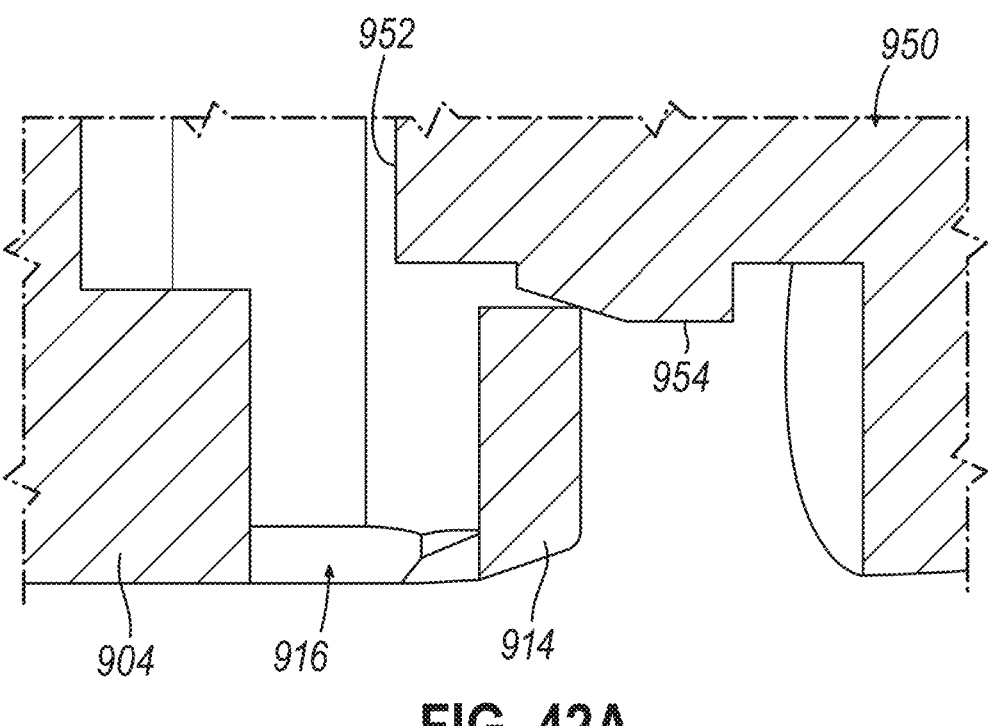
FIG. 42A depicts a top cross-sectional view of mating portions of the anvil tip of FIG. 41 and a corresponding anvil jaw, shown in a pre-assembled state.
Figure 42B:
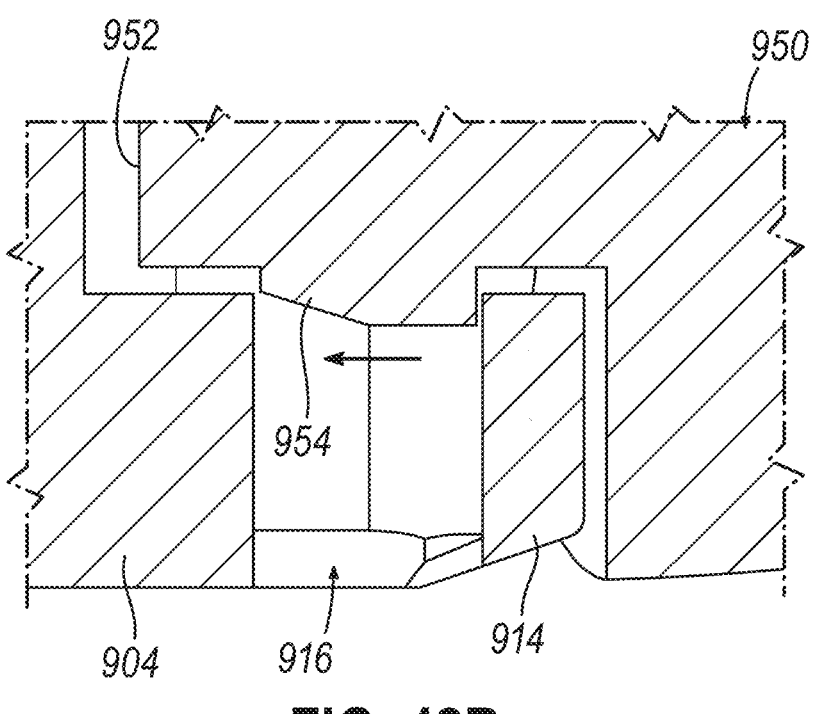
FIG. 42B depicts another top cross-sectional view of the mating portions of the anvil tip and anvil jaw of FIG. 42A, shown in an assembled state.

FIGS. 41-42B show an illustrative alternative distal tip (950) configured for use with anvil jaw (900) in place of distal tip (906). A proximal end of distal tip (950) includes a central pivot support projection (952) that omits pivot bore (916) and instead includes a pair of pivot nubs (954) that extend laterally outwardly from opposed lateral sides of central pivot support projection (952). Each pivot nub (954) is generally cylindrical and includes a lead-in chamfer on the proximally facing edge of its free end. As shown in FIGS. 42A-42B, these lead-in chamfers facilitate proximal insert of pivot nubs (954) into pivot bores (916) of connector portion (904) of jaw body (902) when distal tip (950) is assembled with jaw body (902). Pivot nubs (954) cooperate with pivot bores (916) to enable distal tip (950) to pivot relative to jaw body (902) without the need for pivot pin (908).

V. End Effector with Anvil Jaw Having Self-Actuating Distal Tip

As described above in connection with FIGS. 13-42B, anvil jaws (518, 618, 718, 818, 900) include distal tips (519, 619, 719, 819, 906) that are configured to actuate between a plurality of predefined, discrete positions in response to an external input force intentionally applied to the distal tip (519, 619, 719, 819, 906) by a clinician directly or indirectly. End effector (1000) described below in connection with FIGS. 43-45C includes an anvil jaw (1004) having a distal tip (1008) that is configured to self-actuate in response to actuation of anvil jaw (1004) relative to cartridge jaw (1002) between open and closed states.

Figure 43:
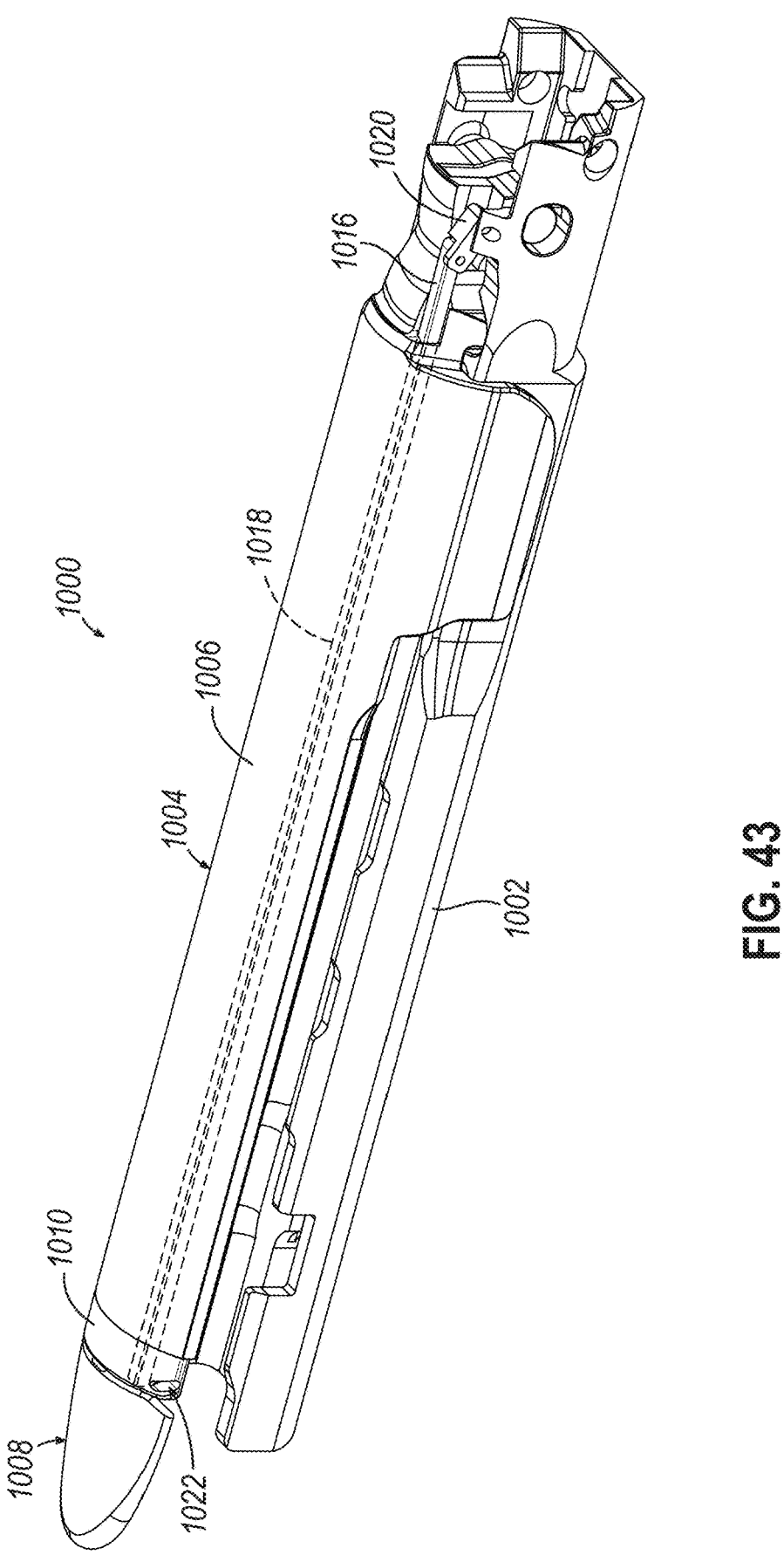
FIG. 43 depicts a perspective view of another illustrative end effector having an anvil jaw with a self-actuating distal tip.

As shown in FIG. 43, end effector (1000) includes a cartridge jaw (1002) configured to removably receive a replaceable staple cartridge, similar to staple cartridge (37), that defines a first stapling surface. End effector (1000) further includes an anvil jaw (1004) configured to pivot relative to cartridge jaw (1002) between open and closed positions in response to a user input, such as actuation of closure trigger (26). Anvil jaw (1004) includes an elongate anvil jaw body (1006) having a second stapling surface with a plurality of staple forming pockets, similar to pockets (53), a distal tip (1008) located distal to anvil jaw body (1006), and a connector (1010) disposed between distal tip (1008) and anvil jaw body (1006). Connector (1010) may be affixed to or integrally formed with a distal end of anvil jaw body (1006). A proximal end of distal tip (1008) includes a pivot support projection (1012) that is pivotably coupled with connector (1010) via a laterally extending pivot pin (1014). As discussed further below, distal tip (1008) is configured to pivot relative to connector (1010) and anvil jaw body (1006) between infinite positions in response to actuation of anvil jaw (1004) relative to cartridge jaw (1002), without a user input force applied to distal tip (1008).

Figure 44:
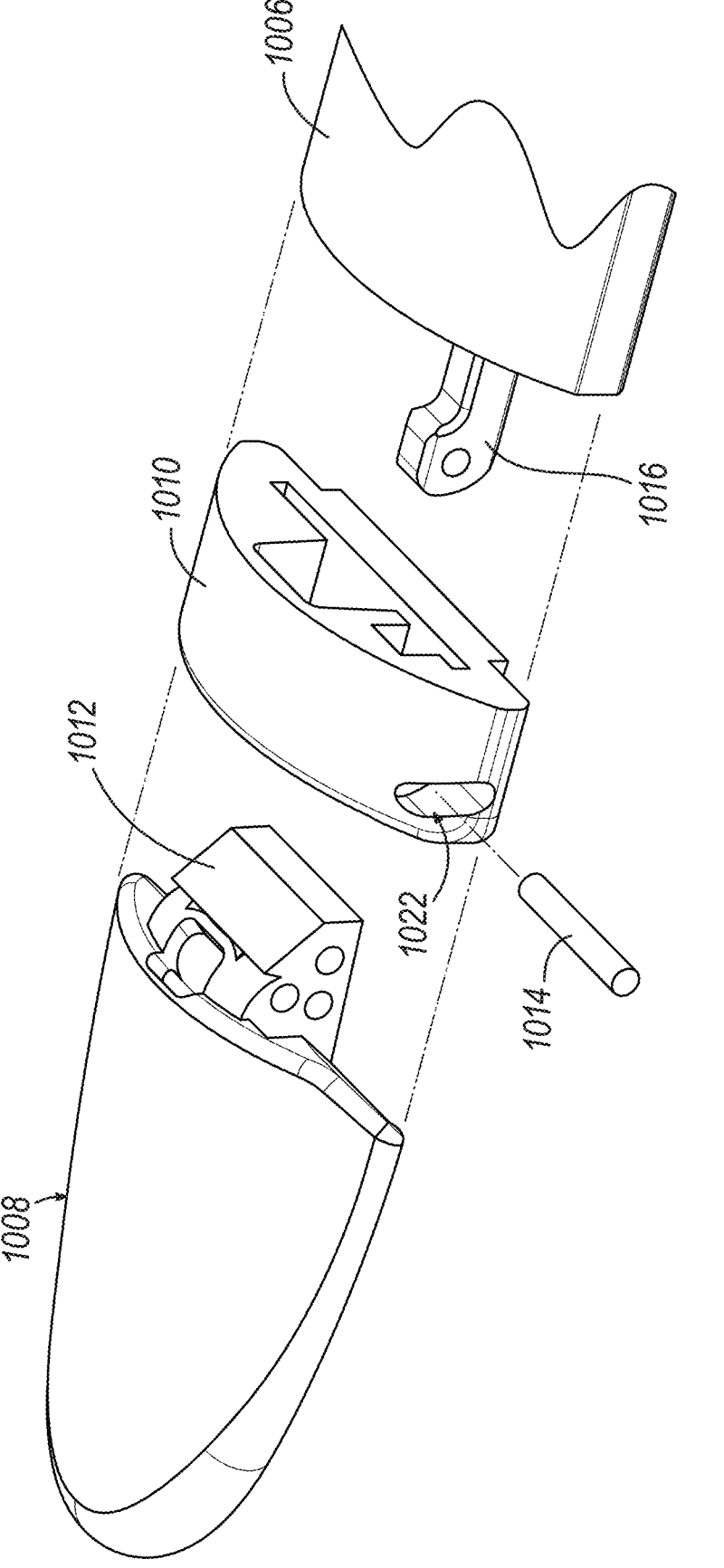
FIG. 44 depicts an exploded perspective view of a distal portion of the anvil jaw of FIG. 43.

End effector (1000) further includes an elongate linkage arm (1016) operable to actuate distal tip (1008) relative to anvil jaw body (1006) to manipulate an angular orientation of distal tip (1008) and its longitudinal axis relative to anvil jaw body (1006) and its longitudinal axis. Linkage arm (1016) is slidably housed within an elongate channel (1018) that extends longitudinally through anvil jaw body (1006) and connector (1010). A proximal end of linkage arm (1016) is pivotably coupled with a proximal end of a sidewall of cartridge jaw (1002) via a pivot coupling in the form of a short link (1020), and a distal end of linkage arm (1016) is pivotably coupled with pivot support projection (1012) of distal tip (1008) via pivot pin (1014), as seen in FIG. 44.

Connector (1010) includes a pin slot (1022) that extends laterally through connector (1010) and opens laterally to an inner cavity of connector (1010) through which the distal end of linkage arm (1016) is configured to longitudinally translate and in which pivot support projection (1012) of distal tip (1008) is configured to pivot. Pin slot (1022) has an elongate stadium shaped profile in a plane parallel to longitudinal axis of anvil jaw body (1006), and pin slot (1022) is angled such that an upper end of the profile is oriented distally and a lower end of the profile is oriented proximally. This elongate profile of pin slot (1022) permits pivot pin (1014) to translate within pin slot (1022) such that pivot pin (1014) transversely to its own longitudinal axis as distal tip (1008) pivots relative to connector (1010) and anvil jaw body (1006).

Figure 45A:
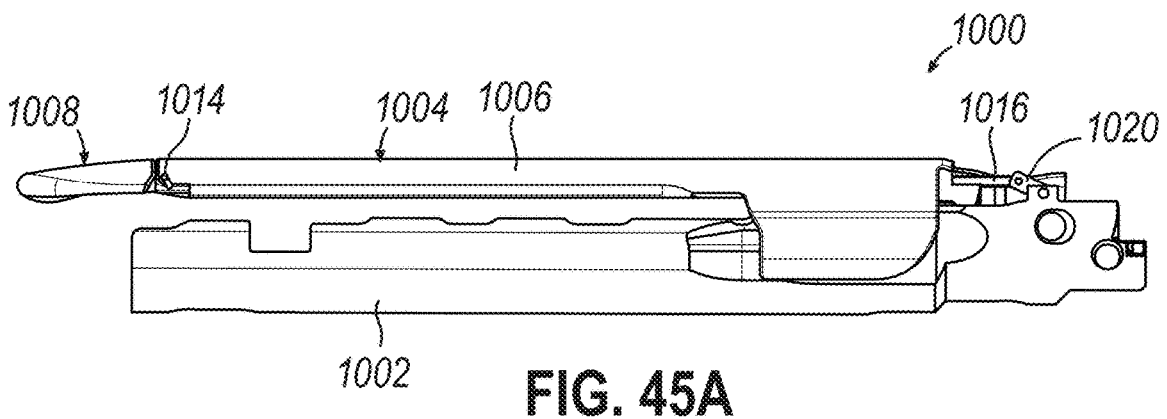
FIG. 45A depicts a side elevational view of the end effector of FIG. 43, showing the anvil jaw in a closed state and the distal tip in a respective first position relative to a body of the anvil jaw.
Figure 45B:
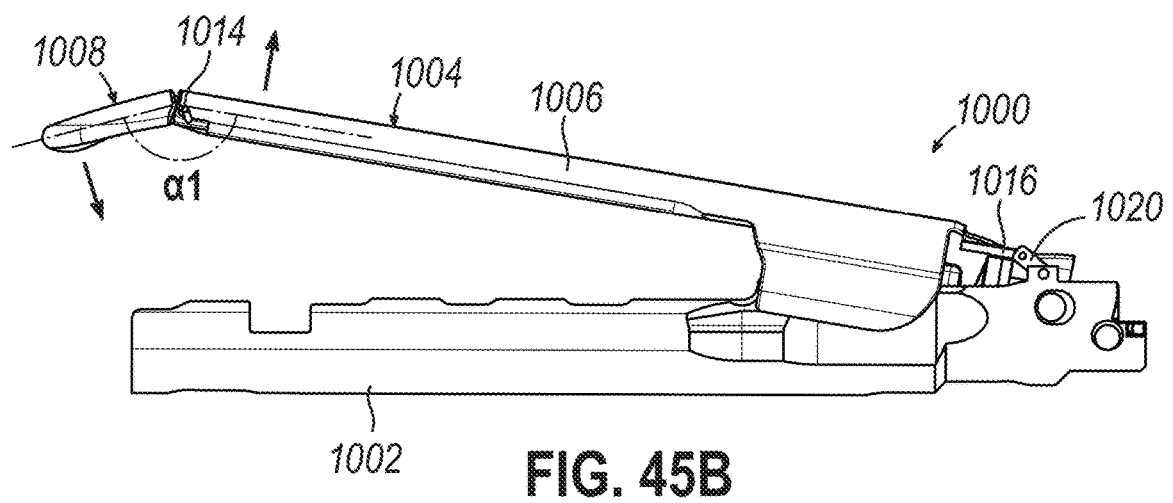
FIG. 45B depicts another side elevational view of the end effector of FIG. 43, showing the anvil jaw in a partially open state and the distal tip in a respective second position relative to the anvil jaw body.
Figure 45C:
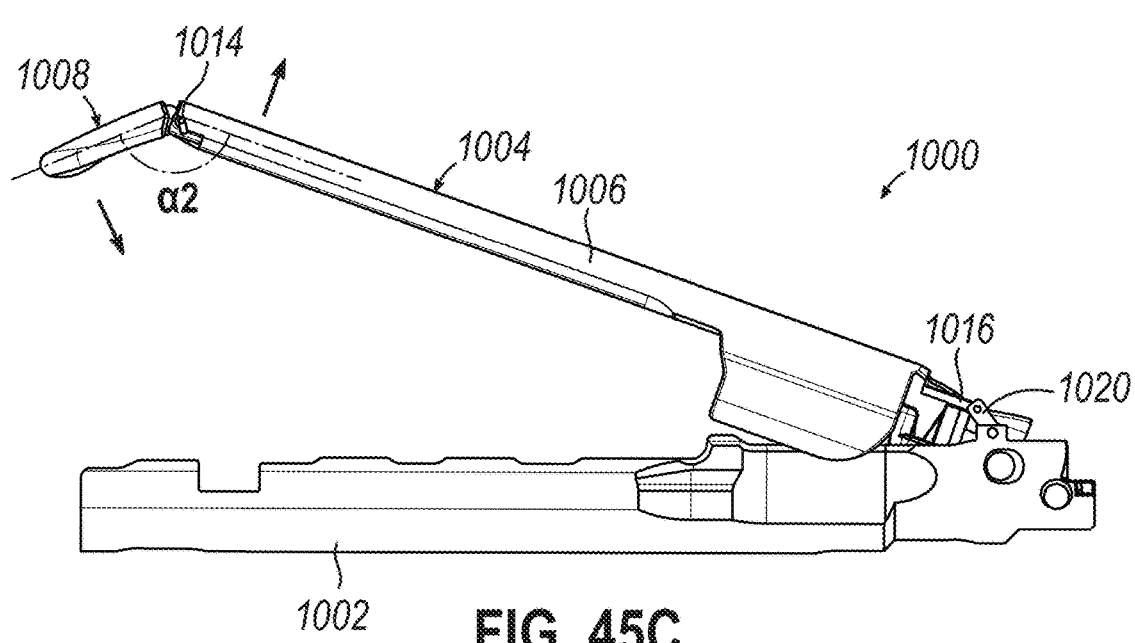
FIG. 45C depicts another side elevational view of the end effector of FIG. 43, showing the anvil jaw in fully open state and the distal tip in a respective third position relative to the anvil jaw body.

As shown in FIGS. 45A-45C, actuation of anvil jaw (1004) relative to cartridge jaw (1002) drives longitudinal translation of linkage arm (1016) within anvil jaw body (1006) and connector (1010), thereby actuating distal tip (1008) automatically relative to anvil jaw body (1006). More specifically, linkage arm (1016) is configured to actuate distal tip (1008) relative to anvil jaw body (1006) such that the longitudinal axis of distal tip (1008) defines a progressively decreasing angle relative to the longitudinal axis of anvil jaw body (1006) as anvil jaw (1004) moves from a closed state for clamping tissue toward an open state for releasing or receiving tissue.

FIG. 45A shows anvil jaw (1004) in a fully closed state relative to cartridge jaw (1002) for clamping tissue between anvil jaw (1004) and a staple cartridge (not shown) seated within cartridge jaw (1002). In this position, distal tip (1008) is oriented substantially straight relative to anvil jaw body (1006) such that the longitudinal axis of distal tip (1008) is substantially parallel to the longitudinal axis of anvil jaw body (1006). FIG. 45B shows anvil jaw (1004) in an illustrative partially-open position relative to cartridge jaw (1002) in which distal tip (1008) is orientated angularly relative to anvil jaw body (1006) such that the longitudinal axis of distal tip (1008) defines a first angle ($\alpha 1$) relative to the longitudinal axis of anvil jaw body (1006). FIG. 45C shows anvil jaw (1004) in a fully open position relative to cartridge jaw (1002) in which distal tip (1008) is oriented more angularly relative to anvil jaw body (1006) such that the longitudinal axis of distal tip (1008) defines a second angle ($\alpha 2$) relative to the longitudinal axis of anvil jaw body

(1006), where the second angle (α2) is smaller than the first angle (α1). It will be understood that distal tip (1008) assumes progressively varying angles between those illustrated as anvil jaw (1004) actuates between the positions shown in FIGS. 45A-45C.

The angled positions of distal tip (1008) relative to anvil jaw body (1006) when anvil jaw (1004) is at least partially open relative to cartridge jaw (1002) enables distal tip (1008) to effectively gather and manipulate tissue while also promoting visualization distally down the length of anvil jaw (1004). The straight position of distal tip (1008) relative to anvil jaw body (1006) when anvil jaw (1004) is closed ensures that the tissue positioned within end effector (1000) is not unduly clamped by distal tip (1008), while also facilitating marching of end effector (1000) along a tissue structure.

VI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a first jaw (16); and (b) a second jaw (618, 718, 900) configured to cooperate with the first jaw to clamp and staple tissue (90) with a plurality of staples (47), wherein the second jaw includes: (i) a jaw body (620, 720, 902) extending longitudinally along a jaw body axis, (ii) a distal tip (619, 719, 906) movably disposed distal to the jaw body and extending longitudinally along a distal tip axis, wherein the distal tip is pivotable about a pivot axis that extends transversely to the jaw body axis between a first discrete position and a second discrete position, wherein in the first discrete position the distal tip axis assumes a first orientation relative to the jaw body axis, and in the second discrete position the distal tip axis assumes a second orientation relative to the jaw body axis, (iii) first and second openings (663, 784, 785, 932, 934) both defined by one of the distal tip or a structure (621, 920) located proximal to the distal tip, and (iv) a projection (637, 781, 918) defined by the other of the distal tip or the structure, wherein the projection is positionable within the first opening (663, 785, 932) to releasably retain the distal tip in the first discrete position, wherein the projection is positionable within the second opening (663, 784, 934) to releasably retain the distal tip in the second discrete position.

Example 2

The apparatus of Example 1, wherein when the distal tip (619, 719, 906) is in the first discrete position the distal tip axis is substantially parallel to the jaw body axis, wherein when the distal tip is in the second discrete position the distal tip axis is angled relative to the jaw body axis.

Example 3

The apparatus of any of the preceding Examples, wherein the distal tip (619, 719, 906) is constrained to a predefined range of angular motion having first and second end points defined by the first and second discrete positions, respectively.

Example 4

The apparatus of any of the preceding Examples, wherein the projection (637, 918) is defined by the distal tip (619, 906).

Example 5

The apparatus of Example 4, wherein the second jaw (618, 900) further includes a resilient structure (621, 970) that defines the first and second openings (663, 932, 934), wherein the resilient structure is configured to resiliently deflect as the projection (637, 918) transitions between the first and second openings.

Example 6

The apparatus of Example 5, wherein the resilient structure (621, 970) is longitudinally fixed relative to the jaw body (620, 902) and the distal tip (619, 906).

Example 7

The apparatus of any of Examples 5 through 6, wherein the first and second openings (663, 932, 934) are interconnected.

Example 8

The apparatus of any of Examples 5 through 7, wherein the first and second openings (663, 932, 934) are arranged vertically and define respective longitudinal axes that intersect to define a proximally opening angle.

Example 9

The apparatus of any of Examples 5 through 8, wherein the resilient structure (970) comprises an insert housed within a channel (922) in a distal end of the jaw body (902).

Example 10

The apparatus of Example 9, wherein the jaw body (902) comprises a metal and the insert (970) comprises a polymer.

Example 11

The apparatus of Example 1, wherein the first and second openings (784, 785) are defined on a proximal end of the distal tip (719).

Example 12

The apparatus of Example 11, wherein the second jaw (718) further includes a latch (768) that defines the projection (781) and is actuatable relative to the jaw body (720) by a user between a lock position in which the latch inhibits movement of the distal tip relative to the jaw body, and a release position in the which latch permits movement of the distal tip relative to the jaw body.

Example 13

The apparatus of any of Example 12, wherein the latch (768) is biased toward the lock position.

Example 14

The apparatus of any of Examples 12 through 13, wherein the latch (768) is translatable relative to the jaw body (720) between the lock position and the release position.

Example 15

The apparatus of any of the preceding Examples, wherein the first jaw (16) is configured to support a stapling assembly (37) operable to deploy staples (47), wherein the second jaw (618, 718, 900) comprises an anvil jaw having a plurality of staple forming pockets (53) configured to form the staples.

Example 16

An apparatus, comprising: (a) a first jaw (16); and (b) a second jaw (618, 900) configured to cooperate with the first jaw to clamp and staple tissue (90) with a plurality of staples (47), wherein the second jaw includes: (i) a jaw body (620, extending longitudinally along a jaw body axis, (ii) a distal tip (619, 906) movably disposed distal to the jaw body and extending longitudinally along a distal tip axis, wherein the distal tip includes a detent projection (637, 918) and is pivotable about a pivot axis that extends transversely to the jaw body axis between a first discrete position and a second discrete position, wherein in the first discrete position the distal tip axis assumes a first orientation relative to the jaw body axis, and in the second discrete position the distal tip axis assumes a second orientation relative to the jaw body axis, and (iii) a resilient structure (621, 970) fixed relative to the jaw body proximal to the distal tip, wherein the resilient structure includes a detent cavity (663, 930) having first and second cavity portions (663, 932, 934) configured to receive the detent projection of the distal tip, wherein the detent projection is positionable within the first cavity portion (663, 932) to releasably retain the distal tip in the first discrete position, wherein the detent projection is positionable within the second cavity (663, 934) portion to releasably retain the distal tip in the second discrete position, wherein the resilient structure is configured to resiliently deflect as the detent projection moves between the first and second cavity portions.

Example 17

The apparatus of Example 16, wherein the resilient structure (621, 970) is longitudinally fixed relative to the jaw body (620, 902) and the distal tip (619, 906).

Example 18

The apparatus of any of Examples 16 through 17, wherein the resilient structure (621, 970) is configured to bias the detent projection (637, 918) toward the closer of the first cavity portion (663, 932) or the second cavity portion (934)

and thereby bias the distal tip (619, 906) toward the closer of the first discrete position or the second discrete position.

Example 19

The apparatus of any of Examples 16 through 18, wherein the first and second cavity portions (663, 932, 934) are arranged vertically such that the first cavity portion comprises a lower cavity portion (663, 932) and the second cavity portion comprises an upper cavity portion (663, 934).

Example 20

The apparatus of any of Examples 16 through 19, wherein the first and second cavity portions are defined by respective first and second openings (663, 932, 934) that are interconnected and extend along respective longitudinal axes that define a proximally opening angle.

Example 21

The apparatus of any of Examples 16 through 20, wherein the resilient structure comprises an insert (970) housed within a channel (922) in a distal end of the jaw body (902).

Example 22

The apparatus of Example 21, wherein the jaw body (902) comprises a metal, wherein the insert (970) comprises a polymer.

Example 23

The apparatus of any of Examples 21 through 22, wherein the insert (970) comprises a pair of insert sidewalls (928) that are laterally opposed from one another, wherein each insert sidewall is spaced inwardly from a respective inner surface of the jaw body (902) such that the insert sidewall is configured to resiliently deflect laterally outwardly into the channel (922) as the detent projection (918) transitions between the first and second cavity portions (932, 934).

Example 24

The apparatus of any of Examples 16 through 23, wherein when the distal tip (619, 906) is in the first discrete position the distal tip axis is substantially parallel to the jaw body axis, wherein when the distal tip (619, 906) is in the second discrete position the distal tip axis is angled relative to the jaw body axis.

Example 25

The apparatus of any of Examples 16 through 24, wherein the distal tip (619, 906) is constrained to a predefined range of angular motion having first and second end points defined by the first and second discrete positions, respectively.

Example 26

An apparatus, comprising: (a) a first jaw (16); and (b) a second jaw (718) configured to cooperate with the first jaw to clamp and staple tissue (90) with a plurality of staples (47), wherein the second jaw includes: (i) a jaw body (720) extending longitudinally along a jaw body axis, (ii) a latch (768) movably coupled with the jaw body, and (iii) a distal tip (719) movably disposed distal to the jaw body and the latch and extending longitudinally along a distal tip axis, wherein the distal tip is movable relative to the jaw body between a first discrete position and a second discrete position, wherein in the first discrete position the distal tip axis assumes a first orientation relative to the jaw body axis, and in the second discrete position the distal tip axis assumes a second orientation relative to the jaw body axis, wherein the latch is actuatable by a user relative to the jaw body between a lock position and a release position, wherein the latch in the lock position is configured to releasably lock the distal tip in one of the first discrete position or the second discrete position, wherein the latch in the release position is configured to permit the distal tip to transition between the first and second discrete positions.

Example 27

The apparatus of Example 26, wherein the latch (768) is translatable relative to the jaw body (720) between the lock position and the release position.

Example 28

The apparatus of any of Examples 26 through 27, wherein the latch (768) is located distally in the lock position and proximally in the release position, wherein the latch is biased toward the lock position.

Example 29

The apparatus of any of Examples 26 through 28, wherein the second jaw (718) further includes a projection (781) defined by one of the latch (768) or the distal tip (719), and first and second openings (784, 785) defined by the other of the latch or the distal tip, wherein the first opening (785) is configured to receive the projection when the distal tip is in the first discrete position and the latch is in the lock position, wherein the second opening (784) is configured to receive the projection when the distal tip is in the second discrete position and the latch is in the lock position.

Example 30

The apparatus of Example 29, wherein the projection (781) is longitudinally insertable into one of the first opening (785) or the second opening (784) as the latch transitions from the release position to the lock position.

Example 31

The apparatus of any of Examples 29 through 30, wherein the latch (768) includes the projection (781), wherein the distal tip (719) includes the first and second openings (785, 784).

Example 32

The apparatus of any of Examples 29 through 31, wherein the projection comprises a pin (781), wherein the first and second openings comprise first and second bores (785, 784) each configured to slidably receive the pin.

Example 33

The apparatus of any of Examples 29 through 32, wherein the projection (781) comprises a first projection (781), wherein the second jaw (718) further includes a second projection (781), a third opening (785) configured to receive the second projection when the distal tip is in the first discrete position, and a fourth opening (784) configured to receive the second projection when the distal tip is in the second discrete position.

Example 34

The apparatus of any of Examples 26 through 33, further comprising a connector (721) secured to a distal end of the jaw body (720), wherein the distal tip (719) is pivotably coupled to a distal end of the connector, wherein the latch (768) is actuatable within a slot (724) defined between the jaw body and the connector.

Example 35

The apparatus of any of Examples 26 through 34, wherein the distal tip (719) is constrained to a predefined range of angular motion having first and second end points defined by the first and second discrete positions, respectively.

Example 36

An apparatus, comprising: (a) a first jaw (16); and (b) a second jaw (818) configured to cooperate with the first jaw to clamp and staple tissue (90) with a plurality of staples (47), wherein the second jaw includes: (i) a jaw body (820) extending longitudinally along a jaw body axis, (ii) a distal tip (819) movably disposed distal to the jaw body and extending longitudinally along a distal tip axis, wherein the distal tip is rotatable 180 degrees relative to the jaw body between a first discrete position and a second discrete position, wherein in the first discrete position the distal tip axis assumes a first orientation relative to the jaw body axis, and in the second discrete position the distal tip axis assumes a second orientation relative to the jaw body axis, and (iii) a cantilever spring (890) configured to exert a resilient force on a proximal end of the distal tip when the distal tip is positioned between the first and second discrete positions to rotatably bias the distal tip toward the closer of the first discrete position or the second discrete position.

Example 37

The apparatus of Example 36, wherein the second jaw (818) includes an angled distal face (834) defined by a proximal end of the distal tip (819) and an angled proximal face (832) located proximal to the angled distal face, wherein the first and second angled faces are configured to engage one another in a first mating configuration to define the first discrete position of the distal tip, and in a second mating configuration to define the second discrete position of the distal tip.

Example 38

The apparatus of Example 37, wherein each of the angled distal face (834) and the angled proximal face (832) defines an oblique angle relative to the jaw body axis.

Example 39

The apparatus of any of Examples 36 through 38, wherein the cantilever spring (890) includes a fixed proximal end and a free distal end, wherein the fixed proximal end is secured to a distal end of the jaw body (820), wherein the free proximal end is configured to exert the resilient force on the proximal end of the distal tip (819).

Example 40

The apparatus of any of Examples 36 through 39, wherein the cantilever spring comprises a plate (890) that cooperates with an opposing portion of the second jaw (818) to define a cavity therebetween, wherein a proximal end (837) of the distal tip (819) is rotatable within the cavity.

Example 41

The apparatus of any of Examples 36 through 40, wherein a proximal end of the distal tip includes a shaft (837).

Example 42

The apparatus of Example 41, wherein the shaft (837) includes a bulbous tip configured to constrain the distal tip (819) longitudinally relative to the jaw body (820).

Example 43

The apparatus of Example 42, wherein the bulbous tip is rotatable within a cavity of the second jaw (818) proximal to the distal tip (819).

Example 44

The apparatus of any of Examples 42 through 43, wherein the bulbous tip includes an angled cam surface having an elliptical cross-sectional profile, wherein a free distal end of the cantilever spring (890) is configured to exert the resilient force on the angled cam surface to rotatably bias the distal tip (819) toward the closer of the first discrete position or the second discrete position.

Example 45

The apparatus of Example 44, wherein the cross-sectional profile of the bulbous tip has a major diameter along a width of the distal tip (819) and a minor diameter along a thickness of the distal tip.

Example 46

An apparatus, comprising: (a) a first jaw (1002); and (b) a second jaw (1004) configured to cooperate with the first jaw to clamp and staple tissue (90) with a plurality of staples (47), wherein the second jaw includes: (i) a jaw body (1006) extending longitudinally along a jaw body axis, (ii) a distal tip (1008) movably disposed distal to the jaw body and extending longitudinally along a distal tip axis, and (iii) a linkage arm (1016) operable to actuate the distal tip relative to the jaw body and thereby manipulate an orientation of the distal tip axis relative to the jaw body axis in response to actuation of the second jaw relative to the first jaw.

Example 47

The apparatus of Example 46, wherein the linkage arm (1016) is configured to position the distal tip (1008) such that the distal tip axis is substantially parallel with the jaw body axis when the second jaw (1004) is in a closed state relative to the first jaw (1002), wherein the linkage arm is configured to position the distal tip such that the distal tip axis is angled relative to the jaw body axis when the second jaw in an open state relative to the first jaw.

Example 48

The apparatus of any of Examples 46 through 47, wherein the linkage arm (1016) is configured to actuate the distal tip (1008) relative to the jaw body (1006) such that the distal tip axis defines a progressively decreasing angle ($\alpha$) relative to the jaw body axis as the second jaw (1004) moves from the closed state toward the open state.

Example 49

The apparatus of any of Examples 46 through 48, wherein a distal end of the linkage arm (1016) is pivotably coupled to the distal tip (1008), wherein a proximal end of the linkage arm is operatively coupled with the first jaw (1002).

Example 50

The apparatus of Example 49, wherein the distal end of the linkage arm (1016) is pivotably coupled to the distal tip (1008) with a pin (1014), wherein a distal portion of the second jaw (1004) includes a slot (1022) in which the pin is configured to translate as the second jaw actuates relative to the first jaw (1002).

Example 51

The apparatus of Example 50, wherein the pin (1014) is translatable transversely to its own longitudinal axis within the slot (1022).

Example 52

The apparatus of any of Examples 49 through 51, further comprising a connector (1010) that connects the distal tip (1008) with a distal end of the jaw body (1006), wherein the connector defines the slot (1022).

Example 53

The apparatus of any of Examples 46 through 52, further comprising a pivot coupling (1020) that couples a proximal end of the linkage arm (1016) to a proximal end of the first jaw (1002).

Example 54

The apparatus of any of Examples 46 through 53, wherein the jaw body (1006) includes an elongate channel (1018) that slidably houses the linkage arm (1016).

Example 55

The apparatus of any of Examples 46 through 54, wherein the first jaw (1002) is configured to support a stapling assembly (37) operable to deploy staples (47), wherein the second jaw comprises (1004) an anvil jaw having a plurality of staple forming pockets (53) configured to form the staples.

The following clauses also relate to various non-exhaustive ways in which the teachings herein may be combined or applied.

A. An apparatus, comprising:

(a) a first jaw; and (b) a second jaw configured to cooperate with the first jaw to clamp and staple tissue with a plurality of staples, wherein the second jaw includes:

(i) a jaw body extending longitudinally along a jaw body axis, (ii) a distal tip movably disposed distal to the jaw body and extending longitudinally along a distal tip axis, wherein the distal tip is pivotable about a pivot axis that extends transversely to the jaw body axis between a first discrete position and a second discrete position, wherein in the first discrete position the distal tip axis assumes a first orientation relative to the jaw body axis, and in the second discrete position the distal tip axis assumes a second orientation relative to the jaw body axis, (iii) first and second openings both defined by one of the distal tip or a structure located proximal to the distal tip, and (iv) a projection defined by the other of the distal tip or the structure, wherein the projection is positionable within the first opening to releasably retain the distal tip in the first discrete position, wherein the projection is positionable within the second opening to releasably retain the distal tip in the second discrete position.

B. The apparatus of claim A, wherein when the distal tip is in the first discrete position the distal tip axis is substantially parallel to the jaw body axis, wherein when the distal tip is in the second discrete position the distal tip axis is angled relative to the jaw body axis.

C. The apparatus of claim A, wherein the distal tip is constrained to a predefined range of angular motion having first and second end points defined by the first and second discrete positions, respectively.

D. The apparatus of claim A , wherein the projection is defined by the distal tip.

E. The apparatus of claim D, wherein the second jaw further includes a resilient structure that defines the first and second openings, wherein the resilient structure is configured to resiliently deflect as the projection transitions between the first and second openings.

F. The apparatus of claim F, wherein the resilient structure is longitudinally fixed relative to the jaw body and the distal tip.

G. The apparatus of claim F, wherein the first and second openings are interconnected.

H. The apparatus of claim F, wherein the first and second openings are arranged vertically and define respective longitudinal axes that intersect to define a proximally opening angle.

I. The apparatus of claim F, wherein the resilient structure comprises an insert housed within a channel in a distal end of the jaw body.

J. The apparatus of claim I, wherein the jaw body comprises a metal and the insert comprises a polymer.

K. The apparatus of claim I, wherein the first and second openings are defined on a proximal end of the distal tip.

L. The apparatus of claim K, wherein the second jaw further includes a latch that defines the projection and is actuatable relative to the jaw body by a user between a lock position in which the latch inhibits movement of the distal tip relative to the jaw body, and a release position in the which latch permits movement of the distal tip relative to the jaw body.

M. The apparatus of claim L, wherein the latch is biased toward the lock position.

N. The apparatus of claim L, wherein the latch is translatable relative to the jaw body between the lock position and the release position.

O. The apparatus of claim A, wherein the first jaw is configured to support a stapling assembly operable to deploy staples, wherein the second jaw comprises an anvil jaw having a plurality of staple forming pockets configured to form the staples.

P. An apparatus, comprising:

(a) a first jaw; and (b) a second jaw configured to cooperate with the first jaw to clamp and staple tissue with a plurality of staples, wherein the second jaw includes:

(i) a jaw body extending longitudinally along a jaw body axis, (ii) a distal tip movably disposed distal to the jaw body and extending longitudinally along a distal tip axis, wherein the distal tip is rotatable 180 degrees relative to the jaw body between a first discrete position and a second discrete position, wherein in the first discrete position the distal tip axis assumes a first orientation relative to the jaw body axis, and in the second discrete position the distal tip axis assumes a second orientation relative to the jaw body axis, and (iii) a cantilever spring configured to exert a resilient force on a proximal end of the distal tip when the distal tip is positioned between the first and second discrete positions to rotatably bias the distal tip toward the closer of the first discrete position or the second discrete position.

Q. The apparatus of claim P, wherein the second jaw includes an angled distal face defined by a proximal end of the distal tip and an angled proximal face located proximal to the angled distal face, wherein the first and second angled faces are configured to engage one another in a first mating configuration to define the first discrete position of the distal tip, and in a second mating configuration to define the second discrete position of the distal tip.

R. The apparatus of claim P, wherein the cantilever spring includes a fixed proximal end and a free distal end, wherein the fixed proximal end is secured to a distal end of the jaw body, wherein the free proximal end is configured to exert the resilient force on the proximal end of the distal tip.

S. An apparatus, comprising:

(a) a first jaw; and (b) a second jaw configured to cooperate with the first jaw to clamp and staple tissue with a plurality of staples, wherein the second jaw includes:

(i) a jaw body extending longitudinally along a jaw body axis, (ii) a distal tip movably disposed distal to the jaw body and extending longitudinally along a distal tip axis, and (iii) a linkage arm operable to actuate the distal tip relative to the jaw body and thereby manipulate an orientation of the distal tip axis relative to the jaw body axis in response to actuation of the second jaw relative to the first jaw.

T. The apparatus of claim S, wherein the linkage arm is configured to actuate the distal tip relative to the jaw body such that the distal tip axis defines a progressively decreasing angle relative to the jaw body axis as the second jaw moves from the closed state toward the open state.

VII. Miscellaneous

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467, 648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus, comprising: (a) a first jaw; and (b) a second jaw configured to cooperate with the first jaw to clamp and staple tissue with a plurality of staples, wherein the second jaw includes: (i) a jaw body extending longitudinally along a jaw body axis, (ii) a distal tip movably disposed distal to the jaw body and extending longitudinally along a distal tip axis, wherein the distal tip is pivotable about a pivot axis that extends transversely to the jaw body axis between a first discrete position and a second discrete position, wherein in the first discrete position the distal tip axis assumes a first orientation relative to the jaw body axis, and in the second discrete position the distal tip axis assumes a second orientation relative to the jaw body axis, (iii) first and second openings both defined by one of the distal tip or a structure located proximal to the distal tip, wherein the first and second openings are arranged vertically and define respective longitudinal axes that intersect to define a proximally opening angle, and (iv) a projection defined by the other of the distal tip or the structure, wherein the projection is positionable within the first opening to releasably retain the distal tip in the first discrete position, wherein the projection is positionable within the second opening to releasably retain the distal tip in the second discrete position.

2. The apparatus of claim 1, wherein when the distal tip is in the first discrete position the distal tip axis is substantially parallel to the jaw body axis, wherein when the distal tip is in the second discrete position the distal tip axis is angled relative to the jaw body axis.

3. The apparatus of claim 1, wherein the distal tip is constrained to a predefined range of angular motion having first and second end points defined by the first and second discrete positions, respectively.

4. The apparatus of claim 1, wherein the projection is defined by the distal tip.

5. The apparatus of claim 4, wherein the second jaw further includes a resilient structure that defines the first and second openings, wherein the resilient structure is configured to resiliently deflect as the projection transitions between the first and second openings.

6. The apparatus of claim 5, wherein the resilient structure is longitudinally fixed relative to the jaw body and the distal tip.

7. The apparatus of claim 5, wherein the first and second openings are interconnected.

8. The apparatus of claim 5, wherein the resilient structure comprises an insert housed within a channel in a distal end of the jaw body.

9. The apparatus of claim 8, wherein the jaw body comprises a metal and the insert comprises a polymer.

10. The apparatus of claim 1, wherein the first and second openings are defined on a proximal end of the distal tip.

11. The apparatus of claim 10, wherein the second jaw further includes a latch that defines the projection and is actuatable relative to the jaw body by a user between a lock position in which the latch inhibits movement of the distal tip relative to the jaw body, and a release position in the which latch permits movement of the distal tip relative to the jaw body.

12. The apparatus of claim 11, wherein the latch is biased toward the lock position.

13. The apparatus of claim 11, wherein the latch is translatable relative to the jaw body between the lock position and the release position.

14. The apparatus of claim 1, wherein the first jaw is configured to support a stapling assembly operable to deploy staples, wherein the second jaw comprises an anvil jaw having a plurality of staple forming pockets configured to form the staples.

* * * * *